(12) United States Patent
Kalnik et al.

(10) Patent No.: US 11,597,916 B2
(45) Date of Patent: Mar. 7, 2023

(54) NICOTINE DEGRADING ENZYME VARIANTS

(71) Applicants: ANTIDOTE THERAPEUTICS, INC., Sykesville, MD (US); BOARD OF REGENTS, THE UNIVERSITY OF TEXAS SYSTEM, Austin, TX (US)

(72) Inventors: Matthew W. Kalnik, Bethesda, MD (US); Thomas Thisted, New Market, MD (US); Everett Stone, Austin, TX (US); Charles C. Reed, Souderton, PA (US); Max Rodnick-Smith, Austin, TX (US)

(73) Assignees: ANTIDOTE THERAPEUTICS, INC., Bethesda, MD (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 346 days.

(21) Appl. No.: 16/483,380

(22) PCT Filed: Feb. 2, 2018

(86) PCT No.: PCT/US2018/016664
§ 371 (c)(1),
(2) Date: Aug. 2, 2019

(87) PCT Pub. No.: WO2018/144879
PCT Pub. Date: Aug. 9, 2018

(65) Prior Publication Data
US 2020/0224176 A1 Jul. 16, 2020

Related U.S. Application Data

(60) Provisional application No. 62/535,507, filed on Jul. 21, 2017, provisional application No. 62/454,331, filed on Feb. 3, 2017.

(51) Int. Cl.
| | | |
|---|---|---|
| *C12N 9/00* | (2006.01) | |
| *C12N 9/04* | (2006.01) | |
| *A61K 47/60* | (2017.01) | |
| *A61P 43/00* | (2006.01) | |
| *C12N 9/02* | (2006.01) | |

(52) U.S. Cl.
CPC ............ *C12N 9/0006* (2013.01); *A61K 47/60* (2017.08); *A61P 43/00* (2018.01); *C12N 9/0004* (2013.01)

(58) Field of Classification Search
CPC ....... B32B 27/38; B32B 27/42; C12N 9/0073; C12N 9/0004; C12Y 105/99004; C12Y 117/02001

USPC ............................ 435/189, 252.2, 320.1, 25
See application file for complete search history.

(56) References Cited

U.S. PATENT DOCUMENTS

2019/0153403 A1    5/2019    Xu et al.

FOREIGN PATENT DOCUMENTS

| WO | WO-2017/023904 | | 2/2017 |
| WO | WO-2017/167250 | A1 | 10/2017 |
| WO | WO-2018/144879 | | 8/2018 |
| WO | WO-2019/126364 | A2 | 6/2019 |
| WO | WO-2020-027970 | | 2/2020 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Qiu et al., "Cloning of a Novel Nicotine Oxidase Gene from *Pseudomonas* sp. Strain HZN6 Whose Product Nonenantioselectively Degrades Nicotine to Pseudooxynicotine," Applied and Environmental Microbiology, vol. 79, No. 7, 99. 2164-2171 (Apr. 2013).
Tararina et al., "Structural Analysis Provides Mechanistic Insight into Nicotine Oxidoreductase from Pseudomonas putida," Biochemistry, vol. 55, pp. 6595-6598 (Nov. 2016).
Xia et al., "Genome-wide investigation of the genes involved in nicotine metabolism in Pseudomonas putida J5 by Tn5 transposon," Appl. Microbiol. Biotechnol., vol. 99, pp. 6503-6514 (Mar. 2015).
Xue et al., "A New Strategy for Smoking Cessation: Characterization of a Bacterial Enzyme for the Degradation of Nicotine," J. Am. Chem. Soc., vol. 137, pp. 10136-10139 (Aug. 2015).
Tararina et al., "Crystallography Coupled with Kinetic Analysis Provides Mechanistic Underpinnings of a Nicotine-Degrading Enzyme," Biochemistry, vol. 57, No. 26, pp. 3741-3751 (Jul. 2018).
Thisted et al., "Optimization of a nicotine degrading enzyme for potential use in treatment of nicotine addiction," BMC Biotechnology, vol. 19, No. 56, pp. 1-16 (Aug. 2019).
Database DDBJ/EMBL/GenBank [online],Accession No. AEJ14620 <https://www.ncbi.nlm.nih.gov/protein/AEJ14620> Jan. 31, 2014 uploaded, [retrieved on Dec. 28, 2021] Definition: amine oxidase [Pseudomonas putida S16].

* cited by examiner

*Primary Examiner* — Robert B Mondesi
*Assistant Examiner* — Mohammad Y Meah
(74) *Attorney, Agent, or Firm* — Foley & Lardner LLP

(57) ABSTRACT

Described are nicotine-degrading enzyme variants that exhibit increased nicotine-degrading activity and/or decreased immunogenicity relative to the wild-type NicA2 and NOX enzymes, compositions comprising the variants, and methods using them.

24 Claims, 13 Drawing Sheets
Specification includes a Sequence Listing.

FIG 4E

Relative Activities of Epitope B Variants

SEQUENCE LISTING

<160> NUMBER OF SEQ ID NOS: 144

<210> SEQ ID NO 1
<211> LENGTH: 482
<212> TYPE: PRT
<213> ORGANISM: Pseudomonas putida
<220> FEATURE:
<221> NAME/KEY: source
<223> OTHER INFORMATION: /note="See specification as filed for detailed -continued description of substitutions and preferred embodiments"

<400> SEQUENCE: 1

```
Met Ser Asp Lys Thr Lys Thr Asn Glu Gly Phe Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
            35                  40                  45

Lys Gly Gly Phe Asp Tyr Asp Val Val Val Gly Gly Gly Phe Ala
    50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
                100                 105                 110

Gln Pro His Val Trp Ala Glu Met Gln Arg Tyr Gly Leu Gly Val Val
                115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
                180                 185                 190

Ser Val Leu Asp Arg Ile Lys Thr Leu Gly Leu Ser Arg Leu Gln Gln
            195                 200                 205

Ala Gln Ile Asn Ser Tyr Met Ala Leu Tyr Ala Gly Glu Thr Thr Asp
    210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
                260                 265                 270

Val Arg Met Ser Val Pro Val Thr Ala Val Glu Gln Val Asn Gly Gly
            275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
                340                 345                 350

Phe Ala Phe Ala Asp Glu Gln Gln Pro Leu Asn Trp Val Gln Thr His
            355                 360                 365

Asp Tyr Ser Asp Glu Leu Gly Thr Ile Leu Ser Ile Thr Ile Ala Arg
    370                 375                 380

Lys Glu Thr Ile Asp Val Asn Asp Arg Asp Ala Val Thr Arg Glu Val
385                 390                 395                 400
```

-continued

```
Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Asn Ile Asp
450                 455                 460

Gly Ala Val Glu Ser Gly Leu Arg Ala Gly Arg Glu Val Lys Gln Leu
465                 470                 475                 480

Leu Ser

<210> SEQ ID NO 2
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270
```

```
Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 3
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Val Ala Gly Leu Gly Ala Ile Asp Ala Ala Ser Ala Thr Gln Lys
1               5                   10                  15

Thr Asn Arg Ala Ser Thr Val Lys Gly Gly Phe Asp Tyr Asp Val Val
                20                  25                  30

Val Val Gly Gly Gly Phe Ala Gly Ala Thr Ala Ala Arg Glu Cys Gly
                35                  40                  45

Leu Gln Gly Tyr Arg Thr Leu Leu Leu Glu Ala Arg Ser Arg Leu Gly
        50                  55                  60

Gly Arg Thr Phe Thr Ser Arg Phe Ala Gly Gln Glu Ile Glu Phe Gly
65                  70                  75                  80

Gly Ala Trp Val His Trp Leu Gln Pro His Val Trp Ala Glu Met Gln
                85                  90                  95

Arg Tyr Gly Leu Gly Val Val Glu Asp Pro Leu Thr Asn Leu Asp Lys
            100                 105                 110

Thr Leu Ile Met Tyr Asn Asp Gly Ser Val Glu Ser Ile Ser Pro Asp
        115                 120                 125

Glu Phe Gly Lys Asn Ile Arg Ile Ala Phe Glu Lys Leu Cys His Asp
130                 135                 140

Ala Trp Glu Val Phe Pro Arg Pro His Glu Pro Met Phe Thr Glu Arg
145                 150                 155                 160

Ala Arg Glu Leu Asp Lys Ser Ser Val Leu Asp Arg Ile Lys Thr Leu
                165                 170                 175

Gly Leu Ser Arg Leu Gln Gln Ala Gln Ile Asn Ser Tyr Met Ala Leu
            180                 185                 190
```

```
Tyr Ala Gly Glu Thr Thr Asp Lys Phe Gly Leu Pro Gly Val Leu Lys
            195                 200                 205

Leu Phe Ala Cys Gly Gly Trp Asn Tyr Asp Ala Phe Met Asp Thr Glu
    210                 215                 220

Thr His Tyr Arg Ile Gln Gly Thr Ile Gly Leu Ile Asn Ala Met
225                 230                 235                 240

Leu Thr Asp Ser Gly Ala Glu Val Arg Met Ser Val Pro Val Thr Ala
                245                 250                 255

Val Glu Gln Val Asn Gly Gly Val Lys Ile Lys Thr Asp Asp Asp Glu
                260                 265                 270

Ile Ile Thr Ala Gly Val Val Met Thr Val Pro Leu Asn Thr Tyr
            275                 280                 285

Lys His Ile Gly Phe Thr Pro Ala Leu Ser Lys Gly Lys Gln Arg Phe
            290                 295                 300

Ile Lys Glu Gly Gln Leu Ser Lys Gly Ala Lys Leu Tyr Val His Val
305                 310                 315                 320

Lys Gln Asn Leu Gly Arg Val Phe Ala Phe Ala Asp Glu Gln Gln Pro
                325                 330                 335

Leu Asn Trp Val Gln Thr His Asp Tyr Ser Asp Glu Leu Gly Thr Ile
                340                 345                 350

Leu Ser Ile Thr Ile Ala Arg Lys Glu Thr Ile Asp Val Asn Asp Arg
            355                 360                 365

Asp Ala Val Thr Arg Glu Val Gln Lys Met Phe Pro Gly Val Glu Val
            370                 375                 380

Leu Gly Thr Ala Ala Tyr Asp Trp Thr Ala Asp Pro Phe Ser Leu Gly
385                 390                 395                 400

Ala Trp Ala Ala Tyr Gly Val Gly Gln Leu Ser Arg Leu Lys Asp Leu
                405                 410                 415

Gln Ala Ala Glu Gly Arg Ile Leu Phe Ala Gly Ala Glu Thr Ser Asn
                420                 425                 430

Gly Trp His Ala Asn Ile Asp Gly Ala Val Glu Ser Gly Leu Arg Ala
            435                 440                 445

Gly Arg Glu Val Lys Gln Leu Leu Ser
450                 455

<210> SEQ ID NO 4
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Thr Gln Lys Thr Asn Arg Ala Ser Thr Val Lys Gly Gly Phe Asp Tyr
1               5                   10                  15

Asp Val Val Val Gly Gly Gly Phe Ala Gly Ala Thr Ala Ala Arg
                20                  25                  30

Glu Cys Gly Leu Gln Gly Tyr Arg Thr Leu Leu Glu Ala Arg Ser
            35                  40                  45

Arg Leu Gly Gly Arg Thr Phe Thr Ser Arg Phe Ala Gly Gln Glu Ile
            50                  55                  60

Glu Phe Gly Gly Ala Trp Val His Trp Leu Gln Pro His Val Trp Ala
65                  70                  75                  80

Glu Met Gln Arg Tyr Gly Leu Gly Val Val Glu Asp Pro Leu Thr Asn
```

85                  90                  95
Leu Asp Lys Thr Leu Ile Met Tyr Asn Asp Gly Ser Val Glu Ser Ile
                100                 105                 110

Ser Pro Asp Glu Phe Gly Lys Asn Ile Arg Ile Ala Phe Glu Lys Leu
            115                 120                 125

Cys His Asp Ala Trp Glu Val Phe Pro Arg Pro His Glu Pro Met Phe
        130                 135                 140

Thr Glu Arg Ala Arg Glu Leu Asp Lys Ser Ser Val Leu Asp Arg Ile
145                 150                 155                 160

Lys Thr Leu Gly Leu Ser Arg Leu Gln Gln Ala Gln Ile Asn Ser Tyr
                165                 170                 175

Met Ala Leu Tyr Ala Gly Glu Thr Thr Asp Lys Phe Gly Leu Pro Gly
                180                 185                 190

Val Leu Lys Leu Phe Ala Cys Gly Gly Trp Asn Tyr Asp Ala Phe Met
            195                 200                 205

Asp Thr Glu Thr His Tyr Arg Ile Gln Gly Gly Thr Ile Gly Leu Ile
        210                 215                 220

Asn Ala Met Leu Thr Asp Ser Gly Ala Glu Val Arg Met Ser Val Pro
225                 230                 235                 240

Val Thr Ala Val Glu Gln Val Asn Gly Gly Val Lys Ile Lys Thr Asp
                245                 250                 255

Asp Asp Glu Ile Ile Thr Ala Gly Val Val Met Thr Val Pro Leu
                260                 265                 270

Asn Thr Tyr Lys His Ile Gly Phe Thr Pro Ala Leu Ser Lys Gly Lys
            275                 280                 285

Gln Arg Phe Ile Lys Glu Gly Gln Leu Ser Lys Gly Ala Lys Leu Tyr
        290                 295                 300

Val His Val Lys Gln Asn Leu Gly Arg Val Phe Ala Phe Ala Asp Glu
305                 310                 315                 320

Gln Gln Pro Leu Asn Trp Val Gln Thr His Asp Tyr Ser Asp Glu Leu
                325                 330                 335

Gly Thr Ile Leu Ser Ile Thr Ile Ala Arg Lys Glu Thr Ile Asp Val
            340                 345                 350

Asn Asp Arg Asp Ala Val Thr Arg Glu Val Gln Lys Met Phe Pro Gly
        355                 360                 365

Val Glu Val Leu Gly Thr Ala Ala Tyr Asp Trp Thr Ala Asp Pro Phe
            370                 375                 380

Ser Leu Gly Ala Trp Ala Ala Tyr Gly Val Gly Gln Leu Ser Arg Leu
385                 390                 395                 400

Lys Asp Leu Gln Ala Ala Glu Gly Arg Ile Leu Phe Ala Gly Ala Glu
                405                 410                 415

Thr Ser Asn Gly Trp His Ala Asn Ile Asp Gly Ala Val Glu Ser Gly
                420                 425                 430

Leu Arg Ala Gly Arg Glu Val Lys Gln Leu Leu Ser
            435                 440

<210> SEQ ID NO 5
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Gln Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415
```

```
Val Glu Ser Gly Leu Arg Ala Gly Arg Glu Val Lys Gln Leu Leu Ser
            420                 425                 430
```

<210> SEQ ID NO 6
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
```

```
                    340                 345                 350
Met Phe Pro Gly Val Glu Val Leu Gly Thr Ala Ala Tyr Asp Trp Thr
                355                 360                 365

Ala Asp Pro Phe Ser Leu Gly Ala Glu Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 7
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270
```

```
Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Ser Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 8
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190
```

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Met Ala Ala Tyr Gly Val Gly Gln
        370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 9
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Ala Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His

```
                115                 120                 125
Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 10
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Gln Thr Phe Thr Ser Arg Phe Ala
            35                  40                  45
```

-continued

Gly Gln Glu Ile Glu Phe Gly Ala Trp Val His Trp Leu Gln Pro
 50                  55                  60

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 11
<211> LENGTH: 432
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 11

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu
                20                  25                  30

Glu Ala Arg Ser Arg Leu Gly Gly Phe Thr Phe Thr Ser Arg Phe Ala
                35                  40                  45

Gly Gln Glu Ile Glu Phe Gly Gly Ala Trp Val His Trp Leu Gln Pro
50                          55                      60

His Val Trp Ala Glu Met Gln Arg Tyr Gly Leu Gly Val Val Glu Asp
65                      70                      75                  80

Pro Leu Thr Asn Leu Asp Lys Thr Leu Ile Met Tyr Asn Asp Gly Ser
                    85                      90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe

```
            385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 12
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Gly Thr Phe Thr Ser Arg Phe Ala
                35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
                115                 120                 125

Glu Pro Met Phe Thr Glu Arg Ala Arg Glu Leu Asp Lys Ser Ser Val
            130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
                275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320
```

```
Ser Asp Glu Leu Gly Thr Ile Leu Ser Ile Thr Ile Ala Arg Lys Glu
            325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
            420                 425                 430

<210> SEQ ID NO 13
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Thr Thr Phe Thr Ser Arg Phe Ala
            35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
            165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240
```

```
Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 14
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Leu Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
```

```
                   165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 15
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Ser Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95
```

```
Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 16
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Phe Asp Tyr Asp Val Val Val Gly Gly Phe Ala Gly Ala
1               5                   10                  15
```

-continued

```
Thr Ala Ala Arg Glu Cys Gly Leu Gln Gly Tyr Arg Thr Leu Leu Leu
            20                  25                  30

Glu Ala Arg Ser Arg Leu Gly Gly Asn Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430
```

```
<210> SEQ ID NO 17
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17
```

Gly Phe Asp Tyr Asp Val Val Val Gly Gly Phe Ala Gly
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Gly His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

```
Ala Asp Pro Phe Ser Leu Gly Ala Trp Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 18
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gly Phe Asp Tyr Asp Val Val Val Gly Gly Phe Ala Gly Ala
1                5                  10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Leu His Tyr Arg Ile Gln Gly Gly Thr
    195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285
```

```
Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 19
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Arg His Tyr Arg Ile Gln Gly Gly Thr
        195                 200                 205

Ile Gly Leu Ile Asn Ala Met Leu Thr Asp Ser Gly Ala Glu Val Arg
```

```
                 210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                    245                 250                 255

Thr Val Pro Leu Asn Thr Tyr Lys His Ile Gly Phe Thr Pro Ala Leu
                    260                 265                 270

Ser Lys Gly Lys Gln Arg Phe Ile Lys Glu Gly Gln Leu Ser Lys Gly
                275                 280                 285

Ala Lys Leu Tyr Val His Val Lys Gln Asn Leu Gly Arg Val Phe Ala
                290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                    325                 330                 335

Thr Ile Asp Val Asn Asp Arg Asp Ala Val Thr Arg Glu Val Gln Lys
                    340                 345                 350

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
                370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                    405                 410                 415

Val Glu Ser Gly Leu Arg Ala Gly Arg Glu Val Lys Gln Leu Leu Ser
                420                 425                 430

<210> SEQ ID NO 20
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140
```

-continued

```
Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Val His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430
```

<210> SEQ ID NO 21
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60
```

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Pro Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 22
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Gly Phe Asp Tyr Asp Val Val Val Gly Gly Phe Ala Gly
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Ile Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415
```

```
Val Glu Ser Gly Leu Arg Ala Gly Arg Glu Val Lys Gln Leu Leu Ser
            420                 425                 430

<210> SEQ ID NO 23
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Val Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335
```

```
Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
            420                 425                 430
```

<210> SEQ ID NO 24
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 24

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
            130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
            165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
            245                 250                 255

Thr Val Pro Leu Asn Thr Tyr Lys His Ile Gly Phe Thr Pro Ala Leu
```

```
            260                 265                 270
Ser Lys Gly Lys Gln Arg Phe Ile Lys Glu Gly Gln Leu Ser Lys Gly
            275                 280                 285

Ala Asp Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 25
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190
```

-continued

```
Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
        210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
            245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Glu Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
            325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
        370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
            420                 425                 430
```

<210> SEQ ID NO 26
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
            100                 105                 110
```

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Lys Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 27
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala

```
                35                  40                  45
Gly Gln Glu Ile Glu Phe Gly Gly Ala Trp Val His Trp Leu Gln Pro
 50                  55                  60
His Val Trp Ala Glu Met Gln Arg Tyr Gly Leu Gly Val Val Glu Asp
 65                  70                  75                  80
Pro Leu Thr Asn Leu Asp Lys Thr Leu Ile Met Tyr Asn Asp Gly Ser
                 85                  90                  95
Val Glu Ser Ile Ser Pro Asp Glu Phe Gly Lys Asn Ile Arg Ile Ala
                100                 105                 110
Phe Glu Lys Leu Cys His Asp Ala Trp Glu Val Phe Pro Arg Pro His
                115                 120                 125
Glu Pro Met Phe Thr Glu Arg Ala Arg Glu Leu Asp Lys Ser Ser Val
            130                 135                 140
Leu Asp Arg Ile Lys Thr Leu Gly Leu Ser Arg Leu Gln Gln Ala Gln
145                 150                 155                 160
Ile Asn Ser Tyr Met Ala Leu Tyr Ala Gly Glu Thr Thr Asp Lys Phe
                165                 170                 175
Gly Leu Pro Gly Val Leu Lys Leu Phe Ala Cys Gly Gly Trp Asn Tyr
                180                 185                 190
Asp Ala Phe Met Asp Thr Glu Thr His Tyr Arg Ile Gln Gly Gly Thr
                195                 200                 205
Ile Gly Leu Ile Asn Ala Met Leu Thr Asp Ser Gly Ala Glu Val Arg
                210                 215                 220
Met Ser Val Pro Val Thr Ala Val Glu Gln Val Asn Gly Gly Val Lys
225                 230                 235                 240
Ile Lys Thr Asp Asp Asp Glu Ile Ile Thr Ala Gly Val Val Val Met
                245                 250                 255
Thr Val Pro Leu Asn Thr Tyr Lys His Ile Gly Phe Thr Pro Ala Leu
                260                 265                 270
Ser Lys Gly Lys Gln Arg Phe Ile Lys Glu Gly Gln Leu Ser Lys Gly
                275                 280                 285
Ala Lys Leu Tyr Val His Val Lys Gln Asn Leu Gly Arg Val Phe Ala
                290                 295                 300
Phe Ala Asp Glu Gln Gln Pro Leu Asn Trp Val Glu Thr His Asp Tyr
305                 310                 315                 320
Ser Asp Glu Leu Gly Thr Ile Leu Ser Ile Thr Ile Ala Arg Lys Glu
                325                 330                 335
Thr Ile Asp Val Asn Asp Arg Asp Ala Val Thr Arg Glu Val Gln Lys
                340                 345                 350
Met Phe Pro Gly Val Glu Val Leu Gly Thr Ala Ala Tyr Asp Trp Thr
            355                 360                 365
Ala Asp Pro Phe Ser Leu Gly Ala Trp Ala Ala Tyr Gly Val Gly Gln
            370                 375                 380
Leu Ser Arg Leu Lys Asp Leu Gln Ala Ala Glu Gly Arg Ile Leu Phe
385                 390                 395                 400
Ala Gly Ala Glu Thr Ser Asn Gly Trp His Ala Asn Ile Asp Gly Ala
                405                 410                 415
Val Glu Ser Gly Leu Arg Ala Gly Arg Glu Val Lys Gln Leu Leu Ser
                420                 425                 430

<210> SEQ ID NO 28
<211> LENGTH: 432
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 28

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Val Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
            370                 375                 380
```

```
Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
        420                 425                 430

<210> SEQ ID NO 29
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Leu Thr His Asp Tyr
```

```
                305                 310                 315                 320
Ser Asp Glu Leu Gly Thr Ile Leu Ser Ile Thr Ile Ala Arg Lys Glu
                    325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
                370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                    405                 410                 415

Val Glu Ser Gly Leu Arg Ala Gly Arg Glu Val Lys Gln Leu Leu Ser
                420                 425                 430

<210> SEQ ID NO 30
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
                115                 120                 125

Glu Pro Met Phe Thr Glu Arg Ala Arg Glu Leu Asp Lys Ser Ser Val
                130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
                210                 215                 220

Met Ser Val Pro Val Thr Ala Val Glu Gln Val Asn Gly Gly Val Lys
225                 230                 235                 240
```

-continued

```
Ile Lys Thr Asp Asp Asp Glu Ile Ile Thr Ala Gly Val Val Met
            245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Ile Thr His Asp Tyr
305                 310                 315                 320

Ser Asp Glu Leu Gly Thr Ile Leu Ser Ile Thr Ile Ala Arg Lys Glu
            325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
            420                 425                 430
```

<210> SEQ ID NO 31
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
            50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160
```

```
Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Tyr Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 32
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
```

85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Pro Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 33
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gly Phe Asp Tyr Asp Val Val Val Gly Gly Gly Phe Ala Gly Ala
1               5                   10                  15

```
Thr Ala Ala Arg Glu Cys Gly Leu Gln Gly Tyr Arg Thr Leu Leu
        20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
 50                  55                  60

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430
```

<210> SEQ ID NO 34
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Val Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
```

```
                355                 360                 365
Ala Asp Pro Phe Ser Leu Gly Ala Trp Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430

<210> SEQ ID NO 35
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
        210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285
```

```
Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Gln Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
        370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
                420                 425                 430
```

<210> SEQ ID NO 36  
<211> LENGTH: 432  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 36

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
        195                 200                 205
```

```
Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
            245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Asn Ile Ala Arg Lys Glu
            325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
            405                 410                 415

Val Glu Ser Gly Leu Arg Ala Gly Arg Glu Val Lys Gln Leu Leu Ser
            420                 425                 430

<210> SEQ ID NO 37
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
```

```
                130                 135                 140
Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Leu Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 38
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60
```

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Met Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 39
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Gly Phe Asp Tyr Asp Val Val Val Gly Gly Phe Ala Gly
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Leu Ile Asp Gly Ala
```

```
                        405                 410                 415
Val Glu Ser Gly Leu Arg Ala Gly Arg Glu Val Lys Gln Leu Leu Ser
                420                 425                 430

<210> SEQ ID NO 40
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335
```

```
Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
        370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Tyr Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 41
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
        210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255
```

```
Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Ser Ile Asp Gly Ala
                405                 410                 415

Val Glu Ser Gly Leu Arg Ala Gly Arg Glu Val Lys Gln Leu Leu Ser
            420                 425                 430
```

<210> SEQ ID NO 42
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
```

```
                180                 185                 190
Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
        210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
            245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
            325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
        370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Phe Ile Asp Gly Ala
            405                 410                 415

Val Glu Ser Gly Leu Arg Ala Gly Arg Glu Val Lys Gln Leu Leu Ser
            420                 425                 430

<210> SEQ ID NO 43
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
            100                 105                 110
```

```
Phe Glu Lys Leu Cys His Asp Ala Trp Glu Val Phe Pro Arg Pro His
        115                 120                 125
Glu Pro Met Phe Thr Glu Arg Ala Arg Glu Leu Asp Lys Ser Ser Val
    130                 135                 140
Leu Asp Arg Ile Lys Thr Leu Gly Leu Ser Arg Leu Gln Gln Ala Gln
145                 150                 155                 160
Ile Asn Ser Tyr Met Ala Leu Tyr Ala Gly Glu Thr Thr Asp Lys Phe
                165                 170                 175
Gly Leu Pro Gly Val Leu Lys Leu Phe Ala Cys Gly Gly Trp Asn Tyr
            180                 185                 190
Asp Ala Phe Met Asp Thr Glu Thr His Tyr Arg Ile Gln Gly Gly Thr
        195                 200                 205
Ile Gly Leu Ile Asn Ala Met Leu Thr Asp Ser Gly Ala Glu Val Arg
    210                 215                 220
Met Ser Val Pro Val Thr Ala Val Glu Gln Val Asn Gly Gly Val Lys
225                 230                 235                 240
Ile Lys Thr Asp Asp Glu Ile Ile Thr Ala Gly Val Val Val Met
                245                 250                 255
Thr Val Pro Leu Asn Thr Tyr Lys His Ile Gly Phe Thr Pro Ala Leu
            260                 265                 270
Ser Lys Gly Lys Gln Arg Phe Ile Lys Glu Gly Gln Leu Ser Lys Gly
        275                 280                 285
Ala Lys Leu Tyr Val His Val Lys Gln Asn Leu Gly Arg Val Phe Ala
    290                 295                 300
Phe Ala Asp Glu Gln Pro Leu Asn Trp Gln Thr His Asp Tyr
305                 310                 315                 320
Ser Asp Glu Leu Gly Thr Ile Leu Ser Ile Thr Ile Ala Arg Lys Glu
                325                 330                 335
Thr Ile Asp Val Asn Asp Arg Asp Ala Val Thr Arg Glu Val Gln Lys
            340                 345                 350
Met Phe Pro Gly Val Glu Val Leu Gly Thr Ala Ala Tyr Asp Trp Thr
        355                 360                 365
Ala Asp Pro Phe Ser Leu Gly Ala Trp Ala Ala Tyr Gly Val Gly Gln
    370                 375                 380
Leu Ser Arg Leu Lys Asp Leu Gln Ala Ala Glu Gly Arg Ile Leu Phe
385                 390                 395                 400
Ala Gly Ala Glu Thr Ser Asn Gly Trp His Ala Gly Ile Asp Gly Ala
                405                 410                 415
Val Glu Ser Gly Leu Arg Ala Gly Arg Glu Val Lys Gln Leu Leu Ser
            420                 425                 430

<210> SEQ ID NO 44
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gly Phe Asp Tyr Asp Val Val Val Gly Gly Gly Phe Ala Gly Ala
1               5                   10                  15
Thr Ala Ala Arg Glu Cys Gly Leu Gln Gly Tyr Arg Thr Leu Leu Leu
            20                  25                  30
```

Glu Ala Arg Ser Arg Leu Gly Arg Thr Phe Thr Ser Arg Phe Ala
             35                  40                  45

Gly Gln Glu Ile Glu Phe Gly Gly Ala Trp Val His Trp Leu Gln Pro
 50                  55                  60

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
            290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Glu Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 45
<211> LENGTH: 432
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380
```

```
Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Ala Ile Asp Gly Ala
            405                 410                 415

Val Glu Ser Gly Leu Arg Ala Gly Arg Glu Val Lys Gln Leu Leu Ser
            420                 425                 430
```

<210> SEQ ID NO 46
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 46

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300
```

```
Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Phe Asp Gly Ala
                405                 410                 415

Val Glu Ser Gly Leu Arg Ala Gly Arg Glu Val Lys Gln Leu Leu Ser
            420                 425                 430
```

<210> SEQ ID NO 47
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
```

```
                225                 230                 235                 240

Ile Lys Thr Asp Asp Glu Ile Ile Thr Ala Gly Val Val Met
                        245                 250                 255

Thr Val Pro Leu Asn Thr Tyr Lys His Ile Gly Phe Thr Pro Ala Leu
                        260                 265                 270

Ser Lys Gly Lys Gln Arg Phe Ile Lys Glu Gly Gln Leu Ser Lys Gly
                        275                 280                 285

Ala Lys Leu Tyr Val His Val Lys Gln Asn Leu Gly Arg Val Phe Ala
                        290                 295                 300

Phe Ala Asp Glu Gln Gln Pro Leu Asn Trp Val Gln Thr His Asp Tyr
        305                 310                 315                 320

Ser Asp Glu Leu Gly Thr Ile Leu Ser Ile Thr Ile Ala Arg Lys Glu
                        325                 330                 335

Thr Ile Asp Val Asn Asp Arg Asp Ala Val Thr Arg Glu Val Gln Lys
                        340                 345                 350

Met Phe Pro Gly Val Glu Val Leu Gly Thr Ala Ala Tyr Asp Trp Thr
                        355                 360                 365

Ala Asp Pro Phe Ser Leu Gly Ala Trp Ala Ala Tyr Gly Val Gly Gln
                        370                 375                 380

Leu Ser Arg Leu Lys Asp Leu Gln Ala Ala Glu Gly Arg Ile Leu Phe
        385                 390                 395                 400

Ala Gly Ala Glu Thr Ser Asn Gly Trp His Ala Asn Tyr Asp Gly Ala
                        405                 410                 415

Val Glu Ser Gly Leu Arg Ala Gly Arg Glu Val Lys Gln Leu Leu Ser
                        420                 425                 430

<210> SEQ ID NO 48
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
                115                 120                 125

Glu Pro Met Phe Thr Glu Arg Ala Arg Glu Leu Asp Lys Ser Ser Val
                130                 135                 140

Leu Asp Arg Ile Lys Thr Leu Gly Leu Ser Arg Leu Gln Gln Ala Gln
145                 150                 155                 160
```

Ile Asn Ser Tyr Met Ala Leu Tyr Ala Gly Glu Thr Thr Asp Lys Phe
            165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ile Asn Ala Met Leu Thr Asp Ser Gly Ala Glu Val Arg
            210                 215                 220

Met Ser Val Pro Val Thr Ala Val Glu Gln Val Asn Gly Val Lys
225                 230                 235                 240

Ile Lys Thr Asp Asp Glu Ile Ile Thr Ala Gly Val Val Val Met
                    245                 250                 255

Thr Val Pro Leu Asn Thr Tyr Lys His Ile Gly Phe Thr Pro Ala Leu
                    260                 265                 270

Ser Lys Gly Lys Gln Arg Phe Ile Lys Glu Gly Gln Leu Ser Lys Gly
                    275                 280                 285

Ala Lys Leu Tyr Val His Val Lys Gln Asn Leu Gly Arg Val Phe Ala
                    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                    325                 330                 335

Thr Ile Asp Val Asn Asp Arg Asp Ala Val Thr Arg Glu Val Gln Lys
                    340                 345                 350

Met Phe Pro Gly Val Glu Val Leu Gly Thr Ala Ala Tyr Asp Trp Thr
                    355                 360                 365

Ala Asp Pro Phe Ser Leu Gly Ala Trp Ala Ala Tyr Gly Val Gly Gln
                    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ala Asp Gly Ala
                    405                 410                 415

Val Glu Ser Gly Leu Arg Ala Gly Arg Glu Val Lys Gln Leu Leu Ser
                    420                 425                 430

<210> SEQ ID NO 49
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                    20                  25                  30

Glu Ala Arg Ser Arg Leu Gly Gly Arg Thr Phe Thr Ser Arg Phe Ala
                    35                  40                  45

Gly Gln Glu Ile Glu Phe Gly Gly Ala Trp Val His Trp Leu Gln Pro
                    50                  55                  60

His Val Trp Ala Glu Met Gln Arg Tyr Gly Leu Gly Val Val Glu Asp
65                  70                  75                  80

```
Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Val Asp Gly Ala
                405                 410                 415

Val Glu Ser Gly Leu Arg Ala Gly Arg Glu Val Lys Gln Leu Leu Ser
            420                 425                 430

<210> SEQ ID NO 50
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gly Phe Asp Tyr Asp Val Val Val Val Gly Gly Gly Phe Ala Gly Ala
```

```
1               5                   10                  15
Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
                50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
                115                 120                 125

Glu Pro Met Phe Thr Glu Arg Ala Arg Glu Leu Asp Lys Ser Ser Val
                130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
                210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
                275                 280                 285

Ala Lys Leu Tyr Val His Val Lys Gln Asn Leu Gly Arg Val Phe Ala
                290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
                370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Leu Asp Gly Ala
                405                 410                 415

Val Glu Ser Gly Leu Arg Ala Gly Arg Glu Val Lys Gln Leu Leu Ser
                420                 425                 430
```

<210> SEQ ID NO 51
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Gly Arg Thr Phe Thr Ser Arg Phe Ala
        35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Gln Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350
```

Met Phe Pro Gly Val Glu Val Leu Gly Thr Ala Ala Tyr Asp Trp Thr
                355                 360                 365

Ala Asp Pro Phe Ser Leu Gly Ala Trp Ala Ala Tyr Gly Val Gly Gln
            370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 52
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
            20                  25                  30

Glu Ala Arg Ser Arg Leu Gly Arg Thr Phe Thr Ser Arg Phe Ala
            35                  40                  45

Gly Gln Glu Ile Glu Phe Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Gly Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
    195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly

```
                275                 280                 285
Ala Lys Leu Tyr Val His Val Lys Gln Asn Leu Gly Arg Val Phe Ala
        290                 295                 300
Phe Ala Asp Glu Gln Gln Pro Leu Asn Trp Val Gln Thr His Asp Tyr
305                 310                 315                 320
Ser Asp Glu Leu Gly Thr Ile Leu Ser Ile Thr Ile Ala Arg Lys Glu
                325                 330                 335
Thr Ile Asp Val Asn Asp Arg Asp Ala Val Thr Arg Glu Val Gln Lys
                340                 345                 350
Met Phe Pro Gly Val Glu Val Leu Gly Thr Ala Ala Tyr Asp Trp Thr
                355                 360                 365
Ala Asp Pro Phe Ser Leu Gly Ala Trp Ala Ala Tyr Gly Val Gly Gln
        370                 375                 380
Leu Ser Arg Leu Lys Asp Leu Gln Ala Ala Glu Gly Arg Ile Leu Phe
385                 390                 395                 400
Ala Gly Ala Glu Thr Ser Asn Gly Trp His Ala Asn Ile Asp Gly Ala
                405                 410                 415
Val Glu Ser Gly Leu Arg Ala Gly Arg Glu Val Lys Gln Leu Leu Ser
                420                 425                 430

<210> SEQ ID NO 53
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160

Ile Asn Ser Tyr Met Ala Glu Tyr Ala Gly Glu Thr Thr Asp Lys Phe
                165                 170                 175

Gly Leu Pro Gly Val Leu Lys Leu Phe Ala Cys Gly Gly Trp Asn Tyr
                180                 185                 190

Asp Ala Phe Met Asp Thr Glu Thr His Tyr Arg Ile Gln Gly Gly Thr
            195                 200                 205
```

```
Ile Gly Leu Ile Asn Ala Met Leu Thr Asp Ser Gly Ala Glu Val Arg
    210                 215                 220
Met Ser Val Pro Val Thr Ala Val Glu Gln Val Asn Gly Gly Val Lys
225                 230                 235                 240
Ile Lys Thr Asp Asp Asp Glu Ile Ile Thr Ala Gly Val Val Val Met
                245                 250                 255
Thr Val Pro Leu Asn Thr Tyr Lys His Ile Gly Phe Thr Pro Ala Leu
            260                 265                 270
Ser Lys Gly Lys Gln Arg Phe Ile Lys Glu Gly Gln Leu Ser Lys Gly
        275                 280                 285
Ala Lys Leu Tyr Val His Val Lys Gln Asn Leu Gly Arg Val Phe Ala
    290                 295                 300
Phe Ala Asp Glu Gln Gln Pro Leu Asn Trp Val Gln Thr His Asp Tyr
305                 310                 315                 320
Ser Asp Glu Leu Gly Thr Ile Leu Ser Ile Thr Ile Ala Arg Lys Glu
                325                 330                 335
Thr Ile Asp Val Asn Asp Arg Asp Ala Val Thr Arg Glu Val Gln Lys
            340                 345                 350
Met Phe Pro Gly Val Glu Val Leu Gly Thr Ala Ala Tyr Asp Trp Thr
        355                 360                 365
Ala Asp Pro Phe Ser Leu Gly Ala Trp Ala Ala Tyr Gly Val Gly Gln
    370                 375                 380
Leu Ser Arg Leu Lys Asp Leu Gln Ala Ala Glu Gly Arg Ile Leu Phe
385                 390                 395                 400
Ala Gly Ala Glu Thr Ser Asn Gly Trp His Ala Asn Ile Asp Gly Ala
                405                 410                 415
Val Glu Ser Gly Leu Arg Ala Gly Arg Glu Val Lys Gln Leu Leu Ser
            420                 425                 430

<210> SEQ ID NO 54
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gly Phe Asp Tyr Asp Val Val Val Gly Gly Phe Ala Gly Ala
1               5                   10                  15
Thr Ala Ala Arg Glu Cys Gly Leu Gln Gly Tyr Arg Thr Leu Leu Leu
                20                  25                  30
Glu Ala Arg Ser Arg Leu Gly Gly Arg Thr Phe Thr Ser Arg Phe Ala
            35                  40                  45
Gly Gln Glu Ile Glu Phe Gly Gly Ala Trp Val His Trp Leu Gln Pro
        50                  55                  60
His Val Trp Ala Glu Met Gln Arg Tyr Gly Leu Gly Val Val Glu Asp
65                  70                  75                  80
Pro Leu Thr Asn Leu Asp Lys Thr Leu Ile Met Tyr Asn Asp Gly Ser
                85                  90                  95
Val Glu Ser Ile Ser Pro Asp Glu Phe Gly Lys Asn Ile Arg Ile Ala
            100                 105                 110
Phe Glu Lys Leu Cys His Asp Ala Trp Glu Val Phe Pro Arg Pro His
        115                 120                 125
```

```
Glu Pro Met Phe Thr Glu Arg Ala Arg Glu Leu Asp Lys Ser Ser Val
            130                 135                 140

Leu Asp Arg Ile Lys Thr Leu Gly Leu Ser Arg Leu Gln Gln Ala Gln
145                 150                 155                 160

Ile Asn Ser Tyr Met Ala Ile Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
                195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 55
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
```

```
            50                  55                  60
His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Cys Tyr Ala Gly Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 56
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 56

```
Gly Phe Asp Tyr Asp Val Val Val Gly Gly Phe Ala Gly Ala
 1               5                  10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
                35                  40                  45

Gly Gln Glu Ile Glu Phe Gly Gly Ala Trp Val His Trp Leu Gln Pro
    50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Ser Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400
```

```
Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 57
<211> LENGTH: 477
<212> TYPE: PRT
<213> ORGANISM: Pseudomonas sp. HZN6

<400> SEQUENCE: 57

Met Asp Glu Lys Arg Asn Asn Gly Leu Ser Arg Arg Ser Phe Ile Gly
1               5                   10                  15

Gly Ala Ala Val Val Thr Ala Gly Ala Gly Leu Gly Leu Ile Gly
            20                  25                  30

Ser Ala Asn Ala Thr Glu Asn Gly Thr Ser Lys Arg Ala Thr Gly Phe
        35                  40                  45

Asp Tyr Asp Val Ile Val Gly Gly Phe Ala Gly Ala Thr Ala
50                  55                  60

Ala Arg Glu Cys Gly His Gln Gly Tyr Lys Thr Leu Leu Leu Glu Ala
65              70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
            100                 105                 110

Trp Ser Glu Met Gln Arg Tyr Gly Leu Gly Val Val Glu Asp Pro Leu
        115                 120                 125

Thr Asn Leu Asp Lys Thr Leu Val Met Tyr Asn Asp Gly Ser Val Glu
    130                 135                 140

Asp Leu Pro Pro Glu Val Phe Gly Thr Asn Ile Gln Val Ala Phe Glu
145                 150                 155                 160

Lys Met Cys His Asp Ala Trp Glu Ala Phe Pro Arg Pro His Glu Pro
                165                 170                 175

Met Phe Thr Glu Arg Ala Arg Lys Leu Asp Lys Met Ser Val Leu Asp
            180                 185                 190

Arg Ile Asn Gln Leu Glu Leu Thr Arg Ala Gln Arg Ala Glu Leu Asn
        195                 200                 205

Ser Tyr Met Ala Leu Tyr Gly Gly Glu Thr Thr Asp Lys Tyr Gly Leu
    210                 215                 220

Pro Gly Val Leu Lys Leu Phe Ala Cys Gly Gly Trp Asn Tyr Asn Ala
225                 230                 235                 240

Phe Met Asp Thr Glu Thr His Tyr Arg Ile Glu Gly Thr Ile Gly
                245                 250                 255

Leu Ile Asn Ala Met Leu Ala Asp Ser Gly Ala Glu Val Arg Leu Asn
            260                 265                 270

Met Pro Val Ile Ser Val Glu Gln Leu Asn Gly Gly Val Arg Val Glu
        275                 280                 285

Thr Asp Asp Gly Glu Thr Ile Thr Ala Gly Thr Ile Ile Met Thr Val
    290                 295                 300

Pro Leu Asn Thr Tyr Arg His Ile Asn Phe Thr Pro Ala Leu Ser Glu
305                 310                 315                 320

Gly Lys Gln Arg Phe Ile Gln Glu Gly Gln Leu Ser Lys Gly Ala Lys
                325                 330                 335

Leu Tyr Val His Val Lys Glu Asn Leu Gly Arg Val Phe Ala Phe Ala
            340                 345                 350
```

```
Asp Glu Gln Gln Pro Leu Asn Trp Val Gln Thr His Asp Tyr Gly Asp
            355                 360                 365

Glu Leu Gly Thr Ile Leu Ser Ile Thr Ile Ala Arg Ala Glu Thr Ile
    370                 375                 380

Asp Val Asn Asp Arg Asp Ala Val Thr Arg Glu Ile Arg Lys Leu Phe
385                 390                 395                 400

Pro Gly Val Glu Val Leu Gly Ile Ala Ala Tyr Asp Trp Thr Ala Asp
                405                 410                 415

Pro Phe Ser Leu Gly Ala Trp Ala Ala Tyr Gly Val Gly Gln Leu Ser
            420                 425                 430

Arg Leu Thr Asp Leu Gln Gln Pro Glu Gly Arg Ile Leu Phe Ala Gly
            435                 440                 445

Ala Glu Thr Ser Asn Gly Trp His Ala Asn Ile Asp Gly Ala Val Glu
            450                 455                 460

Ser Gly Leu Arg Ala Gly Arg Glu Ala Lys Glu Ile Leu
465                 470                 475

<210> SEQ ID NO 58
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Asp Glu Lys Arg Asn Asn Gly Leu Ser Arg Ser Phe Ile Gly
1               5                   10                  15

Gly Ala Ala Val Val Thr Ala Gly Ala Ala Gly Leu Gly Leu Ile Gly
                20                  25                  30

Ser Ala Asn Ala Thr Glu Asn Gly Thr Ser Lys Arg Ala Thr Gly Phe
            35                  40                  45

Asp Tyr Asp Val Ile Val Gly Gly Gly Phe Ala Gly Ala Thr Ala
    50                  55                  60

Ala Arg Glu Cys Gly His Gln Gly Tyr Lys Thr Leu Leu Leu Glu Ala
65                  70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
            100                 105                 110

Trp Ser Glu Met Gln Arg Tyr Gly Leu Gly Val Val Glu Asp Pro Leu
        115                 120                 125

Thr Asn Leu Asp Lys Thr Leu Val Met Tyr Asn Asp Gly Ser Val Glu
    130                 135                 140

Asp Leu Pro Pro Glu Val Phe Gly Thr Asn Ile Gln Val Ala Phe Glu
145                 150                 155                 160

Lys Met Cys His Asp Ala Trp Glu Ala Phe Pro Arg Pro His Glu Pro
                165                 170                 175

Met Phe Thr Glu Arg Ala Arg Lys Leu Asp Lys Met Ser Val Leu Asp
            180                 185                 190

Arg Ile Asn Gln Leu Glu Leu Thr Arg Ala Gln Arg Ala Glu Leu Asn
        195                 200                 205

Ser Tyr Met Ala Leu Tyr Gly Gly Glu Thr Thr Asp Lys Tyr Gly Leu
    210                 215                 220
```

```
Pro Gly Val Leu Lys Leu Phe Ala Cys Gly Gly Trp Asn Tyr Asn Ala
225                 230                 235                 240

Phe Met Asp Thr Glu Thr His Tyr Arg Ile Glu Gly Gly Thr Ile Gly
            245                 250                 255

Leu Ile Asn Ala Met Leu Ala Asp Ser Gly Ala Glu Val Arg Leu Asn
            260                 265                 270

Met Pro Val Ile Ser Val Glu Gln Leu Asn Gly Gly Val Arg Val Glu
        275                 280                 285

Thr Asp Asp Gly Glu Thr Ile Thr Ala Gly Thr Ile Met Thr Val
    290                 295                 300

Pro Leu Asn Thr Tyr Arg His Ile Asn Phe Thr Pro Ala Leu Ser Glu
305                 310                 315                 320

Gly Lys Gln Arg Phe Ile Gln Glu Gly Gln Leu Ser Lys Gly Ala Lys
                325                 330                 335

Leu Tyr Val His Val Lys Glu Asn Leu Gly Arg Val Phe Ala Phe Ala
            340                 345                 350

Asp Glu Gln Gln Pro Leu Asn Trp Val Gln Thr His Asp Tyr Gly Asp
            355                 360                 365

Glu Leu Gly Thr Ile Leu Ser Ile Thr Ile Ala Arg Ala Glu Thr Ile
    370                 375                 380

Asp Val Asn Asp Arg Asp Ala Val Thr Arg Glu Ile Arg Lys Leu Phe
385                 390                 395                 400

Pro Gly Val Glu Val Leu Gly Ile Ala Ala Tyr Asp Trp Thr Ala Asp
                405                 410                 415

Pro Phe Ser Leu Gly Ala Ala Ala Tyr Gly Val Gly Gln Leu Ser
            420                 425                 430

Arg Leu Thr Asp Leu Gln Gln Pro Glu Gly Arg Ile Leu Phe Ala Gly
            435                 440                 445

Ala Glu Thr Ser Asn Gly Trp His Ala Asn Ile Asp Gly Ala Val Glu
        450                 455                 460

Ser Gly Leu Arg Ala Gly Arg Glu Ala Lys Glu Ile Leu
465                 470                 475

<210> SEQ ID NO 59
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Met Asp Glu Lys Arg Asn Asn Gly Leu Ser Arg Arg Ser Phe Ile Gly
1               5                   10                  15

Gly Ala Ala Val Val Thr Ala Gly Ala Ala Gly Leu Gly Leu Ile Gly
                20                  25                  30

Ser Ala Asn Ala Thr Glu Asn Gly Thr Ser Lys Arg Ala Thr Gly Phe
            35                  40                  45

Asp Tyr Asp Val Ile Val Val Gly Gly Gly Phe Ala Gly Ala Thr Ala
        50                  55                  60

Ala Arg Glu Cys Gly His Gln Gly Tyr Lys Thr Leu Leu Leu Glu Ala
65                  70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
```

100                 105                 110
    Trp Ser Glu Met Gln Arg Tyr Gly Leu Gly Val Val Glu Asp Pro Leu
            115                 120                 125
    Thr Asn Leu Asp Lys Thr Leu Val Met Tyr Asn Asp Gly Ser Val Glu
        130                 135                 140
    Asp Leu Pro Pro Glu Val Phe Gly Thr Asn Ile Gln Val Ala Phe Glu
    145                 150                 155                 160
    Lys Met Cys His Asp Ala Trp Glu Ala Phe Pro Arg Pro His Glu Pro
                    165                 170                 175
    Met Phe Thr Glu Arg Ala Arg Lys Leu Asp Lys Met Ser Val Leu Asp
                180                 185                 190
    Arg Ile Asn Gln Leu Glu Leu Thr Arg Ala Gln Arg Ala Glu Leu Asn
                195                 200                 205
    Ser Tyr Met Ala Leu Tyr Gly Gly Glu Thr Thr Asp Lys Tyr Gly Leu
        210                 215                 220
    Pro Gly Val Leu Lys Leu Phe Ala Cys Gly Gly Trp Asn Tyr Asn Ala
    225                 230                 235                 240
    Phe Met Asp Thr Glu Thr His Tyr Arg Ile Glu Gly Gly Thr Ile Gly
                    245                 250                 255
    Leu Ile Asn Ala Met Leu Ala Asp Ser Gly Ala Glu Val Arg Leu Asn
                260                 265                 270
    Met Pro Val Ile Ser Val Glu Gln Leu Asn Gly Val Arg Val Glu
                275                 280                 285
    Thr Asp Asp Gly Glu Thr Ile Thr Ala Gly Thr Ile Met Thr Val
        290                 295                 300
    Pro Leu Asn Thr Tyr Arg His Ile Asn Phe Thr Pro Ala Leu Ser Glu
    305                 310                 315                 320
    Gly Lys Gln Arg Phe Ile Gln Glu Gly Gln Leu Ser Lys Gly Ala Lys
                    325                 330                 335
    Leu Tyr Val His Val Lys Glu Asn Leu Gly Arg Val Phe Ala Phe Ala
                340                 345                 350
    Asp Glu Gln Gln Pro Leu Asn Trp Val Gln Thr His Asp Tyr Gly Asp
                355                 360                 365
    Glu Leu Gly Thr Ile Leu Ser Ile Thr Ile Ala Arg Ala Glu Thr Ile
        370                 375                 380
    Asp Val Asn Asp Arg Asp Ala Val Thr Arg Glu Ile Arg Lys Leu Phe
    385                 390                 395                 400
    Pro Gly Val Glu Val Leu Gly Ile Ala Ala Tyr Asp Trp Thr Ala Asp
                    405                 410                 415
    Pro Phe Ser Leu Gly Ala Ser Ala Ala Tyr Gly Val Gly Gln Leu Ser
                420                 425                 430
    Arg Leu Thr Asp Leu Gln Gln Pro Glu Gly Arg Ile Leu Phe Ala Gly
                435                 440                 445
    Ala Glu Thr Ser Asn Gly Trp His Ala Asn Ile Asp Gly Ala Val Glu
        450                 455                 460
    Ser Gly Leu Arg Ala Gly Arg Glu Ala Lys Glu Ile Leu
    465                 470                 475

<210> SEQ ID NO 60
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 60

| | | | | | | | | | | | | | | | |
|---|---|---|---|---|---|---|---|---|---|---|---|---|---|---|---|

Met Asp Glu Lys Arg Asn Asn Gly Leu Ser Arg Arg Ser Phe Ile Gly
1               5                   10                  15

Gly Ala Ala Val Val Thr Ala Gly Ala Ala Gly Leu Gly Leu Ile Gly
            20                  25                  30

Ser Ala Asn Ala Thr Glu Asn Gly Thr Ser Lys Arg Ala Thr Gly Phe
        35                  40                  45

Asp Tyr Asp Val Ile Val Gly Gly Phe Ala Gly Ala Thr Ala
    50                  55                  60

Ala Arg Glu Cys Gly His Gln Gly Tyr Lys Thr Leu Leu Leu Glu Ala
65                  70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
            100                 105                 110

Trp Ser Glu Met Gln Arg Tyr Gly Leu Gly Val Val Glu Asp Pro Leu
            115                 120                 125

Thr Asn Leu Asp Lys Thr Leu Val Met Tyr Asn Asp Gly Ser Val Glu
        130                 135                 140

Asp Leu Pro Pro Glu Val Phe Gly Thr Asn Ile Gln Val Ala Phe Glu
145                 150                 155                 160

Lys Met Cys His Asp Ala Trp Glu Ala Phe Pro Arg Pro His Glu Pro
                165                 170                 175

Met Phe Thr Glu Arg Ala Arg Lys Leu Asp Lys Met Ser Val Leu Asp
            180                 185                 190

Arg Ile Asn Gln Leu Glu Leu Thr Arg Ala Gln Arg Ala Glu Leu Asn
        195                 200                 205

Ser Tyr Met Ala Leu Tyr Gly Gly Thr Thr Asp Lys Tyr Gly Leu
    210                 215                 220

Pro Gly Val Leu Lys Leu Phe Ala Cys Gly Gly Trp Asn Tyr Asn Ala
225                 230                 235                 240

Phe Met Asp Thr Glu Thr His Tyr Arg Ile Glu Gly Gly Thr Ile Gly
                245                 250                 255

Leu Ile Asn Ala Met Leu Ala Asp Ser Gly Ala Glu Val Arg Leu Asn
            260                 265                 270

Met Pro Val Ile Ser Val Glu Gln Leu Asn Gly Gly Val Arg Val Glu
        275                 280                 285

Thr Asp Asp Gly Glu Thr Ile Thr Ala Gly Thr Ile Met Thr Val
    290                 295                 300

Pro Leu Asn Thr Tyr Arg His Ile Asn Phe Thr Pro Ala Leu Ser Glu
305                 310                 315                 320

Gly Lys Gln Arg Phe Ile Gln Glu Gly Gln Leu Ser Lys Gly Ala Lys
                325                 330                 335

Leu Tyr Val His Val Lys Glu Asn Leu Gly Arg Val Phe Ala Phe Ala
            340                 345                 350

Asp Glu Gln Gln Pro Leu Asn Trp Val Gln Thr His Asp Tyr Gly Asp
        355                 360                 365

Glu Leu Gly Thr Ile Leu Ser Ile Thr Ile Ala Arg Ala Glu Thr Ile
    370                 375                 380

Asp Val Asn Asp Arg Asp Ala Val Thr Arg Glu Ile Arg Lys Leu Phe
385                 390                 395                 400

```
Pro Gly Val Glu Val Leu Gly Ile Ala Ala Tyr Asp Trp Thr Ala Asp
                405                 410                 415

Pro Phe Ser Leu Gly Ala Glu Ala Ala Tyr Gly Val Gly Gln Leu Ser
            420                 425                 430

Arg Leu Thr Asp Leu Gln Gln Pro Glu Gly Arg Ile Leu Phe Ala Gly
        435                 440                 445

Ala Glu Thr Ser Asn Gly Trp His Ala Asn Ile Asp Gly Ala Val Glu
450                 455                 460

Ser Gly Leu Arg Ala Gly Arg Glu Ala Lys Glu Ile Leu
465                 470                 475

<210> SEQ ID NO 61
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Asp Glu Lys Arg Asn Asn Gly Leu Ser Arg Arg Ser Phe Ile Gly
1               5                   10                  15

Gly Ala Ala Val Val Thr Ala Gly Ala Ala Gly Leu Gly Leu Ile Gly
                20                  25                  30

Ser Ala Asn Ala Thr Glu Asn Gly Thr Ser Lys Arg Ala Thr Gly Phe
            35                  40                  45

Asp Tyr Asp Val Ile Val Val Gly Gly Gly Phe Ala Gly Ala Thr Ala
        50                  55                  60

Ala Arg Glu Cys Gly His Gln Gly Tyr Lys Thr Leu Leu Glu Ala
65                  70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
                100                 105                 110

Trp Ser Glu Met Gln Arg Tyr Gly Leu Gly Val Val Glu Asp Pro Leu
            115                 120                 125

Thr Asn Leu Asp Lys Thr Leu Val Met Tyr Asn Asp Gly Ser Val Glu
        130                 135                 140

Asp Leu Pro Pro Glu Val Phe Gly Thr Asn Ile Gln Val Ala Phe Glu
145                 150                 155                 160

Lys Met Cys His Asp Ala Trp Glu Ala Phe Pro Arg Pro His Glu Pro
                165                 170                 175

Met Phe Thr Glu Arg Ala Arg Lys Leu Asp Lys Met Ser Val Leu Asp
            180                 185                 190

Arg Ile Asn Gln Leu Glu Leu Thr Arg Ala Gln Arg Ala Glu Leu Asn
        195                 200                 205

Ser Tyr Met Ala Leu Tyr Gly Gly Glu Thr Thr Asp Lys Tyr Gly Leu
210                 215                 220

Pro Gly Val Leu Lys Leu Phe Ala Cys Gly Gly Trp Asn Tyr Asn Ala
225                 230                 235                 240

Phe Met Asp Thr Glu Thr His Tyr Arg Ile Glu Gly Gly Thr Ile Gly
                245                 250                 255

Leu Ile Asn Ala Met Leu Ala Asp Ser Gly Ala Glu Val Arg Leu Asn
            260                 265                 270

Met Pro Val Ile Ser Val Glu Gln Leu Asn Gly Gly Val Arg Val Glu
```

```
            275                 280                 285

Thr Asp Asp Gly Glu Thr Ile Thr Ala Gly Thr Ile Met Thr Val
    290                 295                 300

Pro Leu Asn Thr Tyr Arg His Ile Asn Phe Thr Pro Ala Leu Ser Glu
305                 310                 315                 320

Gly Lys Gln Arg Phe Ile Gln Glu Gly Gln Leu Ser Lys Gly Ala Lys
                325                 330                 335

Leu Tyr Val His Val Lys Glu Asn Leu Gly Arg Val Phe Ala Phe Ala
                340                 345                 350

Asp Glu Gln Gln Pro Leu Asn Trp Val Gln Thr His Asp Tyr Gly Asp
                355                 360                 365

Glu Leu Gly Thr Ile Leu Ser Ile Thr Ile Ala Arg Ala Glu Thr Ile
            370                 375                 380

Asp Val Asn Asp Arg Asp Ala Val Thr Arg Glu Ile Arg Lys Leu Phe
385                 390                 395                 400

Pro Gly Val Glu Val Leu Gly Ile Ala Ala Tyr Asp Trp Thr Ala Asp
                405                 410                 415

Pro Phe Ser Leu Gly Ala His Ala Ala Tyr Gly Val Gly Gln Leu Ser
                420                 425                 430

Arg Leu Thr Asp Leu Gln Gln Pro Glu Gly Arg Ile Leu Phe Ala Gly
                435                 440                 445

Ala Glu Thr Ser Asn Gly Trp His Ala Asn Ile Asp Gly Ala Val Glu
                450                 455                 460

Ser Gly Leu Arg Ala Gly Arg Glu Ala Lys Glu Ile Leu
465                 470                 475

<210> SEQ ID NO 62
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
                100                 105                 110

Phe Glu Lys Leu Cys His Asp Ala Trp Glu Val Phe Pro Arg Pro His
            115                 120                 125

Glu Pro Met Phe Thr Glu Arg Ala Arg Glu Leu Asp Lys Ser Ser Val
        130                 135                 140

Leu Asp Arg Ile Lys Thr Leu Gly Leu Ser Arg Leu Gln Gln Ala Gln
145                 150                 155                 160
```

```
Ile Asn Ser Tyr Met Ala Leu Tyr Ala Gly Glu Thr Thr Asp Lys Phe
            165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
            195                 200                 205

Ile Gly Leu Ala Asn Ala Met Leu Thr Asp Ser Gly Ala Glu Val Arg
            210                 215                 220

Met Ser Val Pro Val Thr Ala Val Glu Gln Val Asn Gly Val Lys
225                 230                 235                 240

Ile Lys Thr Asp Asp Asp Glu Ile Ile Thr Ala Gly Val Val Val Met
                    245                 250                 255

Thr Val Pro Leu Asn Thr Tyr Lys His Ile Gly Phe Thr Pro Ala Leu
                    260                 265                 270

Ser Lys Gly Lys Gln Arg Phe Ile Lys Glu Gly Gln Leu Ser Lys Gly
                    275                 280                 285

Ala Lys Leu Tyr Val His Val Lys Gln Asn Leu Gly Arg Val Phe Ala
                    290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                    325                 330                 335

Thr Ile Asp Val Asn Asp Arg Asp Ala Val Thr Arg Glu Val Gln Lys
                    340                 345                 350

Met Phe Pro Gly Val Glu Val Leu Gly Thr Ala Ala Tyr Asp Trp Thr
                    355                 360                 365

Ala Asp Pro Phe Ser Leu Gly Ala Gln Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                    405                 410                 415

Val Glu Ser Gly Leu Arg Ala Gly Arg Glu Val Lys Gln Leu Leu Ser
                    420                 425                 430

<210> SEQ ID NO 63
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Ala Trp Val His Trp Leu Gln Pro
        50                  55                  60

His Val Trp Ala Glu Met Gln Arg Tyr Gly Leu Gly Val Val Glu Asp
65                  70                  75                  80
```

Pro Leu Thr Asn Leu Asp Lys Thr Leu Ile Met Tyr Asn Asp Gly Ser
            85                  90                  95

Val Glu Ser Ile Ser Pro Asp Glu Phe Gly Lys Asn Ile Arg Ile Ala
        100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Thr Arg Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Gln Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 64
<211> LENGTH: 313
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (126)..(127)
<223> OTHER INFORMATION: a, c, t, g, unknown or other

<400> SEQUENCE: 64

```
aaagcaatat cgatgtgaat gatcgtgatg cagttacccg tgaagttcag aaaatgtttc    60
cgggtgttga agttctgggc accgcagcct atgattggac cgcagatccg tttagcttag   120
gtgccnnkgc cgcgtatggt gttggtcagc tgtcacgtct gaaagatctg caggcagcag   180
aaggtcgtat tctgtttgcg ggtgcagaaa ccagcaatgg ttggcatgca aatattgatg   240
gtgcagttga aagcggtctg cgtgcaggtc gtgaagttaa acagctgctg agcggtggtg   300
gtggatccat agg                                                     313
```

<210> SEQ ID NO 65
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (20)..(21)
<223> OTHER INFORMATION: a, c, t, g, unknown or other

<400> SEQUENCE: 65

```
tccgtttagc ctgggtgcan nkgcagcgta tggtgttgg                           39
```

<210> SEQ ID NO 66
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (25)..(26)
<223> OTHER INFORMATION: a, c, t, g, unknown or other

<400> SEQUENCE: 66

```
gaagcacgta gccgtttagg tggtnnkacc tttaccagcc gtttt                    45
```

<210> SEQ ID NO 67
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (24)..(25)
<223> OTHER INFORMATION: a, c, t, g, unknown or other

<400> SEQUENCE: 67

```
atgatgcatt catggatacc gaannkcatt atcgtattca gggtggcac                49
```

<210> SEQ ID NO 68
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: modified_base
<222> LOCATION: (22)..(23)
<223> OTHER INFORMATION: a, c, t, g, unknown or other

<400> SEQUENCE: 68
ggtcagctga gtaaaggtgc cnnkctgtat gttcatgtga aacag           45

<210> SEQ ID NO 69
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (28)..(29)
<223> OTHER INFORMATION: a, c, t, g, unknown or other

<400> SEQUENCE: 69
gatgaacagc agccgctgaa ttgggttnnk acccatgatt atagtgatg          49

<210> SEQ ID NO 70
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (25)..(26)
<223> OTHER INFORMATION: a, c, t, g, unknown or other

<400> SEQUENCE: 70
gaactgggca ccattctgag cattnnkatt gcacgtaaag aaaccattg          49

<210> SEQ ID NO 71
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (22)..(23)
<223> OTHER INFORMATION: a, c, t, g, unknown or other

<400> SEQUENCE: 71
accagcaatg gttggcatgc annkattgat ggtgcagttg aaagc           45

<210> SEQ ID NO 72
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (28)..(29)
<223> OTHER INFORMATION: a, c, t, g, unknown or other

<400> SEQUENCE: 72 gaaccagca atggttggca tgcaaatnnk gatggtgcag ttgaaagc           48

<210> SEQ ID NO 73
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (25)..(26)
<223> OTHER INFORMATION: a, c, t, g, unknown or other

<400> SEQUENCE: 73
gcacagatta atagctatat ggcannktat gccggtgaaa ccaccgataa a          51

<210> SEQ ID NO 74
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 74
gcaatgaatt cggtaaaaac attcgcattg cctttgaaaa actgtgtcat gatgcatggg     60 aagttttttcc gcgtccgcat gaaccgatgt ttaccgaacg tgcccgtgaa ctggataaat    120
caagcgttct ggatcgtatt aaaacactgg gtctgagccg tctgcagcag gcacagatta    180
atagctatat ggcactgtat gccggtgaaa ccaccgataa atttggtctg cctggtgttc    240
tgaaactgtt tgcatgtggt ggttggaatt atgatgcctt tatggatacc gaaacgcact    300
atcgtattca aggtggcacc attggtctgg cgaatcagat gctgaccgat agcggtgccg    360
aagttcgtat gagcgttccg gttaccgcgg atagg                                395

<210> SEQ ID NO 75
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 75
gcaatgaatt cggtaaaaac attcgcattg cctttgaaaa actgtgtcat gatgcatggg     60 aagttttttcc gcgtccgcat gaaccgatgt ttaccgaacg tgcccgtgaa ctggataaat    120
caagcgttct ggatcgtatt aaaacactgg gtctgagccg tctgcagcag gcacagatta    180
atagctatat ggcactgtat gccggtgaaa ccaccgataa atttggtctg cctggtgttc    240
tgaaactgtt tgcatgtggt ggttggaatt atgatgcctt tatggatacc gaaacgcact    300
atcgtattca aggtggcacc attggtctga aaaatgcaat ggataccgat agcggtgccg    360
aagttcgtat gagcgttccg gttaccgcgg atagg                                395

<210> SEQ ID NO 76
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 76

| gcaatgaatt cggtaaaaac attcgcattg cctttgaaaa actgtgtcat gatgcatggg | 60 |
| aagttttttcc gcgtccgcat gaaccgatgt ttaccgaacg tgcccgtgaa ctggataaat | 120 |
| caagcgttct ggatcgtatt aaaacactgg gtctgagccg tctgcagcag gcacagatta | 180 |
| atagctatat ggcactgtat gccggtgaaa ccaccgataa atttggtctg cctggtgttc | 240 |
| tgaaactgtt tgcatgtggt ggttggaatt atgatgcctt tatggatacc gaaacgcact | 300 |
| atcgtattca aggtggcacc attggtctga ccaatgcaat gctgaccgat agcggtgccg | 360 |
| aagttcgtat gagcgttccg gttaccgcgg atagg | 395 |

<210> SEQ ID NO 77
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77

| gcaatgaatt cggtaaaaac attcgcattg cctttgaaaa actgtgtcat gatgcatggg | 60 |
| aagttttttcc gcgtccgcat gaaccgatgt ttaccgaacg tgcccgtgaa ctggataaat | 120 |
| caagcgttct ggatcgtatt aaaacactgg gtctgagccg tctgcagcag gcacagatta | 180 |
| atagctatat ggcactgtat gccggtgaaa ccaccgataa atttggtctg cctggtgttc | 240 |
| tgaaactgtt tgcatgtggt ggttggaatt atgatgcctt tatggatacc gaaacgcact | 300 |
| atcgtattca aggtggcacc attggtctga gcaatgcaat gctgaccgat agcggtgccg | 360 |
| aagttcgtat gagcgttccg gttaccgcgg atagg | 395 |

<210> SEQ ID NO 78
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78

| gcaatgaatt cggtaaaaac attcgcattg cctttgaaaa actgtgtcat gatgcatggg | 60 |
| aagttttttcc gcgtccgcat gaaccgatgt ttaccgaacg tgcccgtgaa ctggataaat | 120 |
| caagcgttct ggatcgtatt aaaacactgg gtctgagccg tctgcagcag gcacagatta | 180 |
| atagctatat ggcactgtat gccggtgaaa ccaccgataa atttggtctg cctggtgttc | 240 |
| tgaaactgtt tgcatgtggt ggttggaatt atgatgcctt tatggatacc gaaacgcact | 300 |
| atcgtattca aggtggcacc attggtctgg ataatgcaat gaaaaccgat agcggtgccg | 360 |
| aagttcgtat gagcgttccg gttaccgcgg atagg | 395 |

<210> SEQ ID NO 79
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

```
gcaatgaatt cggtaaaaac attcgcattg cctttgaaaa actgtgtcat gatgcatggg      60 aagttttttcc gcgtccgcat gaaccgatgt ttaccgaacg tgcccgtgaa ctggataaat    120
caagcgttct ggatcgtatt aaaacactgg gtctgagccg tctgcagcag gcacagatta    180
atagctatat ggcactgtat gccggtgaaa ccaccgataa atttggtctg cctggtgttc    240
tgaaactgtt tgcatgtggt ggttggaatt atgatgcctt tatggatacc gaaacgcact    300
atcgtattca aggtggcacc attggtctgg cgaatgcaat gctgaccgat agcggtgccg    360
aagttcgtat gagcgttccg gttaccgcgg atagg                                395
```

<210> SEQ ID NO 80
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
gcaatgaatt cggtaaaaac attcgcattg cctttgaaaa actgtgtcat gatgcatggg      60 aagttttttcc gcgtccgcat gaaccgatgt ttaccgaacg tgcccgtgaa ctggataaat    120
caagcgttct ggatcgtatt aaaacactgg gtctgagccg tctgcagcag gcacagatta    180
atagctatat ggcactgtat gccggtgaaa ccaccgataa atttggtctg cctggtgttc    240
tgaaactgtt tgcatgtggt ggttggaatt atgatgcctt tatggatacc gaaacgcact    300
atcgtattca aggtggcacc attggtctga ccaatctgat gctgaccgat agcggtgccg    360
aagttcgtat gagcgttccg gttaccgcgg atagg                                395
```

<210> SEQ ID NO 81
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gcaatgaatt cggtaaaaac attcgcattg cctttgaaaa actgtgtcat gatgcatggg      60 aagttttttcc gcgtccgcat gaaccgatgt ttaccgaacg tgcccgtgaa ctggataaat    120
caagcgttct ggatcgtatt aaaacactgg gtctgagccg tctgcagcag gcacagatta    180
atagctatat ggcactgtat gccggtgaaa ccaccgataa atttggtctg cctggtgttc    240
tgaaactgtt tgcatgtggt ggttggaatt atgatgcctt tatggatacc gaaacgcact    300
atcgtattca aggtggcacc attggtctga cccgtgcaat gctgaccgat agcggtgccg    360
aagttcgtat gagcgttccg gttaccgcgg atagg                                395
```

<210> SEQ ID NO 82
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
gcaatgaatt cggtaaaaac attcgcattg cctttgaaaa actgtgtcat gatgcatggg    60
aagttttttcc gcgtccgcat gaaccgatgt ttaccgaacg tgcccgtgaa ctggataaat   120
caagcgttct ggatcgtatt aaaacactgg gtctgagccg tctgcagcag gcacagatta   180
atagctatat ggcactgtat gccggtgaaa ccaccgataa atttggtctg cctggtgttc   240
tgaaactgtt tgcatgtggt ggttggaatt atgatgcctt tatggatacc gaaacgcact   300
atcgtattca aggtggcacc attggtctga ttaatgcaca tctgaccgat agcggtgccg   360
aagttcgtat gagcgttccg gttaccgcgg atagg                              395
```

<210> SEQ ID NO 83
<211> LENGTH: 395
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
gcaatgaatt cggtaaaaac attcgcattg cctttgaaaa actgtgtcat gatgcatggg    60
aagttttttcc gcgtccgcat gaaccgatgt ttaccgaacg tgcccgtgaa ctggataaat   120
caagcgttct ggatcgtatt aaaacactgg gtctgagccg tctgcagcag gcacagatta   180
atagctatat ggcactgtat gccggtgaaa ccaccgataa atttggtctg cctggtgttc   240
tgaaactgtt tgcatgtggt ggttggaatt atgatgcctt tatggatacc gaaacgcact   300
atcgtattca aggtggcacc attggtctgg cgaataacat gctgaccgat agcggtgccg   360
aagttcgtat gagcgttccg gttaccgcgg atagg                              395
```

<210> SEQ ID NO 84
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 84

```
gcaatcatat gagcgacaaa accaaaacca atgaaggttt tagccgtcgc agctttattg    60
gtagcgcagc agttgttacc gcaggcgttg caggtctggg tgcaattgat gcagcaagcg   120
caacccagaa aaccaatcgt gcaagcaccg ttaaaggtgg cttcgattat gatgttgttg   180
tggttggtgg tggttttgcc ggtgcaaccg cagcacgtga atgtggtaac cagggtcgtc   240
gtaccctgct gctggaagca cgtagccgtt taggtggtcg tacctttacc agccgttttg   300
caggtcaaga aattgaattt ggtggtcat gggttcattg gttacagccg catgtttggg   360
cagaaatgca gcgttatggt ctgggtgttg ttgaagatcc gctgaccaat ctggataaaa   420
ccctgattat gtataatgac ggtagcgtgg aaagcattag tccggatgaa ttcatagg    478
```

<210> SEQ ID NO 85
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85

```
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtaac cagggtaaac     240
gtaccctgct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478
```

<210> SEQ ID NO 86
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtcag cagggtcgtc     240
gtaccctgct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478
```

<210> SEQ ID NO 87
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtcag cagggtaacc     240
gtaccctgct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478
```

<210> SEQ ID NO 88
<211> LENGTH: 478
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtaac cagggtcagc     240
gtaccctgct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478

<210> SEQ ID NO 89
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtaac cagggtcatc     240
gtaccctgct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478

<210> SEQ ID NO 90
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtaac cagggttatc     240
gtacccatct gctggaagca cgtagccgtt taggtggtcg tacctttacc agccgttttg     300
caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478

```
<210> SEQ ID NO 91
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtctg cagggttatc     240
gtacctttct gctggaagca cgtagccgtt aggtggtcg taccttacc agccgttttg     300 caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478

<210> SEQ ID NO 92
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtctg cagggtcgtc     240
gtaccctgct gctggaagca cgtagccgtt aggtggtcg taccttacc agccgttttg     300 caggtcaaga aattgaattt ggtggtgcat gggttcattg gttacagccg catgtttggg     360
cagaaatgca gcgttatggt ctgggtgttg ttgaagatcc gctgaccaat ctggataaaa     420
ccctgattat gtataatgac ggtagcgtgg aaagcattag tccggatgaa ttcatagg      478

<210> SEQ ID NO 93
<211> LENGTH: 478
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93
gcaatcatat gagcgacaaa accaaaacca atgaaggttt tagccgtcgc agctttattg      60
gtagcgcagc agttgttacc gcaggcgttg caggtctggg tgcaattgat gcagcaagcg     120
caacccagaa aaccaatcgt gcaagcaccg ttaaaggtgg cttcgattat gatgttgttg     180
tggttggtgg tggttttgcc ggtgcaaccg cagcacgtga atgtggtctg cagggttatc     240
agaccctgct gctggaagca cgtagccgtt aggtggtcg taccttacc agccgttttg     300
```

```
caggtcaaga aattgaattt ggtggtgcat gggttcattg gttacagccg catgtttggg    360
cagaaatgca gcgttatggt ctgggtgttg ttgaagatcc gctgaccaat ctggataaaa    420
ccctgattat gtataatgac ggtagcgtgg aaagcattag tccggatgaa ttcatagg     478
```

<210> SEQ ID NO 94
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94

```
gcaatccgcg gttgaacagg ttaatggtgg tgttaaaatc aaaaccgatg acgatgaaat     60
cattaccgca ggcaccaacg ttattaccgt tccgctgaat acctataaac atattggttt    120
tacaccggca ctgagcaaag gtaaacagct ttttatcaaa gaaggtcagc tgagtaaagg    180
tgccaaactg tatgttcatg tgaaacagaa tctgggtcgt gtttttgcat ttgcagatga    240
acagcagccg ctgaattggg ttcagaccca tgattatagt gatgaactgg gcaccattct    300
gagcattacc attgcacgta aagaaaccat cgatatagg                          339
```

<210> SEQ ID NO 95
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

```
gcaatccgcg gttgaacagg ttaatggtgg tgttaaaatc aaaaccgatg acgatgaaat     60
cattaccgca ggcgttgcgg ttcagaccgt tccgctgaat acctataaac atattggttt    120
tacaccggca ctgagcaaag gtaaacagcg ttttatcaaa gaaggtcagc tgagtaaagg    180
tgccaaactg tatgttcatg tgaaacagaa tctgggtcgt gtttttgcat ttgcagatga    240
acagcagccg ctgaattggg ttcagaccca tgattatagt gatgaactgg gcaccattct    300
gagcattacc attgcacgta aagaaaccat cgatatagg                          339
```

<210> SEQ ID NO 96
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96

```
gcaatccgcg gttgaacagg ttaatggtgg tgttaaaatc aaaaccgatg acgatgaaat     60
cattaccgca ggcgttgcgg ttaacaccgt tccgctgaat acctataaac atattggttt    120
tacaccggca ctgagcaaag gtaaacagcg ttttatcaaa gaaggtcagc tgagtaaagg    180
tgccaaactg tatgttcatg tgaaacagaa tctgggtcgt gtttttgcat ttgcagatga    240
acagcagccg ctgaattggg ttcagaccca tgattatagt gatgaactgg gcaccattct    300
gagcattacc attgcacgta aagaaaccat cgatatagg                          339
```

```
<210> SEQ ID NO 97
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gcaatccgcg gttgaacagg ttaatggtgg tgttaaaatc aaaaccgatg acgatgaaat      60
cattaccgca ggcgttgcgg ttatgaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga    240 acagcagccg ctgaattggg ttcagaccca tgattatagt gatgaactgg gcaccattct     300
gagcattacc attgcacgta aagaaaccat cgatatagg                            339

<210> SEQ ID NO 98
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gcaatccgcg gttgaacagg ttaatggtgg tgttaaaatc aaaaccgatg acgatgaaat      60
cattaccgca ggcgttgcgg ttcataccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga    240 acagcagccg ctgaattggg ttcagaccca tgattatagt gatgaactgg gcaccattct     300
gagcattacc attgcacgta aagaaaccat cgatatagg                            339

<210> SEQ ID NO 99
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gcaatccgcg gttgaacagg ttaatggtgg tgttaaaatc aaaaccgatg acgatgaaat      60
cattaccgca ggcgttaacg ttcataccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga    240 acagcagccg ctgaattggg ttcagaccca tgattatagt gatgaactgg gcaccattct     300
gagcattacc attgcacgta aagaaaccat cgatatagg                            339

<210> SEQ ID NO 100
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 100

```
gcaatccgcg gttgaacagg ttaatggtgg tgttaaaatc aaaaccgatg acgatgaaat      60
cattaccgca ggcgttcagg ttcataccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga     240
acagcagccg ctgaattggg ttcagaccca tgattatagt gatgaactgg gcaccattct     300
gagcattacc attgcacgta aagaaaccat cgatatagg                             339
```

<210> SEQ ID NO 101
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

```
gcaatccgcg gttgaacagg ttaatggtgg tgttaaaatc aaaaccgatg acgatgaaat      60
cattaccgca ggcgttaacg ttattaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga     240
acagcagccg ctgaattggg ttcagaccca tgattatagt gatgaactgg gcaccattct     300
gagcattacc attgcacgta aagaaaccat cgatatagg                             339
```

<210> SEQ ID NO 102
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102

```
gcaatccgcg gttgaacagg ttaatggtgg tgttaaaatc aaaaccgatg acgatgaaat      60
cattaccgca ggcgttaccg ttattaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gttttttgcat ttgcagatga     240
acagcagccg ctgaattggg ttcagaccca tgattatagt gatgaactgg gcaccattct     300
gagcattacc attgcacgta aagaaaccat cgatatagg                             339
```

<210> SEQ ID NO 103
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103

```
gcaatccgcg gttgaacagg ttaatggtgg tgttaaaatc aaaaccgatg acgatgaaat      60
cattaccgca ggcgttgttg ttattaccgt tccgcgtaat acctataaac atattggttt     120
```

```
tacaccggca ctgagcaaag gtaaacagcg ttttatcaaa gaaggtcagc tgagtaaagg    180
tgccaaactg tatgttcatg tgaaacagaa tctgggtcgt gttttttgcat ttgcagatga    240 acagcagccg ctgaattggg ttcagaccca tgattatagt gatgaactgg gcaccattct    300
gagcattacc attgcacgta aagaaaccat cgatatagg                            339
```

<210> SEQ ID NO 104
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

```
gcaatccgcg gttgaacagg ttaatggtgg tgttaaaatc aaaaccgatg acgatgaaat    60
cattaccgca ggcgttgttg ttatgaccgt tccgctgaat acctataaac atattggttt    120
tacaccggca ctgagcaaag gtaaacagcg ttttatcaaa gaaggtcagc tgagtaaagg    180
tgccaaactg tatgttcatg tgaaacagaa tctgggtcgt gttttttgcat ttgcagatga    240 acagcagccg ctgaattggg ttcagaccca tgattatagt gatgaacagg gcaccagcct    300
gagcattacc attgcacgta aagaaaccat cgatatagg                            339
```

<210> SEQ ID NO 105
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105

```
gcaatccgcg gttgaacagg ttaatggtgg tgttaaaatc aaaaccgatg acgatgaaat    60
cattaccgca ggcgttgttg ttatgaccgt tccgctgaat acctataaac atattggttt    120
tacaccggca ctgagcaaag gtaaacagcg ttttatcaaa gaaggtcagc tgagtaaagg    180
tgccaaactg tatgttcatg tgaaacagaa tctgggtcgt gttttttgcat ttgcagatga    240 acagcagccg ctgaattggg ttcagaccca tgattatagt gatgaagcgg gcaccgcgct    300
gagcattacc attgcacgta aagaaaccat cgatatagg                            339
```

<210> SEQ ID NO 106
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106

```
gcaatccgcg gttgaacagg ttaatggtgg tgttaaaatc aaaaccgatg acgatgaaat    60
cattaccgca ggcgttgttg ttatgaccgt tccgctgaat acctataaac atattggttt    120
tacaccggca ctgagcaaag gtaaacagcg ttttatcaaa gaaggtcagc tgagtaaagg    180
tgccaaactg tatgttcatg tgaaacagaa tctgggtcgt gttttttgcat ttgcagatga    240 acagcagccg ctgaattggg ttcagaccca tgattatagt gatgaacagg gcaccgcgct    300
```
gagcattacc attgcacgta aagaaaccat cgatatagg        339

<210> SEQ ID NO 107
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
gcaatccgcg gttgaacagg ttaatggtgg tgttaaaatc aaaaccgatg acgatgaaat        60
cattaccgca ggcgttgttg ttatgaccgt tccgctgaat acctataaac atattggttt       120
tacaccggca ctgagcaaag gtaaacagcg ttttatcaaa gaaggtcagc tgagtaaagg       180
tgccaaactg tatgttcatg tgaaacagaa tctgggtcgt gttttttgcat ttgcagatga       240 acagcagccg ctgaattggg ttcagaccca tgattatagt gatgaaaacg gcaccgcgct       300
gagcattacc attgcacgta aagaaaccat cgatatagg                              339

<210> SEQ ID NO 108
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
gcaatccgcg gttgaacagg ttaatggtgg tgttaaaatc aaaaccgatg acgatgaaat        60
cattaccgca ggcgttgttg ttatgaccgt tccgctgaat acctataaac atattggttt       120
tacaccggca ctgagcaaag gtaaacagcg ttttatcaaa gaaggtcagc tgagtaaagg       180
tgccaaactg tatgttcatg tgaaacagaa tctgggtcgt gttttttgcat ttgcagatga       240 acagcagccg ctgaattggg ttcagaccca tgattatagt gatgaaaacg gcaccattct       300
gagcattacc caggcacgta aagaaaccat cgatatagg                              339

<210> SEQ ID NO 109
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
gcaatccgcg gttgaacagg ttaatggtgg tgttaaaatc aaaaccgatg acgatgaaat        60
cattaccgca ggcgttgttg ttatgaccgt tccgctgaat acctataaac atattggttt       120
tacaccggca ctgagcaaag gtaaacagcg ttttatcaaa gaaggtcagc tgagtaaagg       180
tgccaaactg tatgttcatg tgaaacagaa tctgggtcgt gttttttgcat ttgcagatga       240 acagcagccg ctgaattggg ttcagaccca tgattatagt gatgaactgg gcaccgcgct       300
gagcattacc accgcacgta aagaaaccat cgatatagg                              339

<210> SEQ ID NO 110
<211> LENGTH: 339
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 110
gcaatccgcg gttgaacagg ttaatggtgg tgttaaaatc aaaaccgatg acgatgaaat      60
cattaccgca ggcgttgttg ttatgaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gtttttgcat ttgcagatga     240
acagcagccg ctgaattggg ttcagaccca tgattatagt gatgaactgg gcaccgcgaa     300
cagcattacc attgcacgta agaaaccat cgatatagg                             339

<210> SEQ ID NO 111
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111
gcaatccgcg gttgaacagg ttaatggtgg tgttaaaatc aaaaccgatg acgatgaaat      60
cattaccgca ggcgttgttg ttatgaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gtttttgcat ttgcagatga     240
acagcagccg ctgaattggg ttcagaccca tgattatagt gatgaactgg gcaccaccct     300
gagcattacc accgcacgta agaaaccat cgatatagg                             339

<210> SEQ ID NO 112
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
gcaatccgcg gttgaacagg ttaatggtgg tgttaaaatc aaaaccgatg acgatgaaat      60
cattaccgca ggcgttgttg ttatgaccgt tccgctgaat acctataaac atattggttt     120
tacaccggca ctgagcaaag gtaaacagcg ttttatcaaa gaaggtcagc tgagtaaagg     180
tgccaaactg tatgttcatg tgaaacagaa tctgggtcgt gtttttgcat ttgcagatga     240
acagcagccg ctgaattggg ttcagaccca tgattatagt gatgaactgg gcaccaccct     300
gagcattacc attgcacgta agaaaccat cgatatagg                             339

<210> SEQ ID NO 113
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113
```

```
gcaatccgcg gttgaacagg ttaatggtgg tgttaaaatc aaaaccgatg acgatgaaat    60
cattaccgca ggcgttgttg ttatgaccgt tccgctgaat acctataaac atattggttt   120
tacaccggca ctgagcaaag gtaaacagcg ttttatcaaa gaaggtcagc tgagtaaagg   180
tgccaaactg tatgttcatg tgaaacagaa tctgggtcgt gttttttgcat ttgcagatga   240 acagcagccg ctgaattggg ttcagaccca tgattatagt gatgaaaacg gcaccattct   300
gagcattacc attcagcgta aagaaaccat cgatatagg                          339
```

```
<210> SEQ ID NO 114
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
aaccatcgat gtgaatgatc gtgatgcagt tacccgtgaa gttcagaaaa tgtttccggg    60
tgttgaagtt ctgggcaccg cagcctatga ttggaccgca gatccgttta gcttaggtgc   120
ctgggcagcg tatggtgttg gtcagctgtc acgtctgaaa gatctgcagg cagcagaagg   180
tcgtcagctg agcgcgggtg cagaaaccag caatggttgg catgcaaata ttgatggtgc   240
agttgaaagc ggtctgcgtg caggtcgtga agttaaacag ctgctgagcg gtggtggtgg   300
atccggtagc ggtcatcatc accatcatca ttaactcgag aatcg                   345
```

```
<210> SEQ ID NO 115
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115
aaccatcgat gtgaatgatc gtgatgcagt tacccgtgaa gttcagaaaa tgtttccggg    60
tgttgaagtt ctgggcaccg cagcctatga ttggaccgca gatccgttta gcttaggtgc   120
ctgggcagcg tatggtgttg gtcagctgtc acgtctgaaa gatctgcagg cagcagaagg   180
tcgtgaactg aacgcgggtg cagaaaccag caatggttgg catgcaaata ttgatggtgc   240
agttgaaagc ggtctgcgtg caggtcgtga agttaaacag ctgctgagcg gtggtggtgg   300
atccggtagc ggtcatcatc accatcatca ttaactcgag aatcg                   345
```

```
<210> SEQ ID NO 116
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
aaccatcgat gtgaatgatc gtgatgcagt tacccgtgaa gttcagaaaa tgtttccggg    60
tgttgaagtt ctgggcaccg cagcctatga ttggaccgca gatccgttta gcttaggtgc   120
ctgggcagcg tatggtgttg gtcagctgtc acgtctgaaa gatctgcagg cagcagaagg   180
tcgtgcgctg aacgcgggtg cagaaaccag caatggttgg catgcaaata ttgatggtgc   240
```
agttgaaagc ggtctgcgtg caggtcgtga agttaaacag ctgctgagcg gtggtggtgg     300
atccggtagc ggtcatcatc accatcatca ttaactcgag aatcg                      345

<210> SEQ ID NO 117
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
aaccatcgat gtgaatgatc gtgatgcagt tacccgtgaa gttcagaaaa tgtttccggg       60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtcagctg caggcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                      345

<210> SEQ ID NO 118
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118
aaccatcgat gtgaatgatc gtgatgcagt tacccgtgaa gttcagaaaa tgtttccggg       60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtaccctg caggcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                      345

<210> SEQ ID NO 119
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119
aaccatcgat gtgaatgatc gtgatgcagt tacccgtgaa gttcagaaaa tgtttccggg       60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtgaactg ctggcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                      345

<210> SEQ ID NO 120

```
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
aaccatcgat gtgaatgatc gtgatgcagt tacccgtgaa gttcagaaaa tgtttccggg      60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtattctg tttgcgggtg cagaaaaaag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                     345

<210> SEQ ID NO 121
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
aaccatcgat gtgaatgatc gtgatgcagt tacccgtgaa gttcagaaaa tgtttccggg      60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtattcat gcggcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                     345

<210> SEQ ID NO 122
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
aaccatcgat gtgaatgatc gtgatgcagt tacccgtgaa gttcagaaaa tgtttccggg      60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtattctg gcggcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                     345

<210> SEQ ID NO 123
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 123

```
aaccatcgat gtgaatgatc gtgatgcagt tacccgtgaa gttcagaaaa tgtttccggg      60
tgttgaagtt ctgggcaccg cagcctatga ttggaccgca gatccgttta gcttaggtgc     120
ctgggcagcg tatggtgttg gtcagctgtc acgtctgaaa gatctgcagg cagcagaagg     180
tcgtgcgctg tatgcgggtg cagaaaccag caatggttgg catgcaaata ttgatggtgc     240
agttgaaagc ggtctgcgtg caggtcgtga agttaaacag ctgctgagcg gtggtggtgg     300
atccggtagc ggtcatcatc accatcatca ttaactcgag aatcg                    345
```

<210> SEQ ID NO 124
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Arg Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
```

```
            275                 280                 285
Lys Ile Lys Thr Asp Asp Glu Ile Ile Thr Ala Gly Val Val Val
        290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala Phe Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser
```

<210> SEQ ID NO 125
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Lys Trp Val His Trp Leu Gln
                100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
        130                 135                 140
```

-continued

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
            165                 170                 175

His Glu Pro Met Phe Thr Glu Arg Ala Arg Glu Leu Asp Lys Ser Ser
        180                 185                 190

Val Leu Asp Arg Ile Lys Thr Leu Gly Leu Ser Arg Leu Gln Gln Ala
    195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
            245                 250                 255

Thr Ile Gly Leu Ile Asn Ala Met Leu Thr Asp Ser Gly Ala Glu Val
        260                 265                 270

Arg Met Ser Val Pro Val Thr Ala Val Glu Gln Val Asn Gly Gly Val
    275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Phe Ala Asp Glu Gln Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
            405                 410                 415

Thr Ala Asp Pro Phe Ser Leu Gly Ala Trp Ala Ala Tyr Gly Val Gly
        420                 425                 430

Gln Leu Ser Arg Leu Lys Asp Leu Gln Ala Ala Glu Gly Arg Ile Leu
    435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 126
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Ser Asp Lys Thr Lys Thr Asn Glu Gly Phe Ser Arg Arg Ser Phe Ile
1               5                   10                  15

```
Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Thr Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430
```

```
Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 127
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300
```

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Cys Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 128
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro

```
                    165                 170                 175
His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Val Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 129
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30
```

```
Asp Ala Ala Ser Ala Thr Gln Lys Thr Asn Arg Ala Ser Thr Val Lys
             35                  40                  45

Gly Gly Phe Asp Tyr Asp Val Val Val Gly Gly Phe Ala Gly
 50                  55                  60

Ala Thr Ala Ala Arg Glu Cys Gly Leu Gln Gly Tyr Arg Thr Leu Leu
 65                  70                  75                  80

Leu Glu Ala Arg Ser Arg Leu Gly Gly Gln Thr Phe Thr Ser Arg Phe
                 85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
            210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
            275                 280                 285

Lys Ile Lys Thr Asp Asp Glu Ile Ile Thr Ala Gly Val Val Val
            290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
```

```
                    450                 455                 460
Ala Val Glu Ser Gly Leu Arg Ala Gly Arg Glu Val Lys Gln Leu Leu
465                 470                 475                 480

Ser

<210> SEQ ID NO 130
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320
```

```
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
            340                 345                 350
Ala Phe Ala Asp Glu Gln Gln Pro Leu Asn Trp Val Lys Thr His Asp
        355                 360                 365
Tyr Ser Asp Glu Leu Gly Thr Ile Leu Ser Ile Thr Ile Ala Arg Lys
    370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
            420                 425                 430
Gln Leu Ser Arg Leu Lys Asp Leu Gln Ala Ala Glu Gly Arg Ile Leu
        435                 440                 445
Phe Ala Gly Ala Glu Thr Ser Asn Gly Trp His Ala Asn Ile Asp Gly
    450                 455                 460
Ala Val Glu Ser Gly Leu Arg Ala Gly Arg Glu Val Lys Gln Leu Leu
465                 470                 475                 480
Ser
```

<210> SEQ ID NO 131
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 131

```
Ser Asp Lys Thr Lys Thr Asn Glu Gly Phe Ser Arg Arg Ser Phe Ile
1               5                   10                  15
Gly Ser Ala Ala Val Val Thr Ala Gly Val Ala Gly Leu Gly Ala Ile
            20                  25                  30
Asp Ala Ala Ser Ala Thr Gln Lys Thr Asn Arg Ala Ser Thr Val Lys
        35                  40                  45
Gly Gly Phe Asp Tyr Asp Val Val Val Gly Gly Gly Phe Ala Gly
    50                  55                  60
Ala Thr Ala Ala Arg Glu Cys Gly Leu Gln Gly Tyr Arg Thr Leu Leu
65                  70                  75                  80
Leu Glu Ala Arg Ser Arg Leu Gly Gly Arg Thr Phe Thr Ser Arg Phe
                85                  90                  95
Ala Gly Gln Glu Ile Glu Phe Gly Gly Ala Trp Val His Trp Leu Gln
            100                 105                 110
Pro His Val Trp Ala Glu Met Gln Arg Tyr Gly Leu Gly Val Val Glu
        115                 120                 125
Asp Pro Leu Thr Asn Leu Asp Lys Thr Leu Ile Met Tyr Asn Asp Gly
    130                 135                 140
Ser Val Glu Ser Ile Ser Pro Asp Glu Phe Gly Lys Asn Ile Arg Ile
145                 150                 155                 160
Ala Phe Glu Lys Leu Cys His Asp Ala Trp Glu Val Phe Pro Arg Pro
                165                 170                 175
His Glu Pro Met Phe Thr Glu Arg Ala Arg Glu Leu Asp Lys Ser Ser
            180                 185                 190
```

```
Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
        260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
        290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
        340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Val Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser

<210> SEQ ID NO 132
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Val Gly Gly Gly Phe Ala Gly
```

-continued

```
              50                  55                  60

Ala Thr Ala Ala Arg Glu Cys Gly Leu Gln Gly Tyr Arg Thr Leu Leu
 65                  70                  75                  80

Leu Glu Ala Arg Ser Arg Leu Gly Gly Arg Thr Phe Thr Ser Arg Phe
                     85                  90                  95

Ala Gly Gln Glu Ile Glu Phe Gly Gly Ala Trp Val His Trp Leu Gln
                    100                 105                 110

Pro His Val Trp Ala Glu Met Gln Arg Tyr Gly Leu Gly Val Val Glu
                    115                 120                 125

Asp Pro Leu Thr Asn Leu Asp Lys Thr Leu Ile Met Tyr Asn Asp Gly
            130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                    165                 170                 175

His Glu Pro Met Phe Thr Glu Arg Ala Arg Glu Leu Asp Lys Ser Ser
                180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
        290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Leu Ile Asp Gly
    450                 455                 460

Ala Val Glu Ser Gly Leu Arg Ala Gly Arg Glu Val Lys Gln Leu Leu
465                 470                 475                 480
```

Ser

<210> SEQ ID NO 133
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 133

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
```

```
            340                 345                 350
Ala Phe Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Tyr Ile Asp Gly
        450                 455                 460

Ala Val Glu Ser Gly Leu Arg Ala Gly Arg Glu Val Lys Gln Leu Leu
465                 470                 475                 480

Ser
```

<210> SEQ ID NO 134
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 134

```
Gly Phe Asp Tyr Asp Val Val Val Gly Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Phe Gly Gly Arg Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205
```

```
Ile Gly Leu Ile Asn Ala Met Leu Thr Asp Ser Gly Ala Glu Val Arg
        210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
                340                 345                 350

Met Phe Pro Gly Val Glu Val Leu Gly Thr Ala Ala Tyr Asp Trp Thr
            355                 360                 365

Ala Asp Pro Phe Ser Leu Gly Ala Trp Ala Ala Tyr Gly Val Gly Gln
370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 135
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
```

```
                130                 135                 140
Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
                195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Pro Leu Asn Trp Val Gln Thr His Asp
        355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Arg Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser

<210> SEQ ID NO 136
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136
```

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
        130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Pro His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
        290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Pro Leu Asn Trp Val Gln Thr His Asp
        355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
```

```
                    420                 425                 430
Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser

<210> SEQ ID NO 137
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285
```

```
Lys Ile Lys Thr Asp Asp Asp Glu Ile Ile Thr Ala Gly Val Val Val
            290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala His Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Phe Ile Asp Gly
450                 455                 460

Ala Val Glu Ser Gly Leu Arg Ala Gly Arg Glu Val Lys Gln Leu Leu
465                 470                 475                 480

Ser
```

<210> SEQ ID NO 138
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 138

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160
```

```
Ala Phe Glu Lys Leu Cys His Asp Ala Trp Glu Val Phe Pro Arg Pro
            165                 170                 175

His Glu Pro Met Phe Thr Glu Arg Ala Arg Glu Leu Asp Lys Ser Ser
        180                 185                 190

Val Leu Asp Arg Ile Lys Thr Leu Gly Leu Ser Arg Leu Gln Gln Ala
    195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
            245                 250                 255

Thr Ile Gly Leu Ile Asn Ala Met Leu Thr Asp Ser Gly Ala Glu Val
        260                 265                 270

Arg Met Ser Val Pro Val Thr Ala Val Glu Gln Val Asn Gly Gly Val
    275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Phe Ala Asp Glu Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
            405                 410                 415

Thr Ala Asp Pro Phe Ser Leu Gly Ala Leu Ala Ala Tyr Gly Val Gly
        420                 425                 430

Gln Leu Ser Arg Leu Lys Asp Leu Gln Ala Ala Glu Gly Arg Ile Leu
    435                 440                 445

Phe Ala Gly Ala Glu Thr Ser Asn Gly Trp His Ala Met Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 139
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Gly Gly Gly Gly Ser Gly Ser Gly His His His His
1               5                   10
```

-continued

```
<210> SEQ ID NO 140
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Leu Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365
```

Tyr Ser Asp Glu Leu Gly Thr Ile Leu Ser Ile Thr Ile Ala Arg Lys
            370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
            450                 455                 460

Ala Val Glu Ser Gly Leu Arg Ala Gly Arg Glu Val Lys Gln Leu Leu
465                 470                 475                 480

Ser

<210> SEQ ID NO 141
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Ser Ala Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
            130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn

```
                225                 230                 235                 240
Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
                260                 265                 270

Arg Met Ser Val Pro Val Thr Ala Val Glu Gln Val Asn Gly Gly Val
                275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala Phe Ala Asp Glu Gln Gln Pro Leu Asn Trp Val Gln Thr His Asp
                355                 360                 365

Tyr Ser Asp Glu Leu Gly Thr Ile Leu Ser Ile Thr Ile Ala Arg Lys
                370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
                435                 440                 445

Phe Ala Gly Ala Glu Thr Ser Asn Gly Trp His Ala Asn Ile Asp Gly
                450                 455                 460

Ala Val Glu Ser Gly Leu Arg Ala Gly Arg Glu Val Lys Gln Leu Leu
465                 470                 475                 480

Ser

<210> SEQ ID NO 142
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
                35                  40                  45

Gly Gly Phe Asp Tyr Asp Val Val Val Gly Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95
```

```
Ala Gly Gln Glu Ile Glu Phe Gly Gly His Trp Val His Trp Leu Gln
             100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 143
<211> LENGTH: 481
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 143

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Pro Trp Val His Trp Leu Gln
                100                 105                 110

Pro His Val Trp Ala Glu Met Gln Arg Tyr Gly Leu Gly Val Val Glu
                115                 120                 125

Asp Pro Leu Thr Asn Leu Asp Lys Thr Leu Ile Met Tyr Asn Asp Gly
                130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
                180                 185                 190

Val Leu Asp Arg Ile Lys Thr Leu Gly Leu Ser Arg Leu Gln Gln Ala
                195                 200                 205

Gln Ile Asn Ser Tyr Met Ala Leu Tyr Ala Gly Glu Thr Thr Asp Lys
                210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
                260                 265                 270

Arg Met Ser Val Pro Val Thr Ala Val Glu Gln Val Asn Gly Gly Val
                275                 280                 285

Lys Ile Lys Thr Asp Asp Glu Ile Ile Thr Ala Gly Val Val Val
                290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala Phe Ala Asp Glu Gln Gln Pro Leu Asn Trp Val Gln Thr His Asp
                355                 360                 365

Tyr Ser Asp Glu Leu Gly Thr Ile Leu Ser Ile Thr Ile Ala Arg Lys
                370                 375                 380

```
Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 144
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 144

His His His His His His
1               5
```

NICOTINE DEGRADING ENZYME VARIANTS

RELATED APPLICATIONS

This application is the U.S. National Stage of International Application No. PCT/US2018/016664, filed Feb. 2, 2018, and claims priority under 35 U.S.C. § 119(e) to U.S. Provisional Application 62/454,331 filed Feb. 3, 2017, and U.S. Provisional Application 62/535,507 filed Jul. 21, 2017, the entire contents of which are incorporated herein by reference.

GOVERNMENT LICENSE RIGHTS

This invention was made with Government support under National Institutes of Health grant RO1 DA038877 awarded by the PHS. The Government has certain rights in the invention.

FIELD

The present disclosure relates generally to the field of treating nicotine addiction or nicotine poisoning. Described are nicotine-degrading enzyme variants that exhibit increased nicotine-degrading activity and/or decreased immunogenicity relative to the wild-type NicA2 enzyme, compositions comprising them, and methods using them.

BACKGROUND

The following discussion is provided to aid the reader in understanding the disclosure and is not admitted to describe or constitute prior art thereto.

Smoking is a global healthcare problem. The World Health Organization estimates that there are 1.3 billion smokers worldwide today and nearly five million tobacco-related deaths each year. If current smoking patterns continue, smoking will cause some 10 million deaths each year by 2020. According to the U.S. Center for Disease Control (CDC), tobacco use is the single leading preventable cause of death in the U.S., responsible for approximately 438,000 deaths each year. In addition, it is estimated that smoking results in an annual health-related economic cost of approximately $157 billion. The CDC estimates that, among the 45 million adult smokers in the U.S., 70% want to quit, but less than five percent of those who try to quit remain smoke-free after 12 months.

One reason it is difficult to quit smoking is addiction to the nicotine in cigarettes and other tobacco products. Nicotine is a small molecule that upon inhalation into the body quickly passes into the bloodstream and subsequently reaches the brain by crossing the blood-brain barrier. Once in the brain, the nicotine binds to nicotinic receptors, which results in the release of stimulants, such as dopamine, activating the reward system and providing the smoker with a positive and pleasurable re-enforcing experience, which leads to addiction.

In addition to the detrimental health effects associated with smoking and other tobacco use, nicotine poisoning, which results from ingestion or inhalation of too much nicotine, is another nicotine-related health problem. The $LD_{50}$ of nicotine is 50 mg/kg for rats and 3 mg/kg for mice. A dose as low as 30-60 mg (0.5-1.0 mg/kg) may be lethal for adult humans, while children may become ill following ingestion of one cigarette, and ingestion of more than this may cause a child to become severely ill. On the other hand, some evidence suggests that a lethal dose may be as high as 500 mg or more (1.0-7.1 mg/kg) for a human adult. In either case, acute nicotine poisoning usually occurs in children who accidentally chew on nicotine gum or patches or ingest the "e-liquid" of electronic cigarettes. In rare instances, children have also been known to become ill after ingesting cigarettes. There are several hundred cases of acute nicotine poisoning reported every month in the United States alone.

Typically, initial treatment of nicotine poisoning may include the administration of activated charcoal to try to reduce gastrointestinal absorption, while additional treatment may address the symptoms that result from nicotine poisoning.

The use of the wild-type NicA2 enzyme for smoking cessation has been proposed (see, e.g., Xue et al., *J. Am. Chem. Soc.* 137: 10136-39 (2015)). Nevertheless, there remains a need for additional agents, compositions and methods for treating nicotine addiction, as well as for agents, compositions, and methods for treating nicotine poisoning.

SUMMARY

Described herein are nicotine-degrading enzyme variants that exhibit increased nicotine-degrading activity and/or decreased immunogenicity relative to the wild-type NicA2 enzyme, compositions comprising them, and methods using them.

In some embodiments, the nicotine-degrading enzyme variant comprises an amino acid sequence that is a variant of the amino acid sequence of the wild-type NicA2 enzyme set forth in SEQ ID NO: 1, wherein the variant sequence has at least one substitution, addition, or deletion relative to SEQ ID NO: 1 that increases the nicotine-degrading activity and/or decreases the immunogenicity of the variant relative to the wild-type NicA2 enzyme.

In some embodiments, the variant exhibits increased nicotine-degrading activity relative to the wild-type NicA2 enzyme. In some embodiments, the variant of the wild-type NicA2 sequence comprises the substitution AF104L, G106S, A107H, A107P, 107R, A107K, A107T, F355C, F355V, W427Q, W427E, W427S, W427M, W427H, W427L, W427R, R91A, R91Q, R91F, R91G, R91T, R91L, R91S, R91N, T250G, T250L, T250R, T250V, T250P, K340P, K340I, K340V, K340D, K340E, Q366K, Q366E, Q366V, Q366L, Q366I, Q366Y, T381P, T381I, T381V, T381Q, T381N, T381L, T381M, N462L, N462Y, N462S, N462F, N462G, N462E, N462A, N462M, I463F, I463Y, I463A, I463V, I463L, L217Q, L217G, L217E, L217I, L217C, or L217S, or any two or more thereof at different positions. In some embodiments, the variant sequence comprises an amino acid sequence selected from any one of SEQ ID NOs: 5-56. In some embodiments, the nicotine-degrading activity of the variant is at least 200%, at least 300%, or at least 400% of the nicotine-degrading activity of the wild-type NicA2 enzyme. In some embodiments, the variant sequence comprises at least one, at least two, or at least three substitution(s) at amino acid positions 91, 104, 106, 107, 217, 250, 340, 355, 366, 381, 427, 462, or 463 of SEQ ID NO:1. In some embodiments, the variant may have a deletion of 1-52 amino acids at the N-terminus of the peptide. For example, a variant derived from SEQ ID NO:1 may comprise a deletion of 5, 10, 15, 20, 25, 30, 35, 40, 45, 50, 51, or 52 amino acids from the N-terminus of the peptide. In some embodiments, the variant additionally or alternatively may have a deletion of 1 or more amino acids from the C-terminus of the peptide, such as a deletion of the C-terminal residue.

Additionally or alternatively, in some embodiments, the NicA2 variant exhibits reduced immunogenicity relative to the wild-type NicA2 enzyme. In some embodiments, the immunogenicity relative to the wild-type NicA2 enzyme is reduced by 75% or more. In some embodiments, the variant sequence comprises at least one substitution, addition, or deletion in an immunogenic T-cell epitope within a region selected from amino acids 10-32, 68-94, 189-225, 248-285, 296-327, 336-391, or 435-459 of SEQ ID NO: 1. In some embodiments, the variant sequence comprises at least one substitution, addition, or deletion in an immunogenic T-cell epitope selected from amino acids 16-24, 73-81, 258-266, 302-310, 373-381, or 447-455 of SEQ ID NO: 1. In some embodiments, the variant sequence comprises at least one substitution, addition, or deletion at a position selected from (a) amino acid residues 74, 77, 78, or 80 of SEQ ID NO: 1; (b) amino acid residues 262, 263, 264, or 266 of SEQ ID NO: 1; (c) amino acid residues 303, 304, 306, or 310 of SEQ ID NO: 1; (d) amino acid residues 374, 377, 378, 382, or 383 of SEQ ID NO: 1; and/or (e) amino acid residues 450, 451, 452, or 457 of SEQ ID NO: 1. In some embodiments, the variant sequence comprises at least one substitution or substation combination selected from those listed for Epitope B in Table 3. Additionally or alternatively, in some embodiments, the variant sequence comprises at least one substitution or substation combination selected from those listed for Epitope 1 in Table 3. Additionally or alternatively, in some embodiments, the variant sequence comprises at least one substitution or substation combination selected from those listed for Epitope 2 in Table 3. Additionally or alternatively, in some embodiments, the variant sequence comprises at least one substitution or substation combination selected from those listed for Epitope 3 in Table 3. Additionally or alternatively, in some embodiments, the variant sequence comprises at least one substitution or substation combination selected from those listed for Epitope 4 in Table 3. In some embodiments, the variant comprises at least one substitution or substation combination selected from (a) I262T; (b) I262S; (c) I262A; (d) I262T and A264L; and/or (e) I262T and N263R.

Additionally or alternatively, in some embodiments, the variant may further comprise at least one substitution at amino acid positions 74, 77, 78, 80, 262-266, 303, 304, 306, 310, 374, 377, 378, 382, 383, 450-452, or 457. For example, the variant may comprise a substitution at amino acid position 262 or 263, or the variant may comprise substitutions at amino acid positions 262 and 263. In some embodiments, the substitution may be I262A, I262T, and/or N263R. For example, in some embodiments, the variant sequence comprises an amino acid sequence of SEQ ID NO: 62 or 63.

In some embodiments, the nicotine-degrading enzyme variant comprises an amino acid sequence that is a variant of the amino acid sequence of the wild-type NOX enzyme set forth in SEQ ID NO: 57, wherein the variant sequence has at least one substitution, addition, or deletion relative to SEQ ID NO: 57 that increases the nicotine-degrading activity and/or decreases the immunogenicity of the variant relative to the wild-type NOX enzyme or the wild-type NicA2 enzyme.

In some embodiments, the variant of the wild-type NOX sequence comprises the substitution at position 423 of SEQ ID NO: 57. For example, the variant sequence may comprise the substitution W423A, W423S, W423E, or W423H. In some embodiments, the variant sequence comprises an amino acid sequence selected from any one of SEQ ID NOs: 58-61. In some embodiments, the nicotine-degrading activity of the NOX variant is at least 200% of the nicotine-degrading activity of the wild-type NicA2 enzyme. In some embodiments, the nicotine-degrading activity of the NOX variant is at least 200% of the nicotine-degrading activity of the wild-type NOX enzyme.

Additionally or alternatively, in some embodiments, the NOX variant exhibits reduced immunogenicity relative to the wild-type NOX enzyme or the wild-type NicA2 enzyme. In some embodiments, the immunogenicity relative to the wild-type NOX or NicA2 enzymes is reduced by 75% or more.

Additionally or alternatively, in some embodiments, the variant further comprises a deletion of at least amino acids 1-38 of SEQ ID NOs: 1 or 57, or of amino acids 1-50 of SEQ ID NOs: 1 or 57, or amino acids 1-51 of SEQ ID NOs: 1 or 57, or amino acids 1-52 of SEQ ID NOs: 1 or 57. In some embodiments, the variant may further comprises a His-tag, such as a His-tag comprising the amino acid sequence of SEQ ID NO: 139. Additionally or alternatively, in some embodiments, the variant comprises a deletion of one or more C-terminal amino acids, such as a deletion of the residue corresponding to S482 of the wild-type sequence.

In any of the embodiments, the variant may be a long-acting variant, such as wherein the variant is conjugated to an albumin-binding peptide, an albumin-binding protein domain, human serum albumin, or an inert polypeptide, such as recombinant PEG (XTEN®), a homo-amino acid polymer (HAP), a proline-alanine serine polymer (PAS), or an elastin-like peptide (ELP). In specific embodiments, the long-acting variant is conjugated to polyethylene glycol (i.e., the variant is PEGylated).

In some embodiments, there are provided pharmaceutical compositions comprising a nicotine-degrading enzyme variant described herein and a pharmaceutically acceptable carrier. In some embodiments, the composition is formulated for injection or infusion. In some embodiments the composition is formulated for oral administration.

In some embodiments, there are provided methods of treating nicotine addiction or facilitating smoking cessation, comprising administering to a mammalian subject in need thereof a therapeutically effective amount of a nicotine-degrading enzyme variant or composition as described herein. In some embodiments, the mammalian subject is a human subject. In some embodiments, the nicotine addiction is associated with the ingestion of a nicotine product selected from tobacco products and electronic cigarettes.

In some embodiments, there are provided methods of treating nicotine poisoning, comprising administering to a mammalian subject in need thereof a therapeutically effective amount of a nicotine-degrading enzyme variant or composition as described herein. In some embodiments, the mammalian subject is a human subject, or, more specifically, a human child. In some embodiments, the nicotine poisoning is associated with the consumption of a nicotine product selected from tobacco products and electronic cigarettes.

Also provided are nicotine-degrading enzyme variants and compositions as described herein for use in treating nicotine addiction or facilitating smoking cessation.

Also provided are uses of nicotine-degrading enzyme variants and compositions as described herein in the manufacture of a medicament for the treatment of nicotine addiction or facilitation of smoking cessation.

The foregoing general description and following detailed description are exemplary and explanatory and are intended to provide further explanation of the invention.

BRIEF DESCRIPTION OF THE DRAWINGS

Figure 4E:
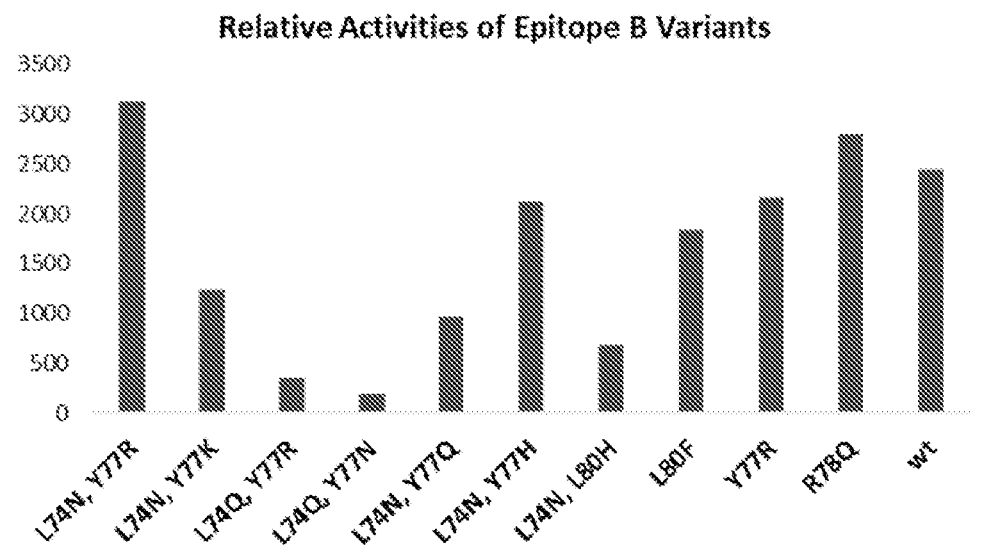

FIGS. 4A-E show the relative activities of specific NicA2 variants carrying mutations of Epitopes B (FIG. 4E), 1 (FIG. 4A), 2 (FIG. 4B), 3 (FIG. 4C) and 4 (FIG. 4D) (as listed in Table 3), predicted to reduce the immunogenic potential compared to wild-type NicA2.

DETAILED DESCRIPTION

Figure 1:
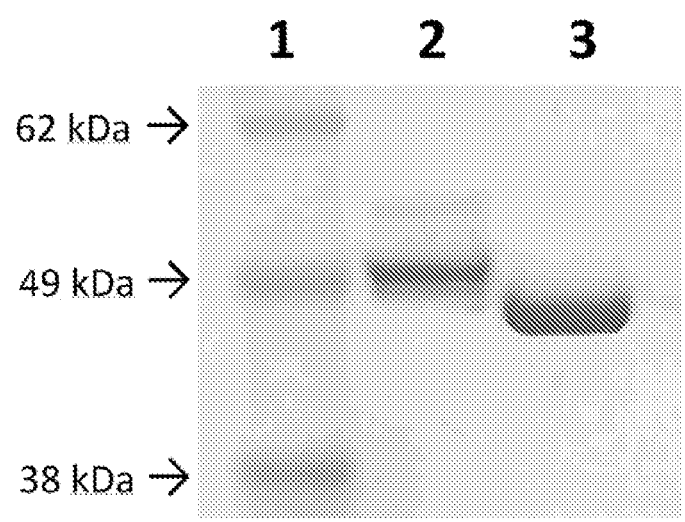
FIG. 1 shows SDS-PAGE analysis of His-tagged versions of wild-type NicA2 (SEQ ID NO:1) and NicA2Δ50 (SEQ ID NO:2). Lane 1: MW marker (Blue Plus2; Invitrogen); Lane 2: wild-type NicA2 (SEQ ID NO:1); and Lane 3: NicA2Δ50 (SEQ ID NO:2).

Described herein are nicotine-degrading enzyme variants that exhibit increased nicotine-degrading activity and/or decreased immunogenicity relative to the wild-type NicA2 or NOX enzymes, compositions comprising them, and methods using them, including methods for treating nicotine addiction and methods for facilitating nicotine cessation (e.g., smoking cessation) in a subject in need thereof.

I. Definitions

As used herein, the singular forms "a", "an" and "the" are used interchangeably and intended to include the plural forms as well and fall within each meaning, unless the context clearly indicates otherwise. Also, as used herein, "and/or" refers to and encompasses any and all possible permutations and combinations of one or more of the listed items.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the phrases "therapeutically effective amount" and "therapeutic level" mean a nicotine-degrading enzyme dosage or plasma concentration in a subject that provides the specific pharmacological effect for which the nicotine-degrading enzyme is administered to a subject in need of such treatment, i.e. to degrade nicotine in the subject, and/or treat nicotine addiction and/or facilitate smoking cessation and/or treat nicotine poisoning. It is emphasized that a therapeutically effective amount or therapeutic level of a nicotine-degrading enzyme will not always be effective in treating the nicotine addiction or facilitate smoking cessation of a given subject, even though such dosage is deemed to be a therapeutically effective amount by those of skill in the art. For convenience only, exemplary amounts are provided below.

Those skilled in the art can adjust such amounts in accordance with standard practices as needed to treat a specific subject. The therapeutically effective amount may vary based on the route of administration and dosage form, the age and weight of the subject, and/or the subject's condition, including the degree of nicotine addiction, amount of nicotine generally consumed/ingested by the subject, and/or the subject's plasma levels of nicotine at the time of treatment and/or the amount of nicotine localized in the brain at the time of treatment.

The terms "treatment" or "treating" as used herein with reference to nicotine addiction or smoking cessation refer to one or more of: reducing, ameliorating or eliminating one or more symptoms or effects of nicotine withdrawal; reducing the number of cigarettes or the amount of nicotine consumed by a subject; and/or reducing the subject's plasma levels of nicotine and/or reducing the amount of nicotine localized in specific tissues of the subject (e.g., brain/central nervous system, heart and vasculature, etc.).

The terms "treatment" or "treating" as used herein with reference to nicotine poisoning refer to reducing, ameliorating or eliminating one or more symptoms or effects of nicotine and/or reducing the subject's plasma levels of nicotine and/or reducing the amount of nicotine localized in specific tissues of the subject (e.g., brain/central nervous system, heart and vasculature, etc.).

The terms "individual," "subject," and "patient" are used interchangeably herein, and refer to any individual mammal subject, e.g., bovine, canine, feline, equine, or human.

In accordance with FDA guidance, as used herein, "child" refers to a human subject from 0 through about 19 years of age. A child can be a subject that begins a course of treatment prior to turning about 19 years of age, even if the subject continues treatment beyond 19 years of age.

II. Nicotine, Nicotine Addiction, and Nicotine Toxicity

Nicotine is a nitrogen-containing chemical made by several types of plants including tobacco and other members of the nightshade family. When humans, mammals and most other types of animals are exposed to nicotine, it increases their heart rate, heart muscle oxygen consumption rate, and heart stroke volume. The consumption of nicotine is also linked to raised alertness, euphoria, and a sensation of being relaxed. However, nicotine is highly addictive.

By binding to nicotinic acetylcholine receptors in the brain, nicotine elicits its psychoactive effects and increases the levels of several neurotransmitters in various brain structures. Nicotine has a higher affinity for nicotinic receptors in the brain than those in skeletal muscle, though at toxic doses it can induce contractions and respiratory paralysis. Nicotine's selectivity is thought to be due to a particular amino acid difference on these receptor subtypes. The structure of nicotine is shown in Formula I below.

Formula I

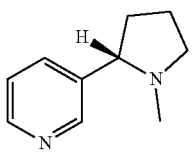

People who regularly consume nicotine and then suddenly stop experience withdrawal symptoms, which may include cravings, a sense of emptiness, anxiety, depression, moodiness, irritability, and inattentiveness. The American Heart Association says that nicotine (from smoking tobacco) is one of the hardest substances to quit—at least as hard as heroin.

Nicotine poisoning can occur when an individual consumes loose tobacco, cigarettes, nicotine gum, patches, or the "e-liquid" of electronic cigarettes (e.g., the nicotine-containing liquid that is used in electronic cigarettes and other vaporizing devices) or other products containing tobacco or tobacco extracts, or other products, supplies or intermediates containing nicotine. Indeed, a recent study showed that the incidence of nicotine poisoning from exposure to e-cigarettes increased 1492.9% between January 2012 and April 2015 (Kamboj et al. PEDIATRICS 137(6): e20160041 (2016)). Although exposure can occur through inhalation of tobacco smoke (either primary or second hand), nicotine poisoning or nicotine overdose more commonly results when a subject (typically a child) ingests nicotine, for example by chewing or ingesting nicotine gum, ingesting cigarettes or other tobacco leaf products, ingesting nicotine patches, or ingesting e-liquid. Additionally, nicotine can be dermally absorbed, and therefore nicotine poisoning can result from toxic levels of nicotine coming into direct contact with the skin.

Nicotine poisoning can produce neurological symptoms (convulsions, coma, depression, confusion, fainting, headache), cardiovascular symptoms (rapid heartbeat, high blood pressure), respiratory symptoms (difficulty breathing, rapid breathing), gastrointestinal symptoms (increased salivation, abdominal cramps, vomiting), and musculoskeletal symptoms (Muscular twitching, weakness), as well as death.

III. Nicotine-Degrading Enzyme Variants

Described herein are nicotine-degrading enzyme variants comprising an amino acid sequence that is a variant of the amino acid sequence of the wild-type NicA2 or NOX enzyme set forth in SEQ ID NO: 1 or SEQ ID NO: 57, respectively, wherein the variant sequence has at least one substitution, addition, or deletion relative to SEQ ID NO: 1 or SEQ ID NO: 57 that increases the nicotine-degrading activity and/or decreases the immunogenicity of the variant relative to the wild-type NicA2 or NOX enzyme, respectively.

NicA2 (nicotine oxidoreductase; PPS_4081; GenBank accession number: AEJ14620.1), was isolated from *Pseudomonas putida* strain S16. See, e.g., Tang et al., PLoS GENETICS, 9(10): e1003923 (2013). The activity of NicA2 is the first committed step of S16's degradation of nicotine, catalyzing the oxidation of nicotine to N-methylmyosmine. It is reported to be an essential enzyme in the *P. putida* S16 metabolic cascade responsible for breaking down nicotine. A structural analysis of the wild-type NicA2 enzyme has been reported in Tararina et al., *Biochem.* 55:6595-98 (2016).

NOX (nicotine amine oxidase; GenBank accession number: AGH68979.1) has been isolated from *Pseudomonas* sp. HZN6 (See, e.g., Qiu et al., Appl. Environ. Microbiol. 78, 2154-2160 (2012); Qiu et al., Appl. Environ. Microbiol. 79, 2164-2171 (2013)). NOX is closely related to NicA2, with an amino acid identity of 83%. NOX was reported to have a catalytic activity like NicA2, degrading nicotine to N-methylmyosmine.

The present disclosure provides variants of wild-type NicA2 and NOX with improved activity and/or decreased immunogenicity. In some embodiments, the disclosed variants may have an amino acid identity that is about 80, about 85, about 90, about 95, about 96, about 97, about 98, or about 99 percent of wild-type NicA2 or NOX. In some embodiments, the disclosed variants may share about 80, about 85, about 90, about 95, about 96, about 97, about 98, or about 99 percent homology with wild-type NicA2 or NOX. For instance, in some embodiments, the disclosed variants may comprise the amino acids residues conserved between NicA2 and NOX.

The amino acid sequence of wild-type NicA2, wild-type NOX, and exemplary variants thereof are set forth in Table 1 below. The disclosed variants were produced with a linker and His-tag (GGGGSGSGHHHHHH, SEQ ID NO: 139) at the C-terminal end, which was subsequently removed. The His-tag was used to assist in purification of the variants, but other means or methods of purification that do not require a His-tag may also be used.

TABLE 1

Amino Acid Sequences of NicA2 & NOX and Exemplary Variants

| Enzyme | SEQ ID NO. | Sequence |
|---|---|---|
| Wild-Type NicA2 | 1 | M*SDKTKTNEGFSRRSFIGSAAVVTAGVAGLGAIDAASATQKTNRASTV KGGFDYDVVVVGGGFAGATAARECGLQGYRTLLLEARSRLGGRTFTSR FAGQEIEFGGAWVHWLQPHVWIMQRYGLGVVEDPLTNLDKTLIMYN |

TABLE 1-continued

Amino Acid Sequences of NicA2 & NOX and Exemplary Variants

| Enzyme | SEQ ID NO. | Sequence |
|---|---|---|
| | | DGSVESISPDEFGKNIRIAFEKLCHDAWEVFPRPHEPMFTERARELDKSSV |
| | | LDRIKTLGLSRLQQAQINSYMALYAGETTDKFGLPGVLKLFACGGWNYD |
| | | AFMDTETHYRIQGGTIGLINAMLTDSGAEVRMSVPVTAVEQVNGGVKIK |
| | | TDDDEIITAGVVVMTVPLNTYKHIGFTPALSKGKQRFIKEGQLSKGAKLY |
| | | VHVKQNLGRVFAFADEQQPLNWVQTHDYSDELGTILSITIARKETIDVN |
| | | DRDAVTREVQKMFPGVEVLGTAAYDWTADPFSLGAWAAYGVGQLSRL |
| | | KDLQAAEGRILFAGAETSNGWHANIDGAVESGLRAGREVKQLLS**<br>† |
| NicA2Δ50<br>(N-terminal deletion of residues 1-50) | 2 | GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2Δ25<br>(N-terminal deletion of residues 1-25) | 3 | GVAGLGAIDAASATQKTNRASTVKGGFDYDVVVVGGGFAGATAARECG<br>LQGYRTLLLEARSRLGGRTFTSRFAGQEIEFGGAWVHWLQPHVWAEMQ<br>RYGLGVVEDPLTNLDKTLIMYNDGSVESISPDEFGKNIRIAFEKLCHDAW<br>EVFPRPHEPMFTERARELDKSSVLDRIKTLGLSRLQQAQINSYMALYAGE<br>TTDKFGLPGVLKLFACGGWNYDAFMDTETHYRIQGGTIGLINAMLTDSG<br>AEVRMSVPVTAVEQVNGGVKIKTDDDEIITAGVVVMTVPLNTYKHIGFT<br>PALSKGKQRFIKEGQLSKGAKLYVHVKQNLGRVFAFADEQQPLNWVQT<br>HDYSDELGTILSITIARKETIDVNDRDAVTREVQKMFPGVEVLGTAAYDW<br>TADPFSLGAWAAYGVGQLSRLKDLQAAEGRILFAGAETSNGWHANIDG<br>AVESGLRAGREVKQLLS |
| NicA2Δ38<br>(N-terminal deletion of residues 1-38) | 4 | TQKTNRASTVKGGFDYDVVVVGGGFAGATAARECGLQGYRTLLLEARS<br>RLGGRTFTSRFAGQEIEFGGAWVHWLQPHVWAEMQRYGLGVVEDPLTN<br>LDKTLEVIYNDGSVESISPDEFGKNIRIAFEKLCHDAWEVFPRPHEPMFTER<br>ARELDKSSVLDRIKTLGLSRLQQAQINSYMALYAGETTDKFGLPGVLKLF<br>ACGGWNYDAFMDTETHYRIQGGTIGLINAMLTDSGAEVRMSVPVTAVE<br>QVNGGVKIKTDDDEIITAGVVVMTVPLNTYKHIGFTPALSKGKQRFIKEG<br>QLSKGAKLYVHVKQNLGRVFAFADEQQPLNWVQTHDYSDELGTILSITI<br>ARKETIDVNDRDAVTREVQKMFPGVEVLGTAAYDWTADPFSLGAWAA<br>YGVGQLSRLKDLQAAEGRILFAGAETSNGWHANIDGAVESGLRAGREVK<br>QLLS |
| NicA2Δ50<br>W427Q<br>(W427Q substitution; N-terminal deletion of residues 1-50) | 5 | GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAQAAYGVGQLSRLKDLQ<br>AAEGRILFAGAETSNGWHANIDGAVESGLRAGREVKQLLS |
| NicA2Δ50<br>W427E<br>(W427E substitution; N-terminal deletion of residues 1-50) | 6 | GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAEAAYGVGQLSRLKDLQA<br>AEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 W427S (W427S substitution; N-terminal deletion of residues 1-50) | 7 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGASAAYGVGQLSRLKDLQA AEGRILFAGAETSNGWHANIDGAVESGLRAGREVKQLLS |
| NicA2Δ50 W427M (W427M substitution; N-terminal deletion of residues 1-50) | 8 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAMAAYGVGQLSRLKDLQ AAEGRILFAGAETSNGWHANIDGAVESGLRAGREVKQLLS |
| NicA2Δ50 R91A (R91A substitution; N-terminal deletion of residues 1-50) | 9 | GFDYDVVVVGGGFAGATAARECGQGYRTLLLEARSRLGGATFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 R91Q (R91Q substitution; N-terminal deletion of residues 1-50) | 10 | GFDYDVVVVGGGFAGATAARECGLQGYRTLLLEARSRLGGQTFTSRFA GQEIEFGGAWVHWLQPHVWAEMQRYGLGVVEDPLTNLDKTLIIVIYNDG SVESTSPDEFGKNIRIAFEKLCHDAWEVFPRPHEPMFTERARELDKSSVLD RIKTLGLSRLQQAQINSYMALYAGETTDKFGLPGVLKLFACGGWNYDAF MDTETHYRIQGGTIGLINAMLTDSGAEVRMSVPVTAVEQVNGGVKIKTD DDEIITAGVVVMTVPLNTYKHIGFTPALSKGKQRFIKEGQLSKGAKLYVH VKQNLGRVFAFADEQQPLNWVQTHDYSDELGTILSITIARKETIDVNDRD AVTREVQKMFPGVEVLGTAAYDWTADPFSLGAWAAYGVGQLSRLKDL QAAEGRILFAGAETSNGWHANIDGAVESGLRAGREVKQLLS |
| NicA2Δ50 R91F (R91F substitution; N-terminal deletion of residues 1-50) | 11 | GFDYDVVVVGGGFAGATAARECGLQGYRTLLLEARSRLGGFTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 R91G (R91G substitution; N-terminal deletion of residues 1-50) | 12 | GFDYDVVVVGGGFAGATAARECGLQGYRTLLLEARSRLGGGTFTSRFA GQEIEFGGAWVHWLQPHVWAEMQRYGLGVVEDPLTNLDKTLEVIYNDG SVESTSPDEFGKNIRIAFEKLCHDAWEVFPRPHEPMFTERARELDKSSVLD RIKTLGLSRLQQAQINSYMALYAGETTDKFGLPGVLKLFACGGWNYDAF MDTETHYRIQGGTIGLINAMLTDSGAEVRMSVPVTAVEQVNGGVKIKTD DDEIITAGVVVMTVPLNTYKHIGFTPALSKGKQRFIKEGQLSKGAKLYVH VKQNLGRVFAFADEQQPLNWVQTHDYSDELGTILSITIARKETIDVNDRD AVTREVQKMFPGVEVLGTAAYDWTADPFSLGAWAAYGVGQLSRLKDL QAAEGRILFAGAETSNGWHANIDGAVESGLRAGREVKQLLS |
| NicA2Δ50 R91T (R91T substitution; N-terminal deletion of residues 1-50) | 13 | GFDYDVVVVGGGFAGATAARECGLQGYRTLLLEARSRLGGTTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 R91L (R91L substitution; N-terminal deletion of residues 1-50) | 14 | GFDYDVVVVGGGFAGATAARECGLQGYRTLLLEARSRLGGLTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 R91S (R91S substitution; N-terminal deletion of residues 1-50) | 15 | GFDYDVVVVGGGFAGATAARECGLQGYRTLLLEARSRLGGSTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 R91N (R91N substitution; N-terminal deletion of residues 1-50) | 16 | GFDYDVVVVGGGFAGATAARECGLQGYRTLLLEARSRLGGNTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T250G (T250G substitution; N-terminal deletion of residues 1-50) | 17 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTEGHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T250L (T250L substitution; N-terminal deletion of residues 1-50) | 18 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTELHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T250R (T250R substitution; N-terminal deletion of residues 1-50) | 19 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTERHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T250V (T250V substitution; N-terminal deletion of residues 1-50) | 20 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTEVHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 K340P (K340P substitution; N-terminal deletion of residues 1-50) | 21 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAPLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 K340I (K340I substitution; N-terminal deletion of residues 1-50) | 22 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAILYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 K340V (K340V substitution; N-terminal deletion of residues 1-50) | 23 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAVLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 K340D (K340D substitution; N-terminal deletion of residues 1-50) | 24 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGADLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 K340E (K340E substitution; N-terminal deletion of residues 1-50) | 25 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAELYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 Q366K (Q366K substitution; N-terminal deletion of residues 1-50) | 26 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWKTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 Q366E (Q366E substitution; N-terminal deletion of residues 1-50) | 27 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWETHDYSDELGTILSITIARKET1DVNDRDA PGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 Q366V (Q366V substitution; N-terminal deletion of residues 1-50) | 28 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVVTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 Q366L (Q366L substitution; N-terminal deletion of residues 1-50) | 29 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVLTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 Q366I (Q366I substitution; N-terminal deletion of residues 1-50) | 30 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVITHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 Q366Y (Q366Y substitution; N-terminal deletion of residues 1-50) | 31 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVYTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381P (T381P substitution; N-terminal deletion of residues 1-50) | 32 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSIPIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381I (T381I substitution; N-terminal deletion of residues 1-50) | 33 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSIIIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381V (T381V substitution; N-terminal deletion of residues 1-50) | 34 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSIVIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 T381Q (T381Q substitution; N-terminal deletion of residues 1-50) | 35 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSIQIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381N (T381N substitution; N-terminal deletion of residues 1-50) | 36 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSINIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381L (T381L substitution; N-terminal deletion of residues 1-50) | 37 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSILIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 T381M (T381M substitution; N-terminal deletion of residues 1-50) | 38 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSIMIARKETIDVNDRD AVTREVQKMFPGVEVLGTAAYDWTADPFSLGAWAAYGVGQLSRLKDL QAAEGRILFAGAETSNGWHANIDGAVESGLRAGREVKQLLS |
| NicA2Δ50 N462L (N462L substitution; N-terminal deletion of residues 1-50) | 39 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHALIDGAVESGLRAGREVKQLLS |
| NicA2Δ50 N462Y (N462Y substitution; N-terminal deletion of residues 1-50) | 40 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHAYIDGAVESGLRAGREVKQLLS |
| NicA2Δ50 N462S (N462S substitution; N-terminal deletion of residues 1-50) | 41 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHASIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 N462F (N462F substitution; N-terminal deletion of residues 1-50) | 42 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHAFIDGAVESGLRAGREVKQLLS |
| NicA2Δ50 N462G (N462G substitution; N-terminal deletion of residues 1-50) | 43 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHAGIDGAVESGLRAGREVKQLLS |
| NicA2Δ50 N462E (N462E substitution; N-terminal deletion of residues 1-50) | 44 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHAEIDGAVESGLRAGREVKQLLS |
| NicA2Δ50 N462A (N462A substitution; N-terminal deletion of residues 1-50) | 45 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHAAIDGAVESGLRAGREVKQLLS |
| NicA2Δ50 I463F (I463F substitution; N-terminal deletion of residues 1-50) | 46 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANFDGAVESGLRAGREVKQLLS |
| NicA2Δ50 I463Y (I463Y substitution; N-terminal deletion of residues 1-50) | 47 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANYDGAVESGLRAGREVKQLLS |
| NicA2Δ50 I463A (I463A substitution; N-terminal deletion of residues 1-50) | 48 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANADGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 I463V (I463V substitution; N-terminal deletion of residues 1-50) | 49 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANVDGAVESGLRAGREVKQLLS |
| NicA2Δ50 I463L (I463L substitution; N-terminal deletion of residues 1-50) | 50 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANLDGAVESGLRAGREVKQLLS |
| NicA2Δ50 L217Q (L217Q substitution; N-terminal deletion of residues 1-50) | 51 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMAQYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 L217G (L217G substitution; N-terminal deletion of residues 1-50) | 52 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMAGYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 L217E (L217E substitution; N-terminal deletion of residues 1-50) | 53 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMAEYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 L217I (L217I substitution; N-terminal deletion of residues 1-50) | 54 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMAIYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ50 L217C (L217C substitution; N-terminal deletion of residues 1-50) | 55 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMACYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKET1DVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 L217S (L217S substitution; N-terminal deletion of residues 1-50) | 56 | GFDYDVVVVGGGFAGATAARECGLQGYRTLLLEARSRLGGRTFTSRFAG QEIEFGGAWVHWLQPHVVAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMASYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| Wild-Type NOX | 57 | MDEKRNNGLSRRSFIGGAAVVTAGAAGLGLIGSANATENGTSKRATGFD YDVIVVGGGFAGATAARECGHQGYKTLLLEARSRLGGRTFTSHFAGQEI EFGGAWVHWLQPHVWSEMQRYGLGVVEDPLTNLDKTLVMYNDGSVED LPPEVFGTNIQVAFEKMCHDAWEAFPRPHEPMFTERARKLDKMSVLDRI NQLELTRAQRAELNSYMALYGGETTDKYGLPGVLKLFACGGWNYNAF MDTETHYRIEGGTIGLINAMLADSGAEVRLNMPVISVEQLNGGVRVETD DGETITAGTIIIVITVPLNTYRHINFTPALSEGKQRFIQEGQLSKGAKLYVHV KENLGRVFAFADEQQPLNWVQTHDYGDELGTILSITIARAETIDVNDRDA VTREIRKLFPGVEVLGIAAYDWTADPFSLGAWAAYGVGQLSRLTDLQQP EGRILFAGAETSNGWHANIDGAVESGLRAGREAKEIL |
| NOXW423A (W423A Substitution) | 58 | MDEKRNNGLSRRSFIGGAAVVTAGAAGLGLIGSANATENGTSKRATGFD YDVIVVGGGFAGATAARECGHQGYKTLLLEARSRLGGRTFTSHFAGQEI EFGGAWVHWLQPHVWSEMQRYGLGVVEDPLTNLDKTLVMYNDGSVED LPPEVFGTNIQVAFEKMCHDAWEAFPRPHEPMFTERARKLDKMSVLDRI NQLELTRAQRAELNSYMALYGGETTDKYGLPGVLKLFACGGWNYNAF MDTETHYRIEGGTIGLINAMLADSGAEVRLNMPVISVEQLNGGVRVETD DGETITAGTIIIVITVPLNTYRHINFTPALSEGKQRFIQEGQLSKGAKLYVHV KENLGRVFAFADEQQPLNWVQTHDYGDELGTILSITIARAETIDVNDRDA VTREIRKLFPGVEVLGIAAYDWTADPFSLGAAAAYGVGQLSRLTDLQQP EGRILFAGAETSNGWHANIDGAVESGLRAGREAKEIL |
| NOXW423S (W423S Substitution) | 59 | MDEKRNNGLSRRSFIGGAAVVTAGAAGLGLIGSANATENGTSKRATGFD YDVIVVGGGFAGATAARECGHQGYKTLLLEARSRLGGRTFTSHFAGQEI EFGGAWVHWLQPHVWSEMQRYGLGVVEDPLTNLDKTLVMYNDGSVED LPPEVFGTNIQVAFEKMCHDAWEAFPRPHEPMFTERARKLDKMSVLDRI NQLELTRAQRAELNSYMALYGGETTDKYGLPGVLKLFACGGWNYNAF MDTETHYRIEGGTIGLINAMLADSGAEVRLNMPVISVEQLNGGVRVETD DGETITAGTIIIVITVPLNTYRHINFTPALSEGKQRFIQEGQLSKGAKLYVHV KENLGRVFAFADEQQPLNWVQTHDYGDELGTILSITIARAETIDVNDRDA VTREIRKLFPGVEVLGIAAYDWTADPFSLGASAAYGVGQLSRLTDLQQPE GRILFAGAETSNGWHANIDGAVESGLRAGREAKEIL |
| NOXW423E (W423E Substitution) | 60 | MDEKRNNGLSRRSFIGGAAVVTAGAAGLGLIGSANATENGTSKRATGFD YDVIVVGGGFAGATAARECGHQGYKTLLLEARSRLGGRTFTSHFAGQEI EFGGAWVHWLQPHVWSEMQRYGLGVVEDPLTNLDKTLVMYNDGSVED LPPEVFGTNIQVAFEKMCHDAWEAFPRPHEPMFTERARKLDKMSVLDRI NQLELTRAQRAELNSYMALYGGETTDKYGLPGVLKLFACGGWNYNAF MDTETHYRIEGGTIGLINAMLADSGAEVRLNMPVISVEQLNGGVRVETD DGETITAGTIIIVITVPLNTYRHINFTPALSEGKQRFIQEGQLSKGAKLYVHV KENLGRVFAFADEQQPLNWVQTHDYGDELGTILSITIARAETIDVNDRDA VTREIRKLFPGVEVLGIAAYDWTADPFSLGAEAAYGVGQLSRLTDLQQPE GRILFAGAETSNGWHANIDGAVESGLRAGREAKEIL |
| NOXW423H (W423H Substitution) | 61 | MDEKRNNGLSRRSFIGGAAVVTAGAAGLGLIGSANATENGTSKRATGFD YDVIVVGGGFAGATAARECGHQGYKTLLLEARSRLGGRTFTSHFAGQEI EFGGAWVHWLQPHVWSEMQRYGLGVVEDPLTNLDKTLVMYNDGSVED LPPEVFGTNIQVAFEKMCHDAWEAFPRPHEPMFTERARKLDKMSVLDRI NQLELTRAQRAELNSYMALYGGETTDKYGLPGVLKLFACGGWNYNAF MDTETHYRIEGGTIGLINAMLADSGAEVRLNMPVISVEQLNGGVRVETD DGETITAGTIEVITVPLNTYRHINFTPALSEGKQRFIQEGQLSKGAKLYVHV KENLGRVFAFADEQQPLNWVQTHDYGDELGTILSITIARAETIDVNDRDA VTREIRKLFPGVEVLGIAAYDWTADPFSLGAHAAYGVGQLSRLTDLQQP EGRILFAGAETSNGWHANIDGAVESGLRAGREAKEIL |

TABLE 1-continued

Amino Acid Sequences of NicA2 & NOX and Exemplary Variants

| Enzyme | SEQ ID NO. | Sequence |
|---|---|---|
| NicA2Δ50 W427Q; I262A (W427Q & I262A substitution; N-terminal deletion of residues 1-50) | 62 | GFDYDVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLANAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAQAAYGVGQLSRLKDLQ AAEGRILFAGAETSNGWHANIDGAVESGLRAGREVKQLLS |
| NicA2Δ50 W427Q; I262T;N263R (W427Q, I262T & N263R substitution; N-terminal deletion of residues 1 50) | 63 | GFDYDVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLTRAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAQAAYGVGQLSRLKDLQ AAEGRILFAGAETSNGWHANIDGAVESGLRAGREVKQLLS |
| NicA2 A107R (A107R substitution) | 124 | SDKTKTNEGFSRRSFIGSAAVVTAGVAGLGAIDAASATQKTNRASTVKG GFDYDVVVGGGFAGATAARECGLQGYRTLLLEARSRLGGRTFTSRFAG QEIEFGGRWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2A107K (A107K substitution) | 125 | SDKTKTNEGFSRRSFIGSAAVVTAGVAGLGAIDAASATQKTNRASTVKG GFDYDVVVGGGFAGATAARECGLQGYRTLLLEARSRLGGRTFTSRFAG QEIEFGGKWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2A107T (A107T substitution) | 126 | SDKTKTNEGFSRRSFIGSAAVVTAGVAGLGAIDAASATQKTNRASTVKG GFDYDVVVGGGFAGATAARECGLQGYRTLLLEARSRLGGRTFTSRFAG QEIEFGGTWVHWLQPHVWAEMQRYGLGVVEDPLTNLDKTLIIVIYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F355C (F355C substitution) | 127 | SDKTKTNEGFSRRSFIGSAAVVTAGVAGLGAIDAASATQKTNRASTVKG GFDYDVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFACADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2F355V (F355V substitution) | 128 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAVADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2R91Q (R91Q substitution) | 129 | SDKTKTNEGFSRRSFIGSAAVVTAGVAGLGAIDAASATQKTNRASTVKG<br>GFDYDVVVVGGGFAGATAARECGLQGYRTLLLEARSRLGGQTFTSRFA<br>GQEIEFGGAWVHWLQPHVWAEMQRYGLGVVEDPLTNLDKTLIVIYNDG<br>SVESTSPDEFGKNIRIAFEKLCHDAWEVFPRPHEPMFTERARELDKSSVLD<br>RIKTLGLSRLQQAQINSYMALYAGETTDKFGLPGVLKLFACGGWNYDAF<br>MDTETHYRIQGGTIGLINAMLTDSGAEVRMSVPVTAVEQVNGGVKIKTD<br>DDEIITAGVVVMTVPLNTYKHIGFTPALSKGKQRFIKEGQLSKGAKLYVH<br>VKQNLGRVFAFADEQQPLNWVQTHDYSDELGTILSITIARKETIDVNDRD<br>AVTREVQKMFPGVEVLGTAAYDWTADPFSLGAWAAYGVGQLSRLKDL<br>QAAEGRILFAGAETSNGWHANIDGAVESGLRAGREVKQLLS |
| NicA2Q366K (Q336K substitution) | 130 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVKTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2T381V (T381V substitution) | 131 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSIVIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2N462L (N462L substitution) | 132 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHALIDGAVESGLRAGREVKQLLS |
| NicA2N462Y (N462Y substitution) | 133 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHAYIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2Δ50 A107R (A107R substitution; N-terminal deletion of residues 1 50) | 134 | GFDYDVVVVGGGFAGATAARECGLQGYRTLLLEARSRLGGRTFTSRFAG QEIEFGGRWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2W427R (W427R substitution) | 135 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGARAAYGVGQLSRLKDLQA AEGRILFAGAETSNGWHANIDGAVESGLRAGREVKQLLS |
| NicA2T250P (T250P substitution) | 136 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTEPHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2W427H; N462F (W427H & N462F substitution) | 137 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAHAAYGVGQLSRLKDLQ AAEGRILFAGAETSNGWHAFIDGAVESGLRAGREVKQLLS |
| NicA2W427L; N462M (W427L & N462M substitution) | 138 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGALAAYGVGQLSRLKDLQA AEGRILFAGAETSNGWHAMIDGAVESGLRAGREVKQLLS |
| NicA2F104L (F104L substitution) | 140 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIELGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |

TABLE 1-continued

Amino Acid Sequences of NicA2 & NOX and Exemplary Variants

| Enzyme | SEQ ID NO. | Sequence |
|---|---|---|
| NicA2G106S (G106S substitution) | 141 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGSAWVHWLQPHVWAEMQRYGLGVVEDPLTNLDKTLIMYNDGSV ESISPDEFGKNIRIAFEKLCHDAWEVFPRPHEPMFTERARELDKSSVLDRIK TLGLSRLQQAQINSYMALYAGETTDKFGLPGVLKLFACGGWNYDAFMD TETHYRIQGGTIGLINAMLTDSGAEVRMSVPVTAVEQVNGGVKIKTDDD EIITAGVVVMTVPLNTYKHIGFTPALSKGKQRFIKEGQLSKGAKLYVHVK QNLGRVFAFADEQQPLNWVQTHDYSDELGTILSITIARKETIDVNDRDAV TREVQKMFPGVEVLGTAAYDWTADPFSLGAWAAYGVGQLSRLKDLQA AEGRILFAGAETSNGWHANIDGAVESGLRAGREVKQLLS |
| NicA2A107H (A107H substitution) | 142 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGHWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2A107P (A107P substitution) | 143 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGPWVHWLQPHVWAEMQRYGLGVVEDPLTNLDKTLIVIYNDGSV ESISPDEFGKNIRIAFEKLCHDAWEVFPRPHEPMFTERARELDKSSVLDRIK TLGLSRLQQAQINSYMALYAGETTDKFGLPGVLKLFACGGWNYDAFMD TETHYRIQGGTIGLINAMLTDSGAEVRMSVPVTAVEQVNGGVKIKTDDD EIITAGVVVMTVPLNTYKHIGFTPALSKGKQRFIKEGQLSKGAKLYVHVK QNLGRVFAFADEQQPLNWVQTHDYSDELGTILSITIARKETIDVNDRDAV TREVQKMFPGVEVLGTAAYDWTADPFSLGAWAAYGVGQLSRLKDLQA AEGRILFAGAETSNGWHANIDGAVESGLRAGREVKQLLS |

*The N-terminal methionine residue (M) of SEQ ID NO: 1 is cleaved off in the purified product; however all amino acid position designations disclosed herein take the methionine residue into account for the purpose of maintaining amino acid numbering conventions used in the art for the wild-type NicA2 sequence.
**Underlined sequences in wild-type NicA2 identify the six highest ranked immunogenic regions identified by the online MHC-II Binding Predictions tool on the Immune Epitope Database and Analysis Resource website (iedb.org) using the specific human MHC allele HLA DRB1*0401
†Residues highlighted in grey were identified as MHCII epitopes as disclosed in Example 2.

As noted above the nicotine-degrading enzyme variants may exhibit increased nicotine-degrading activity and/or decreased immunogenicity relative to the wild-type NicA2 enzyme. The variants may comprise one or more mutations to the amino acid sequence of wild-type NicA2, including one or more deletions, additions, or substitutions. A substitution mutation may be "conservative" or "non-conservative." "Conservative" refers to a substitution within the same family of amino acids, while "non-conservative" refers to substitutions across families of amino acids. Families of amino acids and "conservative" and "non-conservative" substitutions relative thereto are known in the art. For example, the naturally occurring amino acids may be divided into the following four families and conservative substitutions will take place within those families, while non-conservative substitutions will take place across different families.

1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

Figure 3:
FIG. 3 shows the residues around the active site in the NicA2 crystal structure (adapted from Tararina et al., *Biochem.* 55:6595-98 (2016)). Shell one is shown in dark grey and shell two is shown in light grey. The residues making up the first and second shell are shown in Table 2.
Figure 4A:
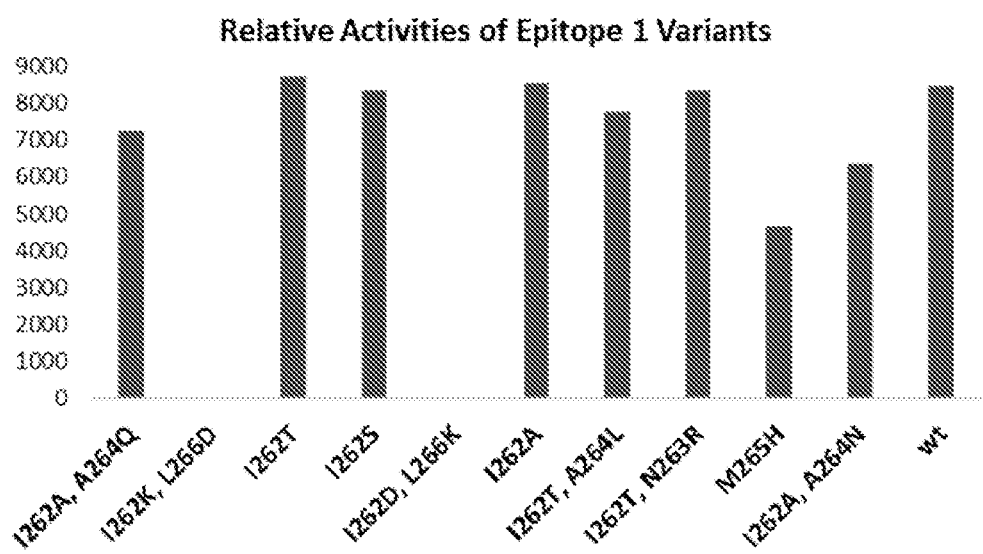
Figure 4B:
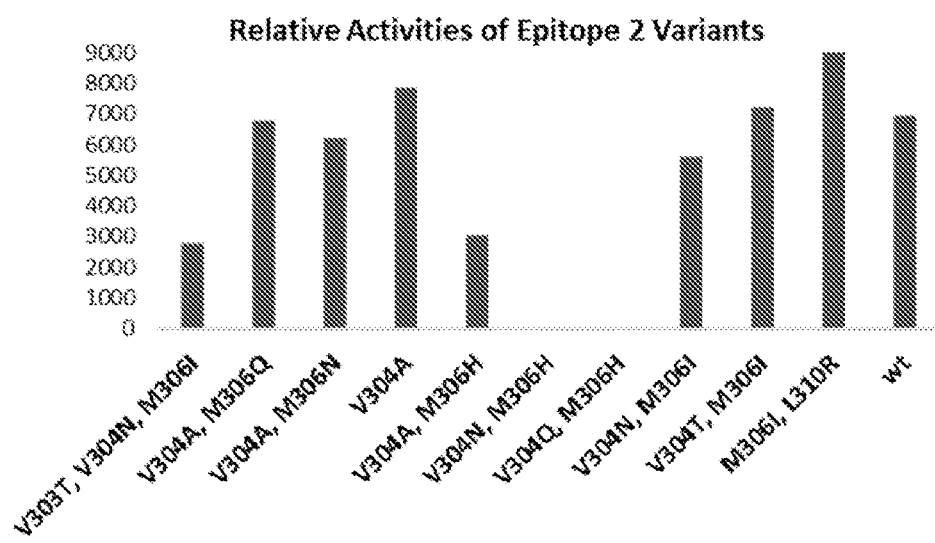
Figure 4C:
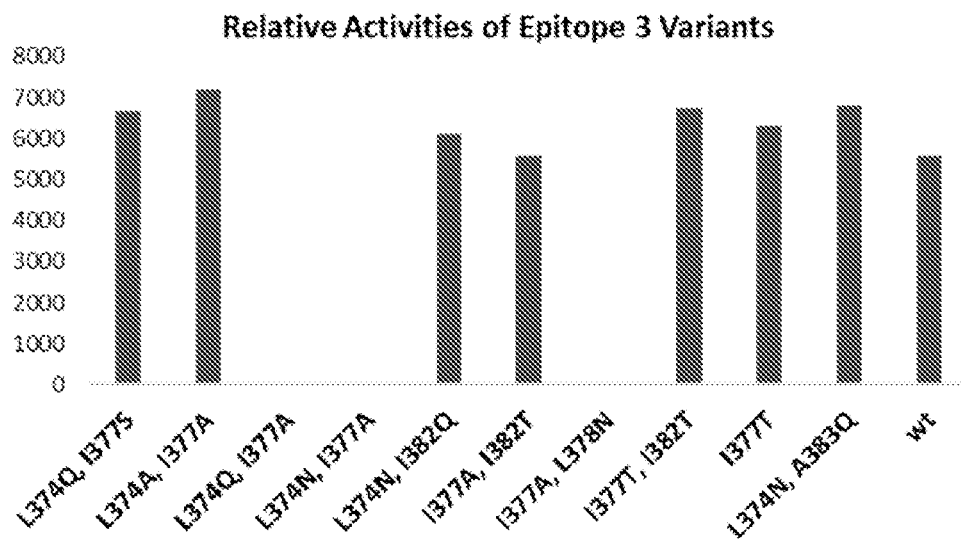
Figure 4D:
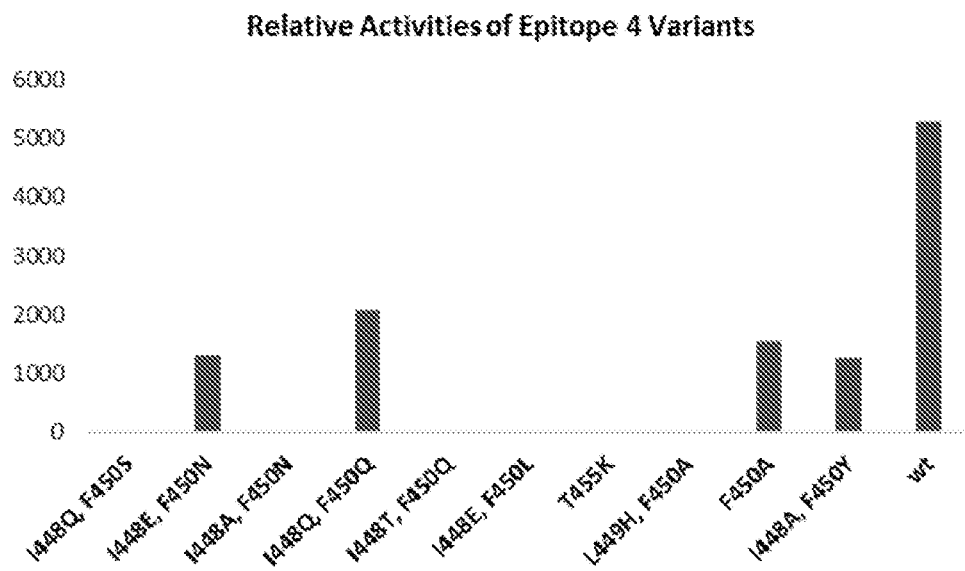

In some embodiments, the nicotine-degrading enzyme variants comprise one or more mutations in an active site of the wild-type NicA2 enzyme relevant to its nicotine-degrading activity, such as a mutation at one or more positions selected from any one of amino acid residues 90-93, 95, 102-109, 113, 116, 130, 132, 138, 155, 159, 210, 213-215, 217-220, 234, 245, 246, 248-251, 253, 254, 258, 334, 336, 339-342, 353, 355, 363-367, 378-382, 415-418, 423-429, 459-463, 465, or 466 of SEQ ID NO:1, such as one or more conservative substitutions, non-conservative substitutions, additions, or deletions in positions listed in Table 2 and shown on the structure in FIG. 3. The Shell One residues identified in Table 2 make up the cavity surface, while the Shell Two residues contacting Shell One (see FIG. 3). For instance, in some embodiments, the disclosed nicotine-degrading enzyme variants can comprise at least one substitution at amino acid position 91, 104, 106, 107, 217, 250, 340, 355, 366, 381, 427, 462, or 463 of SEQ ID NO:1. In some embodiments, the variants may comprise one, two, or three or more substitutions.

TABLE 2

NicA2 Active Site Residues

| Shell One | Shell Two |
|---|---|
| ARG91 | GLY90 |
| PHE104 | THR92 |
| GLY105 | PHE93 |
| GLY106 | SER95 |
| ALA107 | ILE102 |
| TRP108 | GLU103 |
| TYR214 | VAL109 |
| TYR218 | GLN113 |
| GLU249 | VAL116 |
| THR250 | ASP130 |
| LYS340 | LEU132 |
| PHE355 | THR138 |
| TRP364 | PHE155 |
| GLN366 | ILE159 |
| THR381 | GLN210 |
| TRP417 | SER213 |
| ALA426 | MET215 |
| TRP427 | LEU217 |
| ALA461 | ALA219 |
| ASN462 | GLY220 |
| ILE463 | LEU234 |
|  | PHE245 |
|  | MET246 |
|  | THR248 |
|  | HIS251 |
|  | ARG253 |
|  | ILE254 |
|  | THR258 |
|  | GLN334 |
|  | SER336 |
|  | ALA339 |
|  | LEU341 |
|  | TYR342 |
|  | PHE353 |
|  | ASN363 |
|  | VAL365 |
|  | THR367 |
|  | LEU378 |
|  | SER379 |
|  | ILE380 |
|  | ILE382 |
|  | TYR415 |
|  | ASP416 |
|  | THR418 |
|  | SER423 |
|  | LEU424 |
|  | GLY425 |
|  | ALA428 |
|  | ALA429 |
|  | TRP459 |
|  | HIS460 |
|  | GLY465 |
|  | ALA466 |

Active site based on published crystal structure from Tararina et al., 2016.
Amino acid residue numbers correspond to SEQ ID NO: 1.

In some embodiments, the nicotine-degrading enzyme variants comprise one or more mutations to the wild-type NOX enzyme relevant to its nicotine-degrading activity, such as a mutation at amino acid residue 423 of SEQ ID NO: 57, such as one or more conservative substitutions, non-conservative substitutions, additions, or deletions. For instance, in some embodiments, the variant may comprise the substitution W423A, W423 S, W423E, or W423H.

In some embodiments, at least one mutation that increases the nicotine-degrading activity or increases the catalytic activity of the enzyme is introduced into the variant, allowing the variant to more rapidly and/or more efficiently break-down nicotine. In some embodiments, such a mutation may improve various measures of enzymatic performance, including but not limited to, increasing $k_{cat}$, lowering $K_M$, increasing $k_{cat}/K_M$ and/or increasing $V_{max}$. Thus, in some embodiments, a variant may comprise 1, 2, 3, 4, 5, 6, 7, 8, 9, or 10 or more mutations in an active site of the wild-type NicA2 or wild-type NOX enzymes and/or in the aromatic cage, and exhibit increased nicotine-degrading activity as measured by increased $k_{cat}$, lowered $K_M$, increased $k_{cat}/K_M$, and/or increased $V_{max}$, relative to the wild-type NicA2 enzyme.

In some embodiments, the nicotine-degrading enzyme variants comprise one or more mutations in the aromatic cage of the wild-type NicA2 enzyme formed by the tryptophan at position 427 and the asparagine at position 462 of SEQ ID NO:1, such as a mutation at one or more of these positions, such as one or more conservative substitutions, non-conservative substitutions, additions, or deletions. Thus, in some embodiments, a mutation that increases the nicotine-degrading activity is at one or more of positions 427 or 462 of SEQ ID NO:1, such as a conservative substitution, non-conservative substitution, addition, or deletion at one or more of positions 427 or 462 of SEQ ID NO:1.

In some embodiments, the mutation at position 427 is the substitution W427Q, where the tryptophan (W) at position 427 of SEQ ID NO:1 (in the aromatic cage) is substituted with glutamine (Q). The variant having the amino acid sequence of SEQ ID NO:5 is an example of this type of variant. This is a non-conservative substitution in which a non-polar, aromatic amino acid is replaced with a polar, uncharged amino acid. Generally, a non-conservative substitution to an active site of an enzyme would be expected to render the enzyme dysfunctional or inoperative, yet, surprisingly, this variant exhibits significantly increased enzyme-degrading activity as compared to the wild-type NicA2 enzyme.

In some embodiments, the mutation at position 427 is the substitution W427E, where the tryptophan (W) at position 427 of SEQ ID NO:1 is substituted with glutamic acid (E). The variant having the amino acid sequence of SEQ ID NO:6 is an example of this type of variant. In some embodiments, the mutation is the substitution W427S, where the tryptophan (W) at position 427 of SEQ ID NO:1 is substituted with serine (S). The variant having the amino acid sequence of SEQ ID NO:7 is an example of this type of variant. In some embodiments, the mutation is the substitution W427M, where the tryptophan (W) at position 427 of SEQ ID NO:1 is substituted with methionine (M). The variant having the amino acid sequence of SEQ ID NO:8 is an example of this type of variant. In some embodiments, the mutation is the substitution W427R, where the tryptophan (W) at position 427 of SEQ ID NO:1 is substituted with arginine (R). The variant having the amino acid sequence of SEQ ID NO:135 is an example of this type of variant. In some embodiments, the mutation is the substitution W427H, where the tryptophan (W) at position 427 of SEQ ID NO:1 is substituted with histidine (H). The variant having the amino acid sequence of SEQ ID NO:137 is an example of this type of variant. In some embodiments, the mutation is the substitution W427M, where the tryptophan (W) at position 427 of SEQ ID NO:1 is substituted with leucine (L). The variant having the amino acid sequence of SEQ ID NO:138 is an example of this type of variant.

In some embodiments, the nicotine-degrading enzyme variants comprise one or more mutations including a mutation in the arginine (R) at position 91 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 91 is the substitution R91A, where the arginine (R) at position 91 of SEQ ID NO:1 is substituted with alanine (A). The variant having the amino acid sequence of SEQ ID NO:9 is an example of this type of variant. In some embodiments, the mutation at position 91 is the substitution R91Q, where the arginine (R) at position 91 of SEQ ID NO:1 is substituted with glutamine (Q). The variants having the amino acid sequences of SEQ ID NOs:10 and 129 are examples of this type of variant. In some embodiments, the mutation at position 91 is the substitution R91F, where the arginine (R) at position 91 of SEQ ID NO:1 is substituted with phenylalanine (F). The variant having the amino acid sequence of SEQ ID NO:11 is an example of this type of variant. In some embodiments, the mutation at position 91 is the substitution R91G, where the arginine (R) at position 91 of SEQ ID NO:1 is substituted with glycine (G). The variant having the amino acid sequence of SEQ ID NO:12 is an example of this type of variant. In some embodiments, the mutation at position 91 is the substitution R91T, where the arginine (R) at position 91 of SEQ ID NO:1 is substituted with threonine (T). The variant having the amino acid sequence of SEQ ID NO:13 is an example of this type of variant. In some embodiments, the mutation at position 91 is the substitution R91L, where the arginine (R) at position 91 of SEQ ID NO:1 is substituted with leucine (L). The variant having the amino acid sequence of SEQ ID NO:14 is an example of this type of variant. In some embodiments, the mutation at position 91 is the substitution R91S, where the arginine (R) at position 91 of SEQ ID NO:1 is substituted with serine (S). The variant having the amino acid sequence of SEQ ID NO:15 is an example of this type of variant. In some embodiments, the mutation at position 91 is the substitution R91N, where the arginine (R) at position 91 of SEQ ID NO:1 is substituted with asparagine (N). The variant having the amino acid sequence of SEQ ID NO:16 is an example of this type of variant.

In some embodiments, the nicotine-degrading enzyme variants comprise one or more mutations including a mutation in the threonine (T) at position 250 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 250 is the substitution T250G, where the threonine (T) at position 250 of SEQ ID NO:1 is substituted with glycine (G). The variant having the amino acid sequence of SEQ ID NO:17 is an example of this type of variant. In some embodiments, the mutation at position 250 is the substitution T250L, where the threonine (T) at position 250 of SEQ ID NO:1 is substituted with leucine (L). The variant having the amino acid sequence of SEQ ID NO:18 is an example of this type of variant. In some embodiments, the mutation at position 250 is the substitution T250R, where the threonine (T) at position 250 of SEQ ID NO:1 is substituted with arginine (R). The variant having the amino acid sequence of SEQ ID NO:19 is an example of this type of variant. In some embodiments, the mutation at position 250 is the substitution T250V, where the threonine (T) at position 250 of SEQ ID NO:1 is substituted with valine (V). The variant having the amino acid sequence of SEQ ID NO:20 is an example of this type of variant. In some embodiments, the mutation at position 250 is the substitution T250P, where the threonine (T) at position 250 of SEQ ID NO:1 is substituted with proline (P). The variant having the amino acid sequence of SEQ ID NO:136 is an example of this type of variant.

In some embodiments, the nicotine-degrading enzyme variants comprise one or more mutations including a mutation in the lysine (K) at position 340 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 340 is the substitution K340P, where the lysine (K) at position 340 of SEQ ID NO:1 is substituted with proline (P). The variant having the amino acid sequence of SEQ ID NO:21 is an example of this type of variant. In some embodiments, the mutation at position 340 is the substitution K340I, where the lysine (K) at position 340 of SEQ ID NO:1 is substituted with isoleucine (I). The variant having the amino acid sequence of SEQ ID NO:22 is an example of this type of variant. In some embodiments, the mutation at position 340 is the substitution K340V, where the lysine (K) at position 340 of SEQ ID NO:1 is substituted with valine (V). The variant having the amino acid sequence of SEQ ID NO:23 is an example of this type of variant. In some embodiments, the mutation at position 340 is the substitution K340D, where the lysine (K) at position 340 of SEQ ID NO:1 is substituted with aspartic acid (D). The variant having the amino acid sequence of SEQ ID NO:24 is an example of this type of variant. In some embodiments, the mutation at position 340 is the substitution K340E, where the lysine (K) at position 340 of SEQ ID NO:1 is substituted with glutamic acid (E). The variant having the amino acid sequence of SEQ ID NO:25 is an example of this type of variant.

In some embodiments, the nicotine-degrading enzyme variants comprise one or more mutations including a mutation in the glutamine (Q) at position 366 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 366 is the substitution Q366K, where the glutamine (Q) at position 366 of SEQ ID NO:1 is substituted with lysine (K). The variants having the amino acid sequences of SEQ ID NOs:26 and 130 are examples of this type of variant. In some embodiments, the mutation at position 366 is the substitution Q366E, where the glutamine (Q) at position 366 of SEQ ID NO:1 is substituted with glutamic acid (E). The variant having the amino acid sequence of SEQ ID NO:27 is an example of this type of variant. In some embodiments, the mutation at position 366 is the substitution Q366V, where the glutamine (Q) at position 366 of SEQ ID NO:1 is substituted with valine (V). The variant having the amino acid sequence of SEQ ID NO:28 is an example of this type of variant. In some embodiments, the mutation at position 366 is the substitution Q366L, where the glutamine (Q) at position 366 of SEQ ID NO:1 is substituted with leucine (L). The variant having the amino acid sequence of SEQ ID NO:29 is an example of this type of variant. In some embodiments, the mutation at position 366 is the substitution Q366I, where the glutamine (Q) at position 366 of SEQ ID NO:1 is substituted with isoleucine (I). The variant having the amino acid sequence of SEQ ID NO:30 is an example of this type of variant. In some embodiments, the mutation at position 366 is the substitution Q366Y, where the glutamine (Q) at position 366 of SEQ ID NO:1 is substituted with tyrosine (Y). The variant having the amino acid sequence of SEQ ID NO:31 is an example of this type of variant.

In some embodiments, the nicotine-degrading enzyme variants comprise one or more mutations including a mutation in the threonine (T) at position 381 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 381 is the substitution T381P, where the threonine (T) at position 381 of SEQ ID NO:1 is substituted with proline (P). The variant having the amino acid sequence of SEQ ID NO:32 is an example of this type of variant. In some embodiments, the mutation at position 381 is the substitution T381I, where the threonine (T) at position 381 of SEQ ID NO:1 is substituted with isoleucine (I). The variant having the amino acid sequence of SEQ ID NO:33 is an example of this type of variant. In some embodiments, the mutation at position 381 is the substitution T381V, where the threonine (T) at position 381 of SEQ ID NO:1 is substituted with valine (V). The variants having the amino acid sequences of SEQ ID NOs: 34 and 131 are examples of this type of variant. In some embodiments, the mutation at position 381 is the substitution T381Q, where the threonine (T) at position 381 of SEQ ID NO:1 is substituted with glutamine (Q). The variant having the amino acid sequence of SEQ ID NO:35 is an example of this type of variant. In some embodiments, the mutation at position 381 is the substitution T381N, where the threonine (T) at position 381 of SEQ ID NO:1 is substituted with asparagine (N). The variant having the amino acid sequence of SEQ ID NO:36 is an example of this type of variant. In some embodiments, the mutation at position 381 is the substitution T381L, where the threonine (T) at position 381 of SEQ ID NO:1 is substituted with leucine (L). The variant having the amino acid sequence of SEQ ID NO:37 is an example of this type of variant. In some embodiments, the mutation at position 381 is the substitution T381M, where the threonine (T) at position 381 of SEQ ID NO:1 is substituted with methionine (M). The variant having the amino acid sequence of SEQ ID NO:38 is an example of this type of variant.

In some embodiments, the nicotine-degrading enzyme variants comprise one or more mutations including a mutation in the asparagine (N) at position 462 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 462 is the substitution N462L, where the asparagine (N) at position 462 of SEQ ID NO:1 is substituted with leucine (L). The variants having the amino acid sequences of SEQ ID NOs: 39 and 132 are examples of this type of variant. In some embodiments, the mutation at position 462 is the substitution N462Y, where the asparagine (N) at position 462 of SEQ ID NO:1 is substituted with tyrosine (Y). The variants having the amino acid sequences of SEQ ID NOs:40 and 133 are examples of this type of variant. In some embodiments, the mutation at position 462 is the substitution N462S, where the asparagine (N) at position 462 of SEQ ID NO:1 is substituted with serine (S). The variant having the amino acid sequence of SEQ ID NO:41 is an example of this type of variant. In some embodiments, the mutation at position 462 is the substitution N462F, where the asparagine (N) at position 462 of SEQ ID NO:1 is substituted with phenylalanine (F). The variants having the amino acid sequences of SEQ ID NOs:42 and 137 are examples of this type of variant. In some embodiments, the mutation at position 462 is the substitution N462G, where the asparagine (N) at position 462 of SEQ ID NO:1 is substituted with glycine (G). The variant having the amino acid sequence of SEQ ID NO:43 is an example of this type of variant. In some embodiments, the mutation at position 462 is the substitution N462E, where the asparagine (N) at position 462 of SEQ ID NO:1 is substituted with glutamic acid (E). The variant having the amino acid sequence of SEQ ID NO:44 is an example of this type of variant. In some embodiments, the mutation at position 462 is the substitution N462A, where the asparagine (N) at position 462 of SEQ ID NO:1 is substituted with alanine (A). The variant having the amino acid sequence of SEQ ID NO:45 is an example of this type of variant. In some embodiments, the mutation at position 462 is the substitution N462M, where the asparagine (N) at position 462 of SEQ ID NO:1 is substituted with methionine (M). The variant having the amino acid sequence of SEQ ID NO:138 is an example of this type of variant.

In some embodiments, the nicotine-degrading enzyme variants comprise one or more mutations including a mutation in the isoleucine (I) at position 463 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 463 is the substitution I463F, where the isoleucine (I) at position 463 of SEQ ID NO:1 is substituted with phenylalanine (F). The variant having the amino acid sequence of SEQ ID NO:46 is an example of this type of variant. In some embodiments, the mutation at position 463 is the substitution I463Y, where the isoleucine (I) at position 463 of SEQ ID NO:1 is substituted with tyrosine (Y). The variant having the amino acid sequence of SEQ ID NO:47 is an example of this type of variant. In some embodiments, the mutation at position 463 is the substitution I463A, where the isoleucine (I) at position 463 of SEQ ID NO:1 is substituted with alanine (A). The variant having the amino acid sequence of SEQ ID NO:48 is an example of this type of variant. In some embodiments, the mutation at position 463 is the substitution I463V, where the isoleucine (I) at position 463 of SEQ ID NO:1 is substituted with valine (V). The variant having the amino acid sequence of SEQ ID NO:49 is an example of this type of variant. In some embodiments, the mutation at position 463 is the substitution I463L, where the isoleucine (I) at position 463 of SEQ ID NO:1 is substituted with leucine (L). The variant having the amino acid sequence of SEQ ID NO:50 is an example of this type of variant.

In some embodiments, the nicotine-degrading enzyme variants comprise one or more mutations including a mutation in the leucine (L) at position 217 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 217, 250, 340, 366, 381, 427, 462, or 463 of SEQ ID NO:1.

In some embodiments, the mutation at position 217 is the substitution L217Q, where the leucine (L) at position 217 of SEQ ID NO:1 is substituted with glutamine (Q). The variant having the amino acid sequence of SEQ ID NO:51 is an example of this type of variant. In some embodiments, the mutation at position 217 is the substitution L217G, where the leucine (L) at position 217 of SEQ ID NO:1 is substituted with glycine (G). The variant having the amino acid sequence of SEQ ID NO:52 is an example of this type of variant. In some embodiments, the mutation at position 217 is the substitution L217E, where the leucine (L) at position 217 of SEQ ID NO:1 is substituted with glutamic acid (E). The variant having the amino acid sequence of SEQ ID NO:53 is an example of this type of variant. In some embodiments, the mutation at position 217 is the substitution L217I, where the leucine (L) at position 217 of SEQ ID NO:1 is substituted with isoleucine (I). The variant having the amino acid sequence of SEQ ID NO:54 is an example of this type of variant. In some embodiments, the mutation at position 217 is the substitution L217C, where the leucine (L) at position 217 of SEQ ID NO:1 is substituted with cysteine (C). The variant having the amino acid sequence of SEQ ID NO:55 is an example of this type of variant. In some embodiments, the mutation at position 217 is the substitution L217S, where the leucine (L) at position 217 of SEQ ID NO:1 is substituted with serine (S). The variant having the amino acid sequence of SEQ ID NO:56 is an example of this type of variant.

In some embodiments, the nicotine-degrading enzyme variants comprise one or more mutations including a mutation in the alanine (A) at position 107 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 107 is the substitution A107R, where the alanine (A) at position 107 of SEQ ID NO:1 is substituted with arginine (R). The variants having the amino acid sequences of SEQ ID NOs:124 or 134 are examples of this type of variant. In some embodiments, the mutation at position 107 is the substitution A107K, where the alanine (A) at position 107 of SEQ ID NO:1 is substituted with lysine (K). The variant having the amino acid sequence of SEQ ID NO:125 is an example of this type of variant. In some embodiments, the mutation at position 107 is the substitution A107T, where the alanine (A) at position 107 of SEQ ID NO:1 is substituted with tyrosine (T). The variant having the amino acid sequence of SEQ ID NO:126 is an example of this type of variant. In some embodiments, the mutation at position 107 is the substitution A107H, where the alanine (A) at position 107 of SEQ ID NO:1 is substituted with histidine (H). The variant having the amino acid sequence of SEQ ID NO:142 is an example of this type of variant. In some embodiments, the mutation at position 107 is the substitution A107P, where the alanine (A) at position 107 of SEQ ID NO:1 is substituted with proline (P). The variant having the amino acid sequence of SEQ ID NO:143 is an example of this type of variant.

In some embodiments, the nicotine-degrading enzyme variants comprise one or more mutations including a mutation in the phenylalanine (F) at position 355 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 355 is the substitution F355C, where the phenylalanine (F) at position 355 of SEQ ID NO:1 is substituted with cysteine (C). The variant having the amino acid sequence of SEQ ID NO:127 is an example of this type of variant. In some embodiments, the mutation at position 355 is the substitution F355V, where the phenylalanine (F) at position 355 of SEQ ID NO:1 is substituted with valine (V). The variant having the amino acid sequence of SEQ ID NO:128 is an example of this type of variant.

In some embodiments, the nicotine-degrading enzyme variants comprise one or more mutations including a mutation in the phenylalanine (F) at position 104 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 104 is the substitution F104L, where the phenylalanine (F) at position 104 of SEQ ID NO:1 is substituted with leucine (L). The variant having the amino acid sequence of SEQ ID NO:140 is an example of this type of variant.

In some embodiments, the nicotine-degrading enzyme variants comprise one or more mutations including a mutation in the glycine (G) at position 106 of SEQ ID NO:1, such as one or more conservative substitutions, non-conservative substitutions, additions, or deletions. Thus, in some embodiments, a mutation that increases the nicotine-degrading activity is at one or more of positions 91, 104, 106, 107, 217, 250, 340, 355, 366, 381, 427, 462, or 463 of SEQ ID NO:1, such as a conservative substitution, non-conservative substitution, addition, or deletion at one or more of positions 91, 104, 106, 107, 217, 250, 340, 355, 366, 381, 427, 462, or 463 of SEQ ID NO:1.

In some embodiments, the mutation at position 106 is the substitution G106S where the glycine (G) at position 106 of SEQ ID NO:1 is substituted with serine (S). The variant having the amino acid sequence of SEQ ID NO:141 is an example of this type of variant.

In some embodiments, the nicotine-degrading enzyme variants comprise one, two, or three or more mutations to SEQ ID NO:1. For instance, in some embodiment, the nicotine-degrading enzyme may comprise a mutation in the tryptophan (W) at position 427 of SEQ ID NO:1, a mutation in the isoleucine (I) at position 262, and a mutation in the asparagine (N) at position 263, such as one or more conservative substitutions, non-conservative substitutions, additions, or deletions. Thus, in some embodiments, at least one mutation that increases the nicotine-degrading activity is at one, two, or three or more of positions 107, 355, 262, 263, 217, 91, 463, 381, 366, 340, 250, 427, or 462 of SEQ ID NO:1, such as a conservative substitution, non-conservative substitution, addition, or deletion at one or more of positions 107, 355, 262, 263, 217, 91, 463, 381, 366, 340, 250, 427, or 462 of SEQ ID NO:1.

In some embodiments, the mutation is a bi-substitution of W427Q and I262A, such as where the tryptophan (W) at position 427 of SEQ ID NO:1 is substituted with glutamine (Q) and the isoleucine (I) at position 262 of SEQ ID NO:1 is substituted with alanine (A). The variant having the amino acid sequence of SEQ ID NO:62 is an example of this type of variant. In some embodiments, the mutation is a bi-substitution of W427H and N462F, such as where the tryptophan (W) at position 427 of SEQ ID NO:1 is substituted with histidine (H) and the asparagine (N) at position 462 of SEQ ID NO:1 is substituted with phenylalanine (F). The variant having the amino acid sequence of SEQ ID NO:137 is an example of this type of variant. In some embodiments, the mutation is a bi-substitution of W427L and N462M, such as where the tryptophan (W) at position 427 of SEQ ID NO:1 is substituted with leucine (L) and the asparagine (N) at position 462 of SEQ ID NO:1 is substituted with methionine (M). The variant having the amino acid sequence of SEQ ID NO:138 is an example of this type of variant. In some embodiments, the mutation is a tri-substitution of W427Q, I262T, and N263R, such as where the tryptophan (W) at position 427 of SEQ ID NO:1 is substituted with glutamine (Q), the isoleucine (I) at position 262 of SEQ ID NO:1 is substituted with threonine (T), and the asparagine (N) at position 263 of SEQ ID NO:1 is substituted with arginine (R). The variant having the amino acid sequence of SEQ ID NO:63 is an example of this type of variant.

In some embodiments, the nicotine-degrading enzyme variants comprise one or more mutations including a mutation in the tryptophan (W) at position 423 of SEQ ID NO:57, such as one or more conservative substitutions, non-conservative substitutions, additions, or deletions. Thus, in some embodiments, a mutation that increases the nicotine-degrading activity is at one or more positions including 423 of SEQ ID NO:57, such as a conservative substitution, non-conservative substitution, addition, or deletion at one or more positions 423 of SEQ ID NO:57.

In some embodiments, the mutation at position 423 is the substitution W423A, where the tryptophan (W) at position 423 of SEQ ID NO:57 is substituted with alanine (A). The variant having the amino acid sequence of SEQ ID NO:58 is an example of this type of variant. In some embodiments, the mutation at position 423 is the substitution W423S, where the tryptophan (W) at position 423 of SEQ ID NO:57 is substituted with serine (S). The variant having the amino acid sequence of SEQ ID NO:59 is an example of this type of variant. In some embodiments, the mutation at position 423 is the substitution W423E, where the tryptophan (W) at position 423 of SEQ ID NO:57 is substituted with glutamic acid (E). The variant having the amino acid sequence of SEQ ID NO:60 is an example of this type of variant. In some embodiments, the mutation at position 423 is the substitution W423H, where the tryptophan (W) at position 423 of SEQ ID NO:57 is substituted with histidine (H). The variant having the amino acid sequence of SEQ ID NO:61 is an example of this type of variant.

Additionally or alternatively, in some embodiments, the nicotine-degrading enzyme variants comprise one or more mutations within an immunogenic T-cell epitope, such as one or more mutations within an immunogenic T-cell epitope within a region selected from positions 10-32, 68-94, 189-225, 248-285, 296-327, 336-391, or 435-459 of SEQ ID NO:1, such as one or more mutations within an immunogenic T-cell epitope selected from positions 16-24, 73-81, 258-266, 302-310, 373-381, or 447-455 of SEQ ID NO:1, such as one or more conservative substitutions, non-conservative substitutions, additions, or deletions in one or more of these regions. Thus, in some embodiments, a variant may comprise 1, 2, 3, 4, 5, 6, 7, 8, 9, or 10 or more mutations in 1, 2, 3, 4, 5, 6, or 7, immunogenic T-cells epitopes. In some embodiments, such variants exhibit reduced immunogenicity when administered to a mammalian subject.

In some embodiments, the nicotine-degrading enzymes variants comprise a mutation in an immunogenic T-cell epitope at one or more positions selected from 74, 77, 78, 80, 262-266, 303, 304, 306, 310, 374, 377, 378, 382, 383, 450-452, or 457 of SEQ ID NO:1, including all permutations and combinations thereof. For example, a variant may include any one or more of the mutations set forth below, including one or more of the exemplary mutations in Epitope B, one or more of the exemplary mutations in Epitope 1, one or more of the exemplary mutations in Epitope 2, one or more of the exemplary mutations in Epitope 3, and/or one or more of the exemplary mutations in Epitope 4. For instance, in some embodiments, the nicotine-degrading enzyme may have an amino acid substitution at position 262 and/or 263 of SEQ ID NO:1, such as an I262A substitution or I262T/N263R substitutions.

TABLE 3

Exemplary Mutations in the NicA2 Epitopes (numbering based on SEQ ID NO: 1)

| Epitope B | Epitope 1 | Epitope 2 | Epitope 3 | Epitope 4 |
|---|---|---|---|---|
| L74N, Y77R | I262A, A264Q | V303T, V304N, M306I | L374Q, I377S | I448Q, F450S |
| L74N, Y77K | I262K, L266D | V304A, M306Q | L374A, I377A | I448E, F450N |
| L74Q, Y77R | I262T | V304A, M306N | L374Q, I377A | I448A, F450N |
| L74Q, Y77N | I262S | V304A | L374N, I377A | I448Q, F450Q |
| L74N, Y77Q | I262D, L266K | V304A, M306H | L374N, I382Q | I448T, F450Q |

TABLE 3-continued

Exemplary Mutations in the NicA2 Epitopes
(numbering based on SEQ ID NO: 1)

| Epitope B | Epitope 1 | Epitope 2 | Epitope 3 | Epit

97%, about 98%, or about 99% sequence identity with the variant sequence of SEQ ID NO:14.

In some embodiments, a nicotine-degrading enzyme variant as described herein is or comprises SEQ ID NO:15. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:15.

In some embodiments, a nicotine-degrading enzyme variant as described herein is or comprises SEQ ID NO:16. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:16.

In some embodiments, a nicotine-degrading enzyme variant as described herein is or comprises SEQ ID NO:17. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:17.

In some embodiments, a nicotine-degrading enzyme variant as described herein is or comprises SEQ ID NO:18. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:18.

In some embodiments, a nicotine-degrading enzyme variant as described herein is or comprises SEQ ID NO:19. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:19.

In some embodiments, a nicotine-degrading enzyme variant as described herein is or comprises SEQ ID NO:20. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:20.

In some embodiments, a nicotine-degrading enzyme variant as described herein is or comprises SEQ ID NO:21. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:21.

In some embodiments, a nicotine-degrading enzyme variant as described herein is or comprises SEQ ID NO:22. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:22.

In some embodiments, a nicotine-degrading enzyme variant as described herein is or comprises SEQ ID NO:23. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:23.

In some embodiments, a nicotine-degrading enzyme variant as described herein is or comprises SEQ ID NO:24. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:24.

In some embodiments, a nicotine-degrading enzyme variant as described herein is or comprises SEQ ID NO:25. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:25.

In some embodiments, a nicotine-degrading enzyme variant as described herein is or comprises SEQ ID NO:26. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:26.

In some embodiments, a nicotine-degrading enzyme variant as described herein is or comprises SEQ ID NO:27. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:27.

In some embodiments, a nicotine-degrading enzyme variant as described herein is or comprises SEQ ID NO:28. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:28.

In some embodiments, a nicotine-degrading enzyme variant as described herein is or comprises SEQ ID NO:29. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:29.

In some embodiments, a nicotine-degrading enzyme variant as described herein is or comprises SEQ ID NO:30. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:30.

In some embodiments, a nicotine-degrading enzyme variant as described herein is or comprises SEQ ID NO:31. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:31.

In some embodiments, a nicotine-degrading enzyme variant as described herein is or comprises SEQ ID NO:32. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:32.

In some embodiments, a nicotine-degrading enzyme variant as described herein is or comprises SEQ ID NO:33. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:33.

In some embodiments, a nicotine-degrading enzyme variant as described herein is or comprises SEQ ID NO:34. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:34.

In some embodiments, a nicotine-degrading enzyme variant as described herein is or comprises SEQ ID NO:35. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:35.

In some embodiments, a nicotine-degrading enzyme variant as described herein is or comprises SEQ ID NO:36. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:36.

In some embodiments, a nicotine-degrading enzyme variant as described herein is or comprises SEQ ID NO:37. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:37.

In some embodiments, a nicotine-degrading enzyme variant as described herein is or comprises SEQ ID NO:38. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:38.

In some embodiments, a nicotine-degrading enzyme variant as described herein is or comprises SEQ ID NO:39. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:39.

In some embodiments, a nicotine-degrading enzyme variant as described herein is or comprises SEQ ID NO:40. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:40.

In some embodiments, a nicotine-degrading enzyme variant as described herein is or comprises SEQ ID NO:41. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:41.

In some embodiments, a nicotine-degrading enzyme variant as described herein is or comprises SEQ ID NO:42. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:42.

In some embodiments, a nicotine-degrading enzyme variant as described herein is or comprises SEQ ID NO:43. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:43.

In some embodiments, a nicotine-degrading enzyme variant as described herein is or comprises SEQ ID NO:44. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:44.

In some embodiments, a nicotine-degrading enzyme variant as described herein is or comprises SEQ ID NO:45. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:45.

In some embodiments, a nicotine-degrading enzyme variant as described herein is or comprises SEQ ID NO:46. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:46.

In some embodiments, a nicotine-degrading enzyme variant as described herein is or comprises SEQ ID NO:47. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:47.

In some embodiments, a nicotine-degrading enzyme variant as described herein is or comprises SEQ ID NO:48. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:48.

In some embodiments, a nicotine-degrading enzyme variant as described herein is or comprises SEQ ID NO:49. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:49.

In some embodiments, a nicotine-degrading enzyme variant as described herein is or comprises SEQ ID NO:50. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:50.

In some embodiments, a nicotine-degrading enzyme variant as described herein is or comprises SEQ ID NO:51. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:51.

In some embodiments, a nicotine-degrading enzyme variant as described herein is or comprises SEQ ID NO:52. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:52.

In some embodiments, a nicotine-degrading enzyme variant as described herein is or comprises SEQ ID NO:53. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:53.

In some embodiments, a nicotine-degrading enzyme variant as described herein is or comprises SEQ ID NO:54. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:54.

In some embodiments, a nicotine-degrading enzyme variant as described herein is or comprises SEQ ID NO:55. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:55.

In some embodiments, a nicotine-degrading enzyme variant as described herein is or comprises SEQ ID NO:56. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:56.

In some embodiments, a nicotine-degrading enzyme variant as described herein is or comprises SEQ ID NO:57. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:57.

In some embodiments, a nicotine-degrading enzyme variant as described herein is or comprises SEQ ID NO:58. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:58.

In some embodiments, a nicotine-degrading enzyme variant as described herein is or comprises SEQ ID NO:59. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:59.

In some embodiments, a nicotine-degrading enzyme variant as described herein is or comprises SEQ ID NO:60. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:60.

In some embodiments, a nicotine-degrading enzyme variant as described herein is or comprises SEQ ID NO:61. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:61.

In some embodiments, a nicotine-degrading enzyme variant as described herein is or comprises SEQ ID NO:62. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:62.

In some embodiments, a nicotine-degrading enzyme variant as described herein is or comprises SEQ ID NO:63. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:63.

In some embodiments, a nicotine-degrading enzyme variant as described herein is or comprises SEQ ID NO:124. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:124.

In some embodiments, a nicotine-degrading enzyme variant as described herein is or comprises SEQ ID NO:125. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:125.

In some embodiments, a nicotine-degrading enzyme variant as described herein is or comprises SEQ ID NO:126. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:126.

In some embodiments, a nicotine-degrading enzyme variant as described herein is or comprises SEQ ID NO:127. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:127.

In some embodiments, a nicotine-degrading enzyme variant as described herein is or comprises SEQ ID NO:128. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:128.

In some embodiments, a nicotine-degrading enzyme variant as described herein is or comprises SEQ ID NO:129. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:129.

In some embodiments, a nicotine-degrading enzyme variant as described herein is or comprises SEQ ID NO:130. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:130.

In some embodiments, a nicotine-degrading enzyme variant as described herein is or comprises SEQ ID NO:131. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:131.

In some embodiments, a nicotine-degrading enzyme variant as described herein is or comprises SEQ ID NO:132. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:132.

In some embodiments, a nicotine-degrading enzyme variant as described herein is or comprises SEQ ID NO:133. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:133.

In some embodiments, a nicotine-degrading enzyme variant as described herein is or comprises SEQ ID NO:134. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:134.

In some embodiments, a nicotine-degrading enzyme variant as described herein is or comprises SEQ ID NO:135. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:135.

In some embodiments, a nicotine-degrading enzyme variant as described herein is or comprises SEQ ID NO:136. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:136.

In some embodiments, a nicotine-degrading enzyme variant as described herein is or comprises SEQ ID NO:137. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:137.

In some embodiments, a nicotine-degrading enzyme variant as described herein is or comprises SEQ ID NO:138. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:138.

In some embodiments, a nicotine-degrading enzyme variant as described herein is or comprises SEQ ID NO:140. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:140.

In some embodiments, a nicotine-degrading enzyme variant as described herein is or comprises SEQ ID NO:141. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:141.

In some embodiments, a nicotine-degrading enzyme variant as described herein is or comprises SEQ ID NO:142. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:142.

In some embodiments, a nicotine-degrading enzyme variant as described herein is or comprises SEQ ID NO:143. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:143.

In some embodiments, a variant as described herein exhibits increased nicotine-degrading activity relative to the wild-type NicA2 or NOX enzymes, such that its activity is at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2250%, about 2500%, about 2750%, about 3000%, about 3250%, about 3500%, about 3750%, about 4000%, about 4250%, about 4500%, about 4750%, or about 5000% or more than that of the wild-type NicA2 or NOX enzymes, as determined by an assay such as an AMPLEX® Red assay (Thermo Fisher Scientific).

In some embodiments, a variant as described herein exhibits increased nicotine-degrading activity relative to the wild-type NicA2 or NOX enzymes, such that its activity is at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2250%, about 2500%, about 2750%, about 3000%, about 3250%, about 3500%, about 3750%, about 4000%, about 4250%, about 4500%, about 4750%, or about 5000% or more than that of the wild-type NicA2 or NOX enzymes as determined by an assay where residual nicotine concentrations are measured using Gas Chromatography (GC; Hieda et al.: Immunization of rats reduces nicotine distribution to brain. Psychopharmacology, 143, 150-157, 1999) after incubation with a fixed concentration of enzyme in either buffer or rat serum at 37° C. and quenching activity at fixed time points by mixing with MeOH.

In some embodiments, a variant as described herein exhibits decreased immunogenicity in a mammalian subject relative to wild-type NicA2 or NOX, such that it is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% less immunogenic than the wild-type NicA2 or NOX enzymes. Unless otherwise specified, "decreased immunogenicity" as compared to the wild-type NicA2 or NOX enzymes as used herein refers decreased immunogenicity as shown by one or more of in silico approaches, in vitro assays, in vivo studies (e.g., using transgenic animals), ex vivo studies using human T-cells, or clinical studies with human subjects.

IV. Pharmaceutical Compositions

The nicotine-degrading enzyme variants disclosed herein can be formulated into pharmaceutical compositions suitable for administration to the target subject (i.e., a human or other mammal) via a predetermined route of administration, as discussed in more detail below.

Pharmaceutical compositions may include one or more variants as described herein and a pharmaceutically acceptable carrier or diluent.

The compositions may be formulated for intravenous, subcutaneous, intraperitoneal, intramuscular, oral, nasal, pulmonary, ocular, vaginal, or rectal administration. In some embodiments, the compositions are formulated for intravenous, subcutaneous, intraperitoneal, or intramuscular administration, such as in a solution, suspension, emulsion, liposome formulation, etc. The pharmaceutical compositions can be formulated to be an immediate-release composition, sustained-release composition, delayed-release composition, etc., using techniques known in the art Pharmaceutically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, colorants, sweetening/flavoring agents, adsorbing agents, wetting agents and the like.

In some embodiments, the composition is formulated for administration by injection or infusion. In some embodiments, the composition is formulated for oral administration.

In some embodiments, the nicotine-degrading enzyme variant is a long-acting variant that has been modified in order to extend its half-life in vivo (after administration). Various techniques are known in the art for extending the circulating half-life of peptides. For example, in some embodiments the variant is conjugated to polyethylene glycol (PEG) or a similar polymer that prolongs half-life. As discussed in more detail in Example 3 below, conjugating PEG to the disclosed nicotine-degrading enzyme variants can improve the pharmacokinetic properties of the variant. In some embodiments PEGylation has one or more effects selected from masking one or more immunogenic epitopes of the variant, decreasing variant-specific antibody titers, and attenuating T-cell proliferation and/or cytokine responses. Additionally or alternatively, in some embodiments, conjugating the variants to PEG does not decrease the enzymatic activity of the nicotine-degrading enzyme variants, or does not significantly decrease the enzymatic activity, or does not eliminate the enzymatic activity.

The PEG chain length and architecture (i.e. linear vs. branched) may be selected and varied to impact, impart, or promote different properties, as illustrated in the examples below. PEG can be conjugated to the variants by methods known for conjugating PEG to proteins, including those illustrated in the examples below. Any of the variants described herein can be PEGylated, including variants defined by or comprising any of SEQ ID NOs: 2-56, 58-63, or 124-134. For the purposes of conjugating PEG to the disclosed enzyme variants, the size or length of the PEG polymers can vary. For example, linear PEG conjugated to the disclosed enzyme variants may be in the range of 1-50 kDa, 5-40 kDa, or 10-20 kDa, such as 1, 2, 3, 4, 5, 6, 7, 8, 9, 10, 11, 12, 13, 14, 15, 16, 17, 18, 19, 20, 25, 30, 35, 40, 45, or 50 kDa. Additionally, the PEG polymers may be branched, with size in the range of 20-80 kDa, such as 20, 40, 60 or 80 kDa.

In some embodiments, the variant is fused to an albumin-binding peptide, an albumin-binding protein domain, human serum albumin, or an inert polypeptide. Exemplary inert polypeptides that have been used to increase the circulating half-life of peptides include, but are not limited to, XTEN® (also known as recombinant PEG or "rPEG"), a homo-amino acid polymer (HAP; HAPylation), a proline-alanine serine polymer (PAS; PASylation), or an elastin-like peptide (ELP; ELPylation). As used herein, "fused to" includes genetic fusion, directly or through a linker, resulting in a single polypeptide containing multiple domains, unless otherwise specified.

V. Methods of Treating Nicotine Addiction or Facilitating Smoking Cessation

As noted above, the variants described herein are useful in methods of treating nicotine addiction and/or facilitating smoking cessation (or the cessation of use of other tobacco products) or preventing relapse of smoking (or consumption of other tobacco products) in a mammalian subject in need thereof. (For convenience, in the discussion that follows, these methods are referred to collectively as treating nicotine addiction or facilitating smoking cessation.) In some embodiments, the subject is a human subject addicted to nicotine or desiring to quit smoking or maintain abstinence from smoking or consumption of other nicotine products, or prevent relapse of smoking or consumption of other nicotine products.

The methods generally involve administering a therapeutically effective amount of a nicotine-degrading enzyme variant as described herein (or a pharmaceutical composition comprising the same) to the subject. However, in some embodiments, the methods comprise administering a nucleic acid encoding the nicotine-degrading enzyme variant in a construct that expresses the variant in vivo. For example, in such embodiments, the nucleic acid can be provided in a suitable vector, such as an adeno-associated virus (AAV) gene transfer vector. Other exemplary vectors that are suitable for use in such methods are known in the art. See, e.g., Lukashev and Zamyatnin, *Biochem.*, 81(7): 700-8 (2016)). Exemplary vectors may include one or more enhancers (e.g., a cytomegalovirus (CMV) enhancer), promoters (e.g., chicken β-actin promoter), and/or other elements enhancing the properties of the expression cassette. Methods of making suitable vectors and general methods of using expression vectors in vivo are known in the art. See, e.g., (see Hicks et al., *Sci. Transl. Med.*, 4(140): 140ra87 (2012)).

In some embodiments, a subject in need of treatment for nicotine addiction or facilitation of smoking cessation is a human subject who consumes nicotine products, such as smoking tobacco, chewing tobacco, electronic cigarettes, and/or other nicotine delivery devices. Such a subject may or may not be physically addicted to nicotine and/or psychologically addicted to consuming nicotine products. Typical subjects in need of smoking cessation treatment smoke or use tobacco or other nicotine products daily, such as smoking at least 1 cigarette a day, or more, such as at least about 5, at least about 10, at least about 15, at least about 20, or more, cigarettes per day, including fewer than 10, 10-20, 20-30, 30-40, or 40 or more (or the equivalent use of other tobacco or nicotine products).

In some embodiments, a therapeutically effective amount of a nicotine-degrading enzyme variant is an amount effective to reduce plasma levels of nicotine, to reduce levels of nicotine localized in the brain, or both.

Nicotine exerts many of its significant effects after it crosses the blood brain barrier. In some embodiments, the methods and uses described herein reduce or prevent nicotine from crossing the blood-brain-barrier. Thus, in some embodiments, administration of a nicotine-degrading enzyme variant as described herein degrades nicotine circulating in the bloodstream of the subject, thereby reducing or preventing the nicotine from crossing the blood-brain-barrier. Thus, in some embodiments, the methods described herein reduce or prevent the physiological and psychological effects of nicotine that originate in the brain. Because the subject will experience a lessening or cessation of these effects, he/she will lose the desire to consume nicotine products. Additionally or alternatively, the disclosed nicotine-degrading enzyme variants may exert an effect by affecting the ability of nicotine to stimulate the peripheral nervous system.

The specific amount of a nicotine-degrading enzyme that is administered may depend on one or more of the age and/or weight of the subject, the amount of nicotine routinely consumed (e.g., smoked, chewed. or inhaled), and/or the level of nicotine in the subject's brain or plasma at the time of treatment. In some embodiments, a variant is administered at a dose of from about 0.01 to about 20 mg/kg, about 0.1 mg/kg to about 18 mg/kg, about 1 mg/kg to about 16 mg/kg, about 2 mg/kg to about 14 mg/kg, or about 5 mg/kg to about 10 mg/kg. In some embodiments, a variant is administered at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8/5 mg/kg, about 9 mg/kg, about 9.5 mg/kg, about 10 mg/kg, about 10.5 mg/kg, about 12 mg/kg, about 12.5 mg/kg, about 13 mg/kg, about 13.5 mg/kg, about 14 mg/kg, about 14.5 mg/kg, about 15 mg/kg, about 15.5 mg/kg, about 16 mg/kg, about 16.5 mg/kg, about 17 mg/kg, about 17.5 mg/kg, about 18 mg/kg, about 18.5 mg/kg, about 19 mg/kg, about 19.5 mg/kg, or about 20 mg/kg. In some embodiments, a variant is administered at a dose of about 0.5 mg, about 1 mg, about 2.5 mg, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg. When more than one variant is administered, the total amount of variants administered may be in accordance with the foregoing guidance.

In some embodiments, the methods comprise administering a single dose of a nicotine-degrading enzyme variant(s) (or composition comprising the same). In some embodiments, the method comprises administering repeated doses, such as for a predetermined period of time of until the symptoms or effects of nicotine addiction are reduced, ameliorated, or eliminated or until the subject has ceased smoking or otherwise consuming nicotine. In some embodiments, treatment is repeated with additional doses of the variant(s) if signs/symptoms/effects persist or if the subject continues to have nicotine cravings or experiences them anew.

In some embodiments, the methods comprise administering a nicotine-degrading enzyme variant(s) (or composition comprising the same) three or more times a day, twice a day, or once a day. In some embodiments, the methods comprise administering a nicotine-degrading enzyme variant(s) (or composition comprising the same) once every other day, three times a week, twice a week, once a week, once every other week, once every three weeks, once a month, or less frequently. In such embodiments, the nicotine-degrading enzyme variant may be a long-acting nicotine-degrading enzyme variant as described above.

In some embodiments, treatment may continue for 1, 2, 3, 4, 5, 6, 7, 8, 9, 10, 11, 12, 13, 14, 15, 16, 17, 18, 19, 20, or 21 or more days; 1, 2, 3, 4, 5, 6, 7, 8, 9, 10, 11, 12, 13, 14, 15, 16, 17, or 18 or weeks months; or 1, 2, 3, 4, 5, 6, 7, 8, 9, 10, 11, or 12 or more months; or 1, 2, or 3 or more years or until the subject no long experiences nicotine cravings or other nicotine withdrawal symptoms, or has ceased smoking or using other tobacco products.

VI. Methods of Treating Nicotine Poisoning

The disclosed nicotine-degrading enzyme variants may be used to treat nicotine poisoning, nicotine overdose, or nicotine toxicity. For convenience, these methods are referred to herein collecting as treating nicotine poisoning. In some aspects, the methods of treating nicotine poisoning described herein comprise administering to a mammalian subject in need thereof a nicotine-degrading enzyme variant as disclosed herein, or a pharmaceutical composition comprising the same. In some embodiments, the methods comprise administering a nicotine-degrading enzyme variant to a subject that has ingested or consumed a toxic amount of nicotine. In some embodiments, the methods may comprise administering both a nicotine-degrading enzyme variant and another compound that is useful for treating nicotine poisoning, such as activated charcoal or another agent. In such embodiments, the enzyme variant and the second compound (e.g., activated charcoal) can be administered sequentially or simultaneously, from the same or different compositions. Thus, the treatment may include administering activated charcoal and/or other supportive treatments to address the symptoms and/or effects of nicotine poisoning.

In some embodiments, the therapeutically effective amount of the nicotine-degrading enzyme variant is effective to reduce, ameliorate, or eliminate one or more symptoms or effects of nicotine poisoning or overdose. The specific amount administered may depend on one or more of the age and/or weight of the subject, the amount of nicotine believed to have been ingested, and/or the subject's plasma level of nicotine at the time of treatment, and/or the subject's brain level of nicotine at the time of treatment. In some embodiments, the subject that is being treated for nicotine poisoning is an adult, while in some embodiments, the subject is a child (i.e., less than 19 years of age). In some embodiments, a therapeutically effective amount of a nicotine-degrading enzyme variant is an amount effective to reduce plasma levels of nicotine, and/or to reduce the amount of nicotine localized in specific tissues of the subject (e.g., brain/central nervous system, heart and vasculature, etc.). In specific embodiments, a therapeutically effective amount of a nicotine-degrading enzyme variant is an amount effective to reduce plasma levels of nicotine, to reduce levels of nicotine localized in the brain, or both.

The specific amount of a nicotine-degrading enzyme that is administered may depend on one or more of the age and/or weight of the subject, the amount of nicotine that was acutely consumed, and/or the level of nicotine in the subject's brain or plasma at the time of treatment. In some embodiments, a variant is administered at a dose of from about 0.01 to about 20 mg/kg, about 0.1 mg/kg to about 18 mg/kg, about 1 mg/kg to about 16 mg/kg, about 2 mg/kg to about 14 mg/kg, or about 5 mg/kg to about 10 mg/kg. In some embodiments, a variant is administered at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8/5 mg/kg, about 9 mg/kg, about 9.5 mg/kg, about 10 mg/kg, about 10.5 mg/kg, about 12 mg/kg, about 12.5 mg/kg, about 13 mg/kg, about 13.5 mg/kg, about 14 mg/kg, about 14.5 mg/kg, about 15 mg/kg, about 15.5 mg/kg, about 16 mg/kg, about 16.5 mg/kg, about 17 mg/kg, about 17.5 mg/kg, about 18 mg/kg, about 18.5 mg/kg, about 19 mg/kg, about 19.5 mg/kg, or about 20 mg/kg. In some embodiments, a variant is administered at a dose of about 0.5 mg, about 1 mg, about 2.5 mg, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg. When more than one variant is administered, the total amount of variants administered may be in accordance with the foregoing guidance.

Because nicotine poisoning is associated with vomiting, a non-oral route of administration may be used. Moreover, intravenous administration may be more effective than intraperitoneal administration. Thus, in some embodiments of methods of treating nicotine poisoning, a nicotine-degrading enzyme variant(s) (or composition comprising the same) is administered intravenously.

In some embodiments, the methods comprise administering a single dose of a nicotine-degrading enzyme variant(s) (or composition comprising the same). In some embodiments, the method comprises administering repeated doses, such as for a predetermined period of time or until the symptoms or effects of nicotine poisoning or toxicity are reduced, ameliorated, or eliminated or until the subject has ceased smoking or otherwise consuming nicotine. In some embodiments, treatment is repeated with additional doses of the variant(s) if signs/symptoms/effects persist.

In some embodiments, treatment may continue for one or more days following overdose, such as for 1-3 days, or 1-5 days, or for 1, 2, 3, 4, or 5 days following overdose. In some embodiments, treatment may continue until the subject no long experiences any symptoms of nicotine poisoning or toxicity or until the levels of nicotine in the subject's plasma and/or brain have decreased to a sufficiently safe level. In some embodiments, the nicotine-degrading enzyme variant may be a long-acting nicotine-degrading enzyme variant as described above.

One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure. The following examples are given to illustrate the present invention. It should be understood, however, that the invention is not limited to the specific conditions or details of these examples.

EXAMPLES

Example 1—Development and Testing of Nicotine-Degrading Enzyme Variants

A synthetic gene (custom DNA synthesis by GeneArt/Invitrogen), codon optimized for *E. coli* expression of wild-type (wt) NicA2 amino acid sequence (GenBank accession number: AEJ14620.1) with a C-terminal His$_6$-tag was cloned into the NdeI-XhoI sites of pET-22b(+) (Novagen), and the expression plasmid transformed into *E. coli* BL21 (DE3). The predicted wild-type NicA2 amino acid sequence as expressed from this construct is shown in Table 1 (SEQ ID NO:1).

A heterogeneity in size was identified by SDS-PAGE of protein expressed from the construct encoding SEQ ID NO: 1 and purified by Immobilized Metal Affinity Chromatography (IMAC) using Cobalt TALON™ His-Tag Purification Resin (Clontech) according to the manufacturers protocol (FIG. 1; major and minor band around 49 kDa marker). As the protein was purified via the His-tag, the heterogeneity was inferred to be at the N-terminus. Utilizing the online search tool PRED-TAT (compgen.org/tools/PRED-TAT; Pantelis et al., *Combined prediction of Tat and Sec signal peptides with Hidden Markov Models*, 2010 BIOINFORMATICS), a putative TAT-leader sequence with an associated cleavage site following the alanine (A) residue at position 37 of SEQ ID NO:1 was identified.

In an effort to eliminate any non-essential bacterial sequence (including a specific in silico predicted T-cell epitope sequence at positions 16-24 of SEQ ID NO:1), to reduce immunogenic risk, as well as to eliminate the putative N-terminal cleavage site and the associated product heterogeneity, a deletion construct was made removing the first 50 N-terminal residues (NicA2Δ50; SEQ ID NO:2).

It was believed that this region could potentially be deleted without compromising catalytically activity; consequently NicA2Δ50 (SEQ ID NO: 2) was expressed in *E. coli* and purified as described above. As seen in FIG. 1, the purified NicA2Δ50 (SEQ ID NO: 2) appears homogeneous by SDS-PAGE analysis.

Analysis of enzymatic activity on purified protein was conducted using an Amplex Red assay (Reszka, et al., *Effects of peroxidase substrates on the Amplex red/peroxidase assay: Antioxidant properties of anthracyclines*, ANALYTICAL BIOCHEMISTRY 342: 327-337 (2005)). Briefly, the oxidation of nicotine by NicA2 results in generation of $H_2O_2$ which is coupled to the conversion of the colorless Amplex Red reagent into its red-fluorescent product, resorufin by HRP (horseradish peroxidase). The assay was performed essentially as recommended by the supplier of the assay kit (Thermo; Cat #A22188) with the exception of addition of S-Nicotine (Sigma) to a final assay concentration of 10 μM. Assays were run in a total volume of 100 μL/well in a black half-area flat bottom 96-well assay plate (Corning Cat #3993). Development of fluorescence was detected in a SpectraMax M2 multimode microplate plate reader (Molecular Devices) using the settings Ex at 555 nm; Em at 590 nm, employing a "Plate Blank" well to subtract values derived from a no enzyme control for each time point in the SoftMax Pro data evolution package (Molecular Devices). Activities were expressed as the relative slopes of increase in fluorescence plotted as a function of time compared to the wild-type NicA2 enzyme, which was run in parallel.

Figure 2:
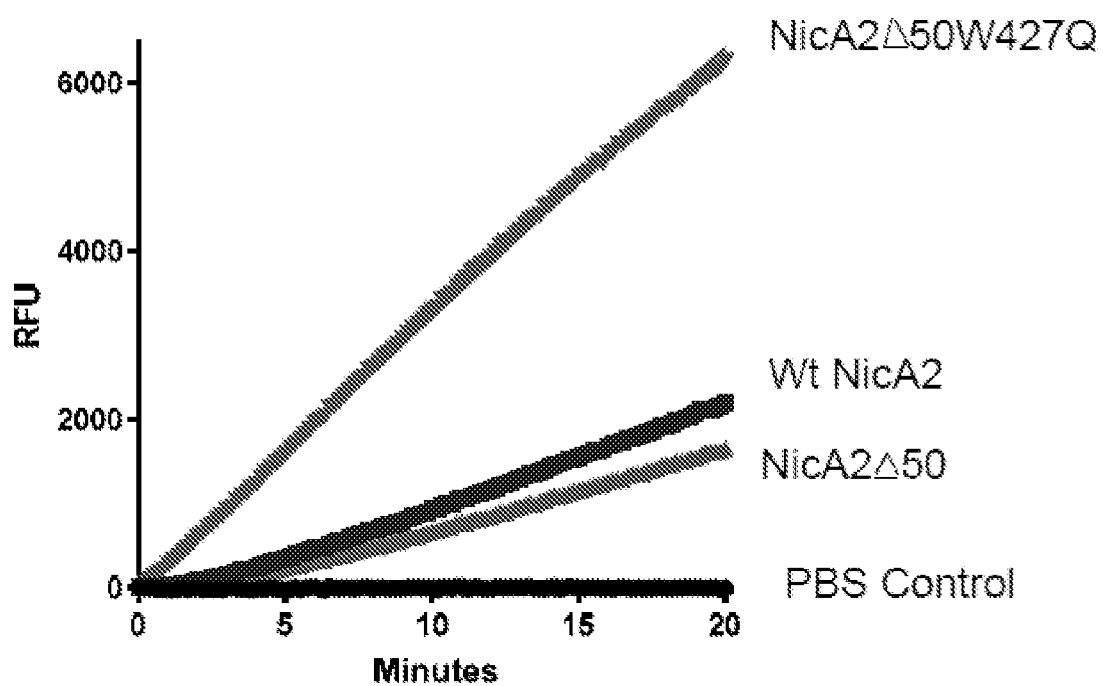
FIG. 2 shows results of a nicotine-degrading activity assay comparing wild-type NicA2 with variant nicotine-degrading enzymes as described herein. The assays used purified proteins at a final concentration of 80 nM.

The Amplex Red assay revealed that the purified NicA2Δ50 protein showed a 23% reduction in activity relative to wild-type NicA2 (FIG. 2 and Table 4). Two shorter deletion constructs (NicA2Δd25 (SEQ ID NO:3) and NicA2Δ38 SEQ ID NO:4) were generated and tested, but similarly showed decreases in activity compared to the wild-type enzyme. In summary, all three deletion mutants showed reduced activity relative to wild-type (Table 5).

TABLE 4

Relative Activities of NicA2 Variants (purified proteins)

| Variant | Activity in Amplex Red assay (rel. to wt NicA2); slopes of curves in FIG. 2 |
| --- | --- |
| Wt NicA2 (SEQ ID NO: 1) | 100% |
| NicA2Δ50 (SEQ ID NO: 2) | 77% |
| NicA2Δ50W427Q (SEQ ID NO: 5) | 276% |
| NicA2Δ50W427Q; I262A (SEQ ID NO: 62) | 111% |
| NicA2Δ50W427Q; I262T; N263R (SEQ ID NO: 63) | 248% |

TABLE 5

Relative Activities of NicA2 and NOX Variants (Screening Assay Format)

| Variant | Activity in Amplex Red assay (rel. to wt NicA2) |
| --- | --- |
| Wt NicA2 (SEQ ID NO: 1) | 100% |
| NicA2Δ25 (SEQ ID NO: 3) | 74% |
| NicA2Δ38 (SEQ ID NO: 4) | 71% |
| NicA2Δ50 (SEQ ID NO: 2) | 68% |
| NicA2Δ50W427Q (SEQ ID NO: 5) | 296% |
| NicA2Δ50W427E (SEQ ID NO: 6) | 305% |
| NicA2Δ50W427S (SEQ ID NO: 7) | 330% |
| NicA2Δ50W427M (SEQ ID NO: 8) | 275% |
| NicA2Δ50R91A (SEQ ID NO: 9) | 376% |
| NicA2Δ50R91Q (SEQ ID NO: 10) | 306% |
| NicA2Δ50R91F (SEQ ID NO: 11) | 270% |
| NicA2Δ50R91G (SEQ ID NO: 12) | 248% |
| NicA2Δ50R91T (SEQ ID NO: 13) | 237% |
| NicA2Δ50R91L (SEQ ID NO: 14) | 236% |
| NicA2Δ50R91S (SEQ ID NO: 15) | 205% |
| NicA2Δ50R91N (SEQ ID NO: 16) | 142% |
| NicA2Δ50T250G (SEQ ID NO: 17) | 469% |
| NicA2Δ50T250L (SEQ ID NO: 18) | 351% |
| NicA2Δ50T250R (SEQ ID NO: 19) | 193% |
| NicA2Δ50T250V (SEQ ID NO: 20) | 123% |
| NicA2Δ50K340P (SEQ ID NO: 21) | 207% |
| NicA2Δ50K340I (SEQ ID NO: 22) | 148% |
| NicA2Δ50K340V (SEQ ID NO: 23) | 130% |
| NicA2Δ50K340D (SEQ ID NO: 24) | 119% |
| NicA2Δ50K340E (SEQ ID NO: 25) | 96% |
| NicA2Δ50Q366K (SEQ ID NO: 26) | 493% |
| NicA2Δ50Q366E (SEQ ID NO: 27) | 322% |
| NicA2Δ50Q366V (SEQ ID NO: 28) | 236% |
| NicA2Δ50Q366L (SEQ ID NO: 29) | 219% |
| NicA2Δ50Q366I (SEQ ID NO: 30) | 191% |
| NicA2Δ50Q366V (SEQ ID NO: 31) | 140% |
| NicA2Δ50T381P (SEQ ID NO: 32) | 548% |
| NicA2Δ50T381I (SEQ ID NO: 33) | 537% |
| NicA2Δ50T381V (SEQ ID NO: 34) | 488% |
| NicA2Δ50T381Q (SEQ ID NO: 35) | 425% |
| NicA2Δ50T381N (SEQ ID NO: 36) | 265% |
| NicA2Δ50T381L (SEQ ID NO: 37) | 238% |
| NicA2Δ50T381M (SEQ ID NO: 38) | 213% |
| NicA2Δ50N462L (SEQ ID NO: 39) | 647% |
| NicA2Δ50N462Y (SEQ ID NO: 40) | 566% |
| NicA2Δ50N462S (SEQ ID NO: 41) | 421% |
| NicA2Δ50N462F (SEQ ID NO: 42) | 312% |
| NicA2Δ50N462G (SEQ ID NO: 43) | 302% |
| NicA2Δ50N462E (SEQ ID NO: 44) | 264% |
| NicA2Δ50N462A (SEQ ID NO: 45) | 221% |
| NicA2Δ50I463F (SEQ ID NO: 46) | 366% |
| NicA2Δ50I463Y (SEQ ID NO: 47) | 351% |
| NicA2Δ50I463A (SEQ ID NO: 48) | 129% |
| NicA2Δ50I463V (SEQ ID NO: 49) | 125% |
| NicA2Δ50I463L (SEQ ID NO: 50) | 114% |
| NicA2Δ50L217Q (SEQ ID N0: 51) | 278% |
| NicA2Δ50L217G (SEQ ID NO: 52) | 233% |
| NicA2Δ50L217E (SEQ ID NO: 53) | 203% |
| NicA2Δ50L217I (SEQ ID NO: 54) | 178% |
| NicA2Δ50L217C (SEQ ID NO: 55) | 179% |
| NicA2Δ50L217S (SEQ ID NO: 56) | 168% |
| Wt NOX (SEQ ID NO: 57) | 80% |
| NOXW423A (SEQ ID NO: 58) | 456% |
| NOXW423S (SEQ ID NO: 59) | 248% |
| NOXW423E (SEQ ID NO: 60) | 229% |
| NOXW423H (SEQ ID NO: 61) | 181% |
| NicA2A107R (SEQ ID NO: 124) | 1900% |
| NicA2A107K (SEQ ID NO: 125) | 670% |
| NicA2A107T (SEQ ID NO: 126) | 590% |
| NicA2F355C (SEQ ID NO: 127) | 260% |
| NicA2R91Q (SEQ ID NO: 129) | 330% |
| NicA2Q366K (SEQ ID NO: 130) | 310% |
| NicA2T381V (SEQ ID NO: 131) | 190% |
| NicA2N462Y (SEQ ID NO: 133) | 315% |
| NicA2Δ50A107R (SEQ ID NO: 134) | 1730% |
| NicA2F104L | 320% |
| NicA2G106S | 385% |

TABLE 5-continued

Relative Activities of NicA2 and NOX Variants (Screening Assay Format)

| Variant | Activity in Amplex Red assay (rel. to wt NicA2) |
|---|---|
| NicA2A107H | 480% |
| NicA2A107P | 350% |

Thus, it was decided to design and identify NicA2Δ50 variants that would exhibit nicotine-degrading activity at least equivalent to the wild-type. NOX variants were identified for further testing as well.

The NicA2 protein was visualized using Discovery Studio 4.5 (Dassault Systemes, BIOVIA Corp., San Diego Calif.) to determine active site residues. Based on inspection of the structure, location of FAD and reporting of putative critical active site residues (Tararina et al, 2016), a presumed active site cavity was defined. All residues making up the exposed surface of this cavity, including both side chains and backbone atoms, were classified as shell one residues (Table 2). Based on the defined shell one residues, residues similarly in direct contact with shell one were defined as shell two (Table 2). Residue locations were confirmed by manual inspection of the structure.

A synthetic double-stranded DNA fragment:

(SEQ ID NO: 64)
AAAGCAATATCGATGTGAATGATCGTGATGCAGTTACCCGTGAAGTTCAG

AAAATGTTTCCGGGTGTTGAAGTTCTGGGCACCGCAGCCTATGATTGGAC

CGCAGATCCGTTTAGCTTAGGTGCCNNKGCCGCGTATGGTGTTGGTCAGC

TGTCACGTCTGAAAGATCTGCAGGCAGCAGAAGGTCGTATTCTGTTTGCG

GGTGCAGAAACCAGCAATGGTTGGCATGCAAATATTGATGGTGCAGTTGA

AAGCGGTCTGCGTGCAGGTCGTGAAGTTAAACAGCTGCTGAGCGGTGGTG

GTGGATCCATAGG was digested with restriction enzymes ClaI and BamHI and the fragment cloned into the corresponding unique sites in the expression plasmid used for expression of NicA2Δ50.

The resulting library had an NNK randomization of shell one codon W427 (Table 2) resulting in a 32-member library (at the DNA/codon level) encoding variants with all possible 20 amino acids in said position. The library was transformed into BL21 Gold(DE3), and single colonies were picked and grown overnight in a 96 well plate in LB media containing Carbenicillin (100 µg/ml). Overnight LB cultures were diluted into a new 96-deep well plate containing 475 µl of auto-inducing Magic Media (Invitrogen)+Carbenicillin (100 µg/ml), and grown for 18h at room temperature with vigorous shaking. Bacteria were harvested in the plate by centrifugation at 4000 rpm for 15 minutes, and pellets frozen at −80° C. Pellets were lysed by dissolving in 100 µl of room temperature Bug Buster HT Reagent (Novagen) containing 1 KU of r-Lysozyme (Novagen) per 1 ml, and incubating on a shaking platform for 20 min at room temperature. Cleared lysates were prepared by diluting 1:1 (vol.:vol.) with Bug Buster HT Reagent and removing insoluble cell debris by centrifugation at 4400 rpm for 20 min at 4° C. 25 µl of cleared lysates were transferred to a new 96 well plate and diluted 1:1 (vol.:vol.) in 2% milk in PBS. Diluted lysates were transferred to the assay plate (black 96-well half area high binding plate (Corning) coated o/n at 4° C. with 5 µg/ml of anti-His Tag antibody (R&D Systems) in PBS; 50 µl per well; then blocked with 4% milk (in PBS) for 2h at RT) and incubated at room temperature gently shaking for 3 h to ensure saturation of the immobilized anti-His mAb with the molar excess of expressed His-tagged enzyme. This step essentially results in normalizing any differences in concentration afforded by differences in growth, induction conditions, intrinsic expression levels, etc., and ensures a consistent amount of enzyme is assayed for activity in each well in the subsequent steps. This also ablates the need for quantification of enzyme in individual wells to precisely measure and compare activity of variants. Plate was washed 6× with PBST and 1× with Amplex Red Reagent Buffer (Thermo) to remove unbound material. Enzyme assay was conducted by adding 50 µl of Amplex Red Solution including 10 µM S-Nicotine (as described above) to each well and monitoring development of fluorescence over time.

From one 96 well assay plate, the ten variants with the highest assay activities (all enhanced compared to values from included colonies expressing wild-type NicA2) were isolated from the master plate with overnight LB culture, and plasmid DNA was prepared and sequenced. Sequencing revealed sequence changes relative to NicA2Δ50 (SEQ ID NO:2) affording single mutations of W427 to Q, E, S, and M, resulting in SEQ ID NOs: 5, 6, 7, and 8, respectively. Additionally, further variants with mutations at positions 91, 217, 463, 381, 366, 340, 250, 427, or 462 of SEQ ID NO:1 were also designed and screened, as well as variants of NOX with mutations at position 423 of SEQ ID NO:57. A list of the activities of the identified variants in the Amplex Red screening assay (average for 8 individual colonies of each variant re-assayed as described above) is shown in Table 5.

The variant NicA2Δ50W427Q (SEQ ID NO:5) was expressed and purified as described above. An activity assay was conducted in parallel with purified wild-type NicA2 and NicA2Δ50 using the Amplex Red assay as described above. As shown in FIG. 2 and Table 4, the W427Q mutation surprisingly not only "restored" but actually significantly increased activity, with the NicA2Δ50W427Q variant exhibiting about 250% activity (a 2.5-fold increase) relative to the wild-type NicA2 enzyme. This data obtained using purified proteins is in agreement with the data generated in the screening assay format (Table 5).

A Protein BLAST homology search using NicA2 as query sequence yielded NOX, Nicotine amine oxidase from *Pseudomonas* sp. HZN6 (Qiu et al., Appl. Environ. Microbiol. 78, 2154-2160 (2012); Qiu et al., Appl. Environ. Microbiol. 79, 2164-2171 (2013)) as the closest relative, with an identity of 83%. A synthetic gene (custom synthesis by GeneArt/Invitrogen) codon optimized for *E. coli* expression of wild-type (wt) NOX amino acid sequence (GenBank accession number: AGH68979.1) with a C-terminal His$_6$-tag was cloned into the NdeI-XhoI sites of pET-22b(+), and the expression plasmid transformed into *E. coli* BL21(DE3). The predicted wild-type NOX amino acid sequence as expressed from this construct is shown in Table 1 (SEQ ID NO:57. NOX was purified and assayed in the Amplex Red activity assay. The enzyme did indeed display activity consistent with nicotine degradation and H$_2$O$_2$ formation, albeit at a 20% decreased activity relative to wt NicA2 (Table 5). Identifying improved NicA2 variants carrying mutations in W427 prompted the generation and screening of an NNK randomization library of the homologous W423 position of NOX. The library was generated using the QuikChange Site-Directed Mutagenesis Kit (Agilent), the DNA template encoding NOX in the pET22 expression vector described above, and the NNK primer NOX- W423NNK (Table 6, SEQ ID NO:65) as per the kit instructions. After plating transformations and incubation overnight at 37° C., 8 random colonies were sequenced for library QC, and remainder colonies scraped off the agar plates and pooled for DNA miniprep. This DNA was then transformed into the BL21 (DE3) expression strain, and individual clones screened as described for the NicA2Δ50W427NNK library above. Screening this library identified 4 variants with between 2- and 4.5-fold improved activity over wt NicA2: NOXW423A, S, E, and H (Table 5). Interestingly, given all these variants have an increased activity compared to wt NicA2, these could potentially be equally good starting points for biotherapeutic development, and beneficial mutations identified in NicA2 (e.g. all mutations disclosed in Table 5) may also be advantageous in the homologous positions in the NOX backbone.

Given the successful identification of improved variants in NicA2 position W427, similar "NNK libraries" in the NicA2Δ50 backbone were generated for other active site (shell one) positions: R91, T250, K340, Q366, T381, N462, I463F, as well as second shell residue L217. These later libraries were generated using the QUIKCHANGE™ Site-Directed Mutagenesis Kit (Agilent), a DNA template encoding NicA2Δ50 in the pET22 expression vector, and the NNK primers listed in Table 6, SEQ ID NO's 66-73, respectively, as per the kit instructions. As indicated in Table 5, screening of these libraries as described above led to identification of variants that had a range of 1- to 6.5-fold improvement in activity over wild-type NicA2 (SEQ ID NO's:5-56), in spite of carrying the A50 N-terminal deletion. Interestingly, even though L217 is a second shell residue (Table 3), 6 substitutions conferring 1.7- to 2.8-fold increased activity over wild-type were identified in this position (Table 5).

TABLE 6

Exemplary synthetic DNA oligonucleotides used for generation of NNK libraries

| Name: | SEQ ID NO: | Sequence |
| --- | --- | --- |
| NOX-W423NNK | 65 | TCC GTT TAG CCT GGG TGC ANN KGC AGC GTA TGG TGT TGG |
| NicA2-R91NNK | 66 | GAA GCA CGT AGC CGT TTA GGT GGT NNK ACC TTT ACC AGC CGT TTT |
| NicA2-T250NNK | 67 | ATG ATG CAT TCA TGG ATA CCG AAN NKC ATT ATC GTA TTC AGG GTG GCA C |
| NicA2-K340NNK | 68 | GGT CAG CTG AGT AAA GGT GCC NNK CTG TAT GTT CAT GTG AAA CAG |
| NicA2-Q366NNK | 69 | GAT GAA CAG CAG CCG CTG AAT TGG GTT NNK ACC CAT GAT TAT AGT GAT G |
| NicA2-T381NNK | 70 | GAA CTG GGC ACC ATT CTG AGC ATT NNK ATT GCA CGT AAA GAA ACC ATT G |
| NicA2-N462NNK | 71 | ACC AGC AAT GGT TGG CAT GCA NNK ATT GAT GGT GCA GTT GAA AGC |
| NicA2-I463NNK | 72 | GAA ACC AGC AAT GGT TGG CAT GCA AAT NNK GAT GGT GCA GTT GAA AGC |

TABLE 6-continued

Exemplary synthetic DNA oligonucleotides used for generation of NNK libraries

| Name: | SEQ ID NO: | Sequence |
| --- | --- | --- |
| NicA2-L217NNK | 73 | GCA CAG ATT AAT AGC TAT ATG GCA NNK TAT GCC GGT GAA ACC ACC GAT AAA |

To cover additional active site positions listed in Table 2, a custom Comprehensive Saturation Mutagenesis (CSM) library was supplied by Revolve Biotechnologies, Inc. (Firnberg et al., *PLoS One,* 7:e52031 (2012)), probing all single amino acid (aa) substitutions (one mutation per variant) in the following positions of full-length NicA2: PHE104, GLY105, GLY106, ALA107, TRP108, TYR214, TYR218, GLU249, PHE355, TRP364, TRP417, ALA426, and ALA461.

Screening of this library in the Amplex Red screening assay as described earlier lead to identification of improved variants NicA2A107R, NicA2A107K, NicA2A107T and NicA2F355C (Table 5; SEQ ID NO's 124-127).

In order to more efficiently screen through larger library sizes, a Fluorescence-Activated Cell Sorting (FACS) sorting protocol was implemented. Libraries containing NicA2 variants were cloned into the vector pET22b and transformed into the *E. coli* BL21(DE3) strain. Cells were inoculated in LB+100 μg/mL Ampicillin and grown at 37° C. until the OD600 reached 0.6-0.8. Expression was induced with 1 mM IPTG and the cultures were moved to 18° C. and expressed overnight. The next day, cells were washed in 5×PBS+1 mM EDTA to permeabilize the cells to nicotine before resuspending in the same buffer containing 5 μM Dihydrorhodamine 123 (DHR123), a redox sensitive dye that becomes fluorescent upon reaction with the hydrogen peroxide released by NicA2, and 5 mM nicotine. The cell suspension was transferred to a clean, sterile flask and incubated at room temperature while shaking. After 2 hours, cells were washed with 5×PBS+1 mM EDTA and sorted by FACS using the FITC channel to quantify DHR123 fluorescence. Recovered cells were re-grown in LB+100 μg/mL Ampicillin, and the protocol was repeated as needed.

Sequencing of clones from outputs resulting from one round of sorting of the CSM library enriched for putative NicA2 activity yielded the variants NicA2W427R, NicA2T250P, NicA2W427H; N462F, and NicA2W427L; N462M (SEQ ID NOs: 135-138, respectively).

Based on the results of improved variants NicA2Δ50R91Q, NicA2Δ50Q366K, NicA2Δ50T381V and NicA2Δ50N462Y, the same mutations were introduced into full-length NicA2, (resulting in NicA2R91Q, NicA2Q366K, NicA2T381V and NicA2N462Y with SEQ ID NOs: 129, 130, 131, 133, respectively), and activity assessed in the Amplex Red assay as previously described. As shown in Table 5, all these exemplary mutations provided activity enhancement in the full-length enzyme. Correspondingly, the high activity of the NicA2A107R variant (SEQ ID NO: 124) was retained in the NicA2Δ50A107R variant (SEQ ID NO: 134). Consequently, it is expected that all mutations listed in Table 5 will improve activity in the context of both full-length NicA2 and a deletion variant such as NicA2Δ50, NicA2Δ25, NicA2Δ38, or any similar deletion up to and including at least the first 50 N-terminal residues of NicA2, or any N- or C-terminal deletion variant provided this has an enzymatic activity of at least 20% of full-length wt NicA2.

Specific variants carrying mutations in multiple residues chosen from Table 5 can be generated by site-specific mutagenesis, and libraries consisting of multiple mutations in multiple positions chosen from Table 5 can be generated and screened as described above. These efforts could allow for the identification of variants with mutations in several positions in the same molecule with enzymatic activities higher than any of the individual single mutations listed in Table 5.

Having shown with the variants having SEQ ID NOs 2-4 that it is possible to delete the first epitope with only moderate effect on activity, and that this decrease in activity could be mitigated or overcome by mutations listed in Table 5, multiple other epitopes were investigated further.

Structure coordinates for the NicA2 protein were examined on Discovery Studio 4.5 (Dassault Systemes, BIOVIA Corp., San Diego Calif.) to determine immunogenic epitopes. Regions of the NicA2 sequence flagged as potential epitopes via T cell epitope scanning against the WIC allele DRB1*0401 (Immune Epitope Database and Analysis Resource, IEDB, iedb.org) were evaluated using a predictive site saturation mutagenesis protocol implemented in Discovery Studio to evaluate mutational energies. Favorably-scoring mutations in each previously defined region were cross-referenced with new rounds of IEDB T cell epitope predictions against WIC allele DRB1*0401 to find alterations that reduced predicted immunogenicity. The final selection of possible mutations was confirmed by visualization and manual evaluation of the probable structural changes in Discovery Studio. Table 3 sets forth exemplary mutations in the immunogenic T-cell epitopes that were predicted to decrease immunogenicity (based on in silico scoring as described above) while substantially retaining nicotine-degrading activity and stability.

Ten variants based on the mutations for Epitope 1 were generated by cloning the synthetic double-stranded DNA fragments (SEQ ID NOs: 74-83, Table 7) digested with restriction enzymes EcoRI and SacII into the corresponding unique sites in the expression plasmid used for expression of wild-type NicA2 (SEQ ID NO:1). The nucleic acid sequences of other exemplary epitope variants are shown in SEQ ID NOs: 84-113, as discussed in further detail below.

TABLE 7

Exemplary synthetic DNA fragments for generation of variants listed in Table 3

| SEQ ID NO: | Sequence |
|---|---|
| SEQ ID NO: 74 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGGCGAATCAGATGCTGACCGATAGCGGTGCCGAAGTT<br>CGTATGAGCGTTCCGGTTACCGCGGATAGG |
| SEQ ID NO: 75 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGAAAAATGCAATGGATACCGATAGCGGTGCCGAAGTT<br>CGTATGAGCGTTCCGGTTACCGCGGATAGG |
| SEQ ID NO: 76 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGACCAATGCAATGCTGACCGATAGCGGTGCCGAAGTTC<br>GTATGAGCGTTCCGGTTACCGCGGATAGG |
| SEQ ID NO: 77 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGAGCAATGCAATGCTGACCGATAGCGGTGCCGAAGTT<br>CGTATGAGCGTTCCGGTTACCGCGGATAGG |

TABLE 7-continued

Exemplary synthetic DNA fragments for generation of variants listed in Table 3

| SEQ ID NO: | Sequence |
| --- | --- |
| SEQ ID NO: 78 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGGATAATGCAATGAAAACCGATAGCGGTGCCGAAGTT<br>CGTATGAGCGTTCCGGTTACCGCGGATAGG |
| SEQ ID NO: 79 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGGCGAATGCAATGCTGACCGATAGCGGTGCCGAAGTT<br>CGTATGAGCGTTCCGGTTACCGCGGATAGG |
| SEQ ID NO: 80 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGACCAATCTGATGCTGACCGATAGCGGTGCCGAAGTTC<br>GTATGAGCGTTCCGGTTACCGCGGATAGG |
| SEQ ID NO: 81 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGACCCGTGCAATGCTGACCGATAGCGGTGCCGAAGTTC<br>GTATGAGCGTTCCGGTTACCGCGGATAGG |
| SEQ ID NO: 82 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGATTAATGCACATCTGACCGATAGCGGTGCCGAAGTTC<br>GTATGAGCGTTCCGGTTACCGCGGATAGG |
| SEQ ID NO: 83 | GCAATGAATTCGGTAAAAACATTCGCATTGCCTTTGAAAAACTGTG<br>TCATGATGCATGGGAAGTTTTTCCGCGTCCGCATGAACCGATGTTT<br>ACCGAACGTGCCCGTGAACTGGATAAATCAAGCGTTCTGGATCGT<br>ATTAAAACACTGGGTCTGAGCCGTCTGCAGCAGGCACAGATTAAT<br>AGCTATATGGCACTGTATGCCGGTGAAACCACCGATAAATTTGGTC<br>TGCCTGGTGTTCTGAAACTGTTTGCATGTGGTGGTTGGAATTATGA<br>TGCCTTTATGGATACCGAAACGCACTATCGTATTCAAGGTGGCACC<br>ATTGGTCTGGCGAATAACATGCTGACCGATAGCGGTGCCGAAGTT<br>CGTATGAGCGTTCCGGTTACCGCGGATAGG |
| SEQ ID NO: 84 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTA<br>ACCAGGGTCGTCGTACCCTGCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |

TABLE 7-continued

Exemplary synthetic DNA fragments for generation of variants listed in Table 3

| SEQ ID NO: | Sequence |
| --- | --- |
| SEQ ID NO: 85 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTA<br>ACCAGGGTAAACGTACCCTGCTGCTGGAAGCACGTAGCCGTTTAG<br>GTGGTCGTACCTTTACCAGCCGTTTTGCAGGTCAAGAAATTGAATT<br>TGGTGGTGCATGGGTTCATTGGTTACAGCCGCATGTTTGGGCAGAA<br>ATGCAGCGTTATGGTCTGGGTGTTGTTGAAGATCCGCTGACCAATC<br>TGGATAAAACCCTGATTATGTATAATGACGGTAGCGTGGAAAGCA<br>TTAGTCCGGATGAATTCATAGG |
| SEQ ID NO: 86 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTC<br>AGCAGGGTCGTCGTACCCTGCTGCTGGAAGCACGTAGCCGTTTAG<br>GTGGTCGTACCTTTACCAGCCGTTTTGCAGGTCAAGAAATTGAATT<br>TGGTGGTGCATGGGTTCATTGGTTACAGCCGCATGTTTGGGCAGAA<br>ATGCAGCGTTATGGTCTGGGTGTTGTTGAAGATCCGCTGACCAATC<br>TGGATAAAACCCTGATTATGTATAATGACGGTAGCGTGGAAAGCA<br>TTAGTCCGGATGAATTCATAGG |
| SEQ ID NO: 87 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTC<br>AGCAGGGTAACCGTACCCTGCTGCTGGAAGCACGTAGCCGTTTAG<br>GTGGTCGTACCTTTACCAGCCGTTTTGCAGGTCAAGAAATTGAATT<br>TGGTGGTGCATGGGTTCATTGGTTACAGCCGCATGTTTGGGCAGAA<br>ATGCAGCGTTATGGTCTGGGTGTTGTTGAAGATCCGCTGACCAATC<br>TGGATAAAACCCTGATTATGTATAATGACGGTAGCGTGGAAAGCA<br>TTAGTCCGGATGAATTCATAGG |
| SEQ ID NO: 88 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTA<br>ACCAGGGTCAGCGTACCCTGCTGCTGGAAGCACGTAGCCGTTTAG<br>GTGGTCGTACCTTTACCAGCCGTTTTGCAGGTCAAGAAATTGAATT<br>TGGTGGTGCATGGGTTCATTGGTTACAGCCGCATGTTTGGGCAGAA<br>ATGCAGCGTTATGGTCTGGGTGTTGTTGAAGATCCGCTGACCAATC<br>TGGATAAAACCCTGATTATGTATAATGACGGTAGCGTGGAAAGCA<br>TTAGTCCGGATGAATTCATAGG |
| SEQ ID NO: 89 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTA<br>ACCAGGGTCATCGTACCCTGCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |
| SEQ ID NO: 90 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTA<br>ACCAGGGTTATCGTACCCATCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |

TABLE 7-continued

Exemplary synthetic DNA fragments for generation of variants listed in Table 3

| SEQ ID NO: | Sequence |
| --- | --- |
| SEQ ID NO: 91 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTC<br>TGCAGGGTTATCGTACCTTTCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |
| SEQ ID NO: 92 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTC<br>TGCAGGGTCGTCGTACCCTGCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |
| SEQ ID NO: 93 | GCAATCATATGAGCGACAAAACCAAAACCAATGAAGGTTTTAGCC<br>GTCGCAGCTTTATTGGTAGCGCAGCAGTTGTTACCGCAGGCGTTGC<br>AGGTCTGGGTGCAATTGATGCAGCAAGCGCAACCCAGAAAACCAA<br>TCGTGCAAGCACCGTTAAAGGTGGCTTCGATTATGATGTTGTTGTG<br>GTTGGTGGTGGTTTTGCCGGTGCAACCGCAGCACGTGAATGTGGTC<br>TGCAGGGTTATCAGACCCTGCTGCTGGAAGCACGTAGCCGTTTAGG<br>TGGTCGTACCTTTACCAGCCGTTTTGCAGGTCAAGAAATTGAATTT<br>GGTGGTGCATGGGTTCATTGGTTACAGCCGCATGTTTGGGCAGAAA<br>TGCAGCGTTATGGTCTGGGTGTTGTTGAAGATCCGCTGACCAATCT<br>GGATAAAACCCTGATTATGTATAATGACGGTAGCGTGGAAAGCAT<br>TAGTCCGGATGAATTCATAGG |
| SEQ ID NO: 94 | GCAATCCGCGGTTGAACAGGTTAATGGTGGTGTTAAAATCAAAAC<br>CGATGACGATGAAATCATTACCGCAGGCACCAACGTTATTACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 95 | GCAATCCGCGGTTGAACAGGTTAATGGTGGTGTTAAAATCAAAAC<br>CGATGACGATGAAATCATTACCGCAGGCGTTGCGGTTCAGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 96 | GCAATCCGCGGTTGAACAGGTTAATGGTGGTGTTAAAATCAAAAC<br>CGATGACGATGAAATCATTACCGCAGGCGTTGCGGTTAACACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 97 | GCAATCCGCGGTTGAACAGGTTAATGGTGGTGTTAAAATCAAAAC<br>CGATGACGATGAAATCATTACCGCAGGCGTTGCGGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |

TABLE 7-continued

Exemplary synthetic DNA fragments for generation of variants listed in Table 3

| SEQ ID NO: | Sequence |
| --- | --- |
| SEQ ID NO: 98 | GCAATCCGCGGTTGAACAGGTTAATGGTGGTGTTAAAATCAAAAC<br>CGATGACGATGAAATCATTACCGCAGGCGTTGCGGTTCATACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 99 | GCAATCCGCGGTTGAACAGGTTAATGGTGGTGTTAAAATCAAAAC<br>CGATGACGATGAAATCATTACCGCAGGCGTTAACGTTCATACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 100 | GCAATCCGCGGTTGAACAGGTTAATGGTGGTGTTAAAATCAAAAC<br>CGATGACGATGAAATCATTACCGCAGGCGTTCAGGTTCATACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 101 | GCAATCCGCGGTTGAACAGGTTAATGGTGGTGTTAAAATCAAAAC<br>CGATGACGATGAAATCATTACCGCAGGCGTTAACGTTATTACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 102 | GCAATCCGCGGTTGAACAGGTTAATGGTGGTGTTAAAATCAAAAC<br>CGATGACGATGAAATCATTACCGCAGGCGTTACCGTTATTACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 103 | GCAATCCGCGGTTGAACAGGTTAATGGTGGTGTTAAAATCAAAAC<br>CGATGACGATGAAATCATTACCGCAGGCGTTGTTGTTATTACCGTT<br>CCGCGTAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCATTCTGAGCATTACCATTGCACGT<br>AAAGAAACCATCGATATAGG |
| SEQ ID NO: 104 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCAGCCTGAGCATTACCATTGCACGT<br>AAAGAAACCATCGATATAGG |
| SEQ ID NO: 105 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAAGCGGGCACCGCGCTGAGCATTACCATTGCACGT<br>AAAGAAACCATCGATATAGG |

TABLE 7-continued

Exemplary synthetic DNA fragments for generation of variants listed in Table 3

| SEQ ID NO: | Sequence |
|---|---|
| SEQ ID NO: 106 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACAGGGCACCGCGCTGAGCATTACCATTGCACGT<br>AAAGAAACCATCGATATAGG |
| SEQ ID NO: 107 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAAAACGGCACCGCGCTGAGCATTACCATTGCACGT<br>AAAGAAACCATCGATATAGG |
| SEQ ID NO: 108 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAAAACGGCACCATTCTGAGCATTACCCAGGCACGT<br>AAAGAAACCATCGATATAGG |
| SEQ ID NO: 109 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCGCGCTGAGCATTACCACCGCACGT<br>AAAGAAACCATCGATATAGG |
| SEQ ID NO: 110 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCGCGAACAGCATTACCATTGCACGT<br>AAAGAAACCATCGATATAGG |
| SEQ ID NO: 111 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCACCCTGAGCATTACCACCGCACGT<br>AAAGAAACCATCGATATAGG |
| SEQ ID NO: 112 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAACTGGGCACCACCCTGAGCATTACCATTGCACGT<br>AAAGAAACCATCGATATAGG |
| SEQ ID NO: 113 | GCAATCCGCGGTTGAACAGGTTAATGGTGGTGTTAAAATCAAAAC<br>CGATGACGATGAAATCATTACCGCAGGCGTTGTTGTTATGACCGTT<br>CCGCTGAATACCTATAAACATATTGGTTTTACACCGGCACTGAGCA<br>AAGGTAAACAGCGTTTTATCAAAGAAGGTCAGCTGAGTAAAGGTG<br>CCAAACTGTATGTTCATGTGAAACAGAATCTGGGTCGTGTTTTTGC<br>ATTTGCAGATGAACAGCAGCCGCTGAATTGGGTTCAGACCCATGA<br>TTATAGTGATGAAAACGGCACCATTCTGAGCATTACCATTCAGCGT<br>AAAGAAACCATCGATATAGG |

TABLE 7-continued

Exemplary synthetic DNA fragments for generation of variants listed in Table 3

| SEQ ID NO: | Sequence |
| --- | --- |
| SEQ ID NO: 114 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TCAGCTGAGCGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 115 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TGAACTGAACGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 116 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TGCGCTGAACGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 117 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TCAGCTGCAGGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 118 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TACCCTGCAGGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 119 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TGAACTGCTGGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 120 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TATTCTGTTTGCGGGTGCAGAAAAAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 121 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TATTCATGCGGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |

TABLE 7-continued

Exemplary synthetic DNA fragments for generation of variants listed in Table 3

| SEQ ID NO: | Sequence |
|---|---|
| SEQ ID NO: 122 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TATTCTGGCGGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |
| SEQ ID NO: 123 | AACCATCGATGTGAATGATCGTGATGCAGTTACCCGTGAAGTTCAG<br>AAAATGTTTCCGGGTGTTGAAGTTCTGGGCACCGCAGCCTATGATT<br>GGACCGCAGATCCGTTTAGCTTAGGTGCCTGGGCAGCGTATGGTGT<br>TGGTCAGCTGTCACGTCTGAAAGATCTGCAGGCAGCAGAAGGTCG<br>TGCGCTGTATGCGGGTGCAGAAACCAGCAATGGTTGGCATGCAAA<br>TATTGATGGTGCAGTTGAAAGCGGTCTGCGTGCAGGTCGTGAAGTT<br>AAACAGCTGCTGAGCGGTGGTGGTGGATCCGGTAGCGGTCATCAT<br>CACCATCATCATTAACTCGAGAATCG |

The ligations for the individual constructs were transformed in parallel into BL21 Gold(DE3), and 8 single colonies from each transformation were picked and grown overnight in a 96 well plate in LB media containing Carbenicillin (100 µg/ml). Screening of the 8 individual clones of each variant was performed as described above for screening of the W427NNK library, and the assay values reported as an average after eliminating potential rare outliers (never more than 1 of 8 clones total; typically resulting from clones without an insert or mutations within the cloned synthetic DNA) as seen in FIG. 4A-E. Five variants were identified with assay values >=90% of the activity of the wild-type NicA2 enzyme, indicating that these five variants (I262T; I262S; I262A; I262T & A264L; and I262T & N263R; see FIG. 4) have enzymatic activity similar to wild-type, and, based on in silico predictions, are predicted to have lower immunogenic potential.

Variants based on mutations in four other epitopes set forth in Table 3 were prepared and assessed as described above. For Epitope B, variants were generated by cloning the synthetic double-stranded DNA fragments (SEQ ID NOs 84-93, Table 7) digested with restriction enzymes NdeI and EcoRI; for Epitope 2 DNA fragments (SEQ ID NOs 94-103, Table 7) digested with SacII-ClaI; for Epitope 3 DNA fragments (SEQ ID Nos 102-113, Table 7) cut with SacII-ClaI; and for Epitope 4 DNA fragments (SEQ ID Nos 114-123, Table 7) cut with ClaI-XhoI, into the corresponding unique sites in the expression plasmid used for expression of wild-type NicA2 (SEQ ID NO:1). 8 random colonies from each ligation and transformation were tested as described above. As seen in FIG. 4A-E, 2, 4, and 7 variants were identified with assay values >=90% of the activity of the wild-type NicA2 enzyme from Epitope B, 2, and 3, respectively, indicating that these variants (L74N & Y77R, R78Q, V304A & M306Q, V394A, V304T & M306I, M306I & L310R, L374Q & I377S, L374A & I377A; L374N & I382Q, I377A & I382T, I377T & I382T, I377T, and L374N & A383Q; see FIG. 4) have enzymatic activity similar to wild-type, and, based on in silico predictions, are predicted to have lower immunogenic potential. Interestingly, none of the variants proposed for Epitope 4 showed more than 40% activity compared to wt NicA2 (see FIG. 4D). The mutations identified in this Example (one mutation from each epitope) can be introduced into the d50W427Q backbone, or combined with any of the other identified single mutation variants described in Table 5, or any number of mutations resulting from combination of mutations listed in Table 5, to produce a single de-immunized enzyme variant with enzymatic activity equal to or better than wt NicA2.

Two variants were generated combining deletion of the first epitope within the TAT leader sequence, mutating Epitope 1 using variants identified in FIG. 4, and containing the activity enhancing mutation W427Q: NicA2Δ50W427Q;I262A (SEQ ID: 62) and NicA2Δ50W427Q;I262T;N263R (SEQ ID: 63). These variants were purified, and enzymatic activity assessed in the Amplex Red assay as described above. As seen in Table 4, both variants have increased activity over wt despite having alteration that are likely to reduce immunogenicity.

Example 2—Identifying NicA2 MHCII Epitopes

An in silico search of NicA2 MHCII epitopes was performed based on the 8 most common HLA-DR alleles (Cantoret et al., PNAS 108: 1272-1277 (2011); DRB1*0101, DRB1*1501, DRB1*1301, DRB1*1101, DRB1*0801, DRB1*0701, DRB1*0401, and DRB1*0301). The search was done using the immune epitope database (Vita et al., Nucleic acids research, 43: D405-D412 (2015)) and percentile consensus rank method to assess the predicted immunogenic potential of NicA2. The percentile consensus score for each overlapping 15-mer NicA2 peptide was averaged across all the 8 HLA-DR alleles. The immunogenic potential of NicA2 was then determined by selecting all NicA2 sequences that were >1 standard deviation in tighter predicted binding to MHCII as compared to the overall averaged binding score. This method revealed eight contiguous sequences across 45% of the NicA2 sequence reflective of residues 10-32, 68-94, 189-225, 248-285, 296-327, 336-391 and 435-459 of SEQ ID NO:1 (highlighted in grey in Table 1) that are predicted to be broadly immunogenic.

A more narrow search using only the DRB1*0401 allele was performed in silico. This search yielded the six highest ranked immunogenic T-cell epitopes underlined in SEQ ID NO:1 of Table 1.

Example 3—PEGylation of Nicotine-Degrading Enzymes

Experiments were undertaken to develop protocols for conjugating polyethylene glycol (PEG) to NicA2 and other nicotine-degrading enzymes, such as NOX and the disclosed NOX variants, and to determine the effect of PEGylation on activity and half-life.

Figure 5:
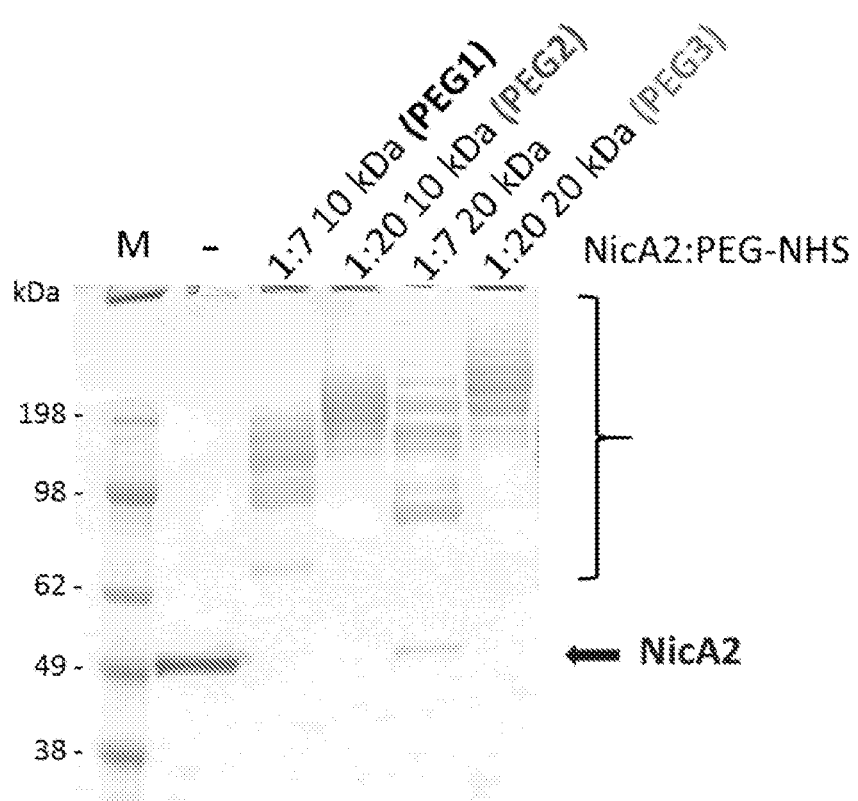
FIG. 5 shows random PEGylation of NicA2 using SDS-PAGE analysis. These results indicate that PEGylation can be increased by an increase in molar excess of PEGylation reagent and PEG chain length.

SDS-PAGE analysis indicated that the degree of PEGylation increases as the molar excess of PEGylation reagent and PEG chain length increases. Random PEGylation of wild-type (wt) NicA2 was performed at a protein concentration of 5 mg/mL and using 10 or 20 kDa NHS-PEG reagent (Sunbright® ME-100TS or ME-200TS; NOF America Corporation) at 7- or 20-fold molar excess in 100 mM $Na_3PO_4$, pH 7.6 on ice for >2 hours. Elimination of unconjugated PEG reagent was performed using Amicon Ultra-15 centrifugal filter units with a 50 kDa cutoff. Samples corresponding to 2 µg protein were loaded on an SDS-PAGE gel run in MOPS running buffer, and stained using SimplyBlue SafeStain (Invitrogen). As seen in FIG. 5, the degree of PEGylation could be controlled by controlling the excess molar ratios of PEGylation reagent. Preparations NicA2-PEG1, -PEG2, and -PEG3 where no residual unconjugated protein was detected by SDS-PAGE were chosen for further analysis.

Figure 6:
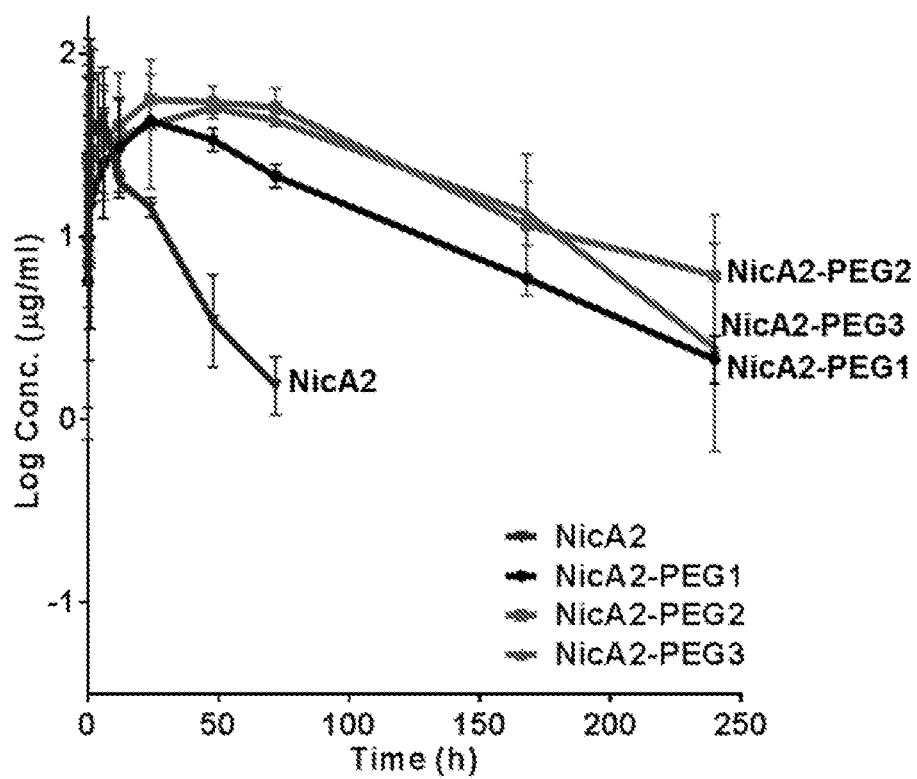
FIG. 6 shows PEGylation enhances the pharmacokinetic (PK) properties of NicA2 in the serum of animals administered PEGylated NicA2.

In order to determine whether PEGylation could enhance the pharmacokinetic (PK) properties of NicA2, serum concentrations were determined as a function of time after intravenous (i.v.) dosing in rats (5 mg/mL; N=4; 2M+2F). The data from these experiments are shown in FIG. 6. Briefly, MaxiSorp ELISA plates (Nunc) were coated overnight with anti-His tag antibody (R&D Systems), which could bind to the C-terminal His-tag on the NicA2 and PEGylated NicA2 proteins. Plates were blocked with 1% non-fat dry milk (NFDM) in phosphate buffered saline (PBS) for approximately 1 hour. Dilutions of NicA2 and NicA2-PEG1-3 standards and serum samples in 1% NFDM in PBS+0.1% Tween-20 were added to the plates and incubated for 2 hours at room temperature. After washing away unbound substances (all wash steps performed in PBS+0.1% Tween-20), rabbit anti-NicA2 polyclonal primary detection antibody was added to the wells for a 1 hour incubation. A wash step was followed by addition of horseradish peroxidase (HRP)-conjugated goat anti-rabbit IgG (Fc) (KPL International). Plates were washed, and the remaining binding complex was detected with TMB substrate (3,3',5,5'-tetramethylbenzidine; KPL International). Once stopped with acid, plates were read on a spectrophotometer at 450 nm and data analyzed in SoftMax® Pro, version 5.4 (Molecular Devices).

Figure 7:
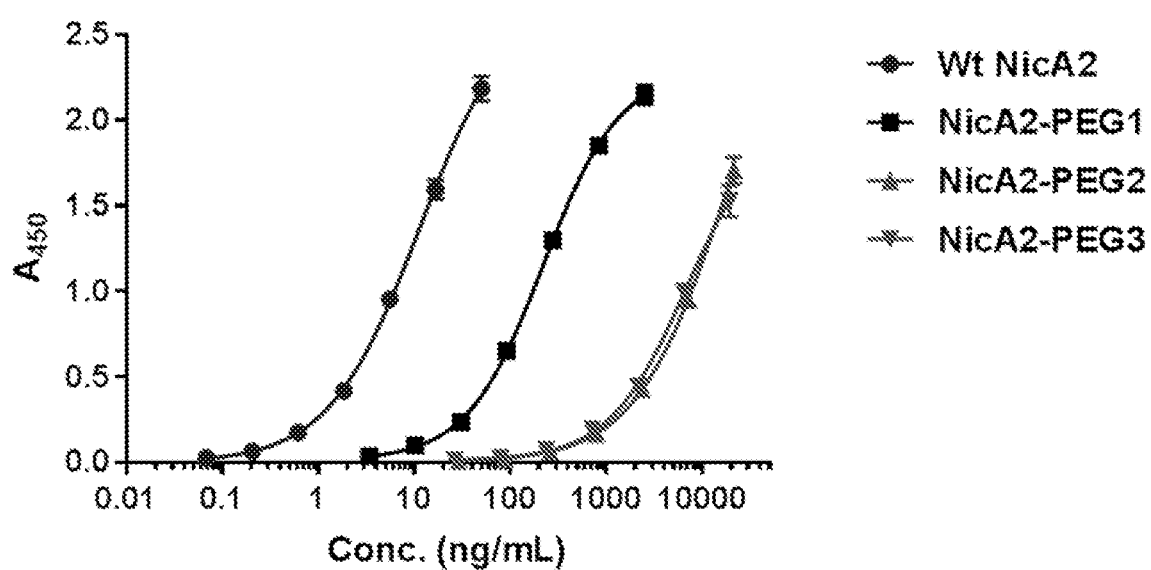
FIG. 7 shows PEGylation can mask potentially immunogenic epitopes on NicA2.

Additional experiments were performed to determine whether PEGylation masks epitopes on NicA2. Serial dilutions in PBS of unPEGylated or PEGylated preparations of NicA2 were tested in the same sandwich ELISA assay used for measurement of serum concentrations in the PK experiment described above (FIG. 6), and signal (A450) plotted as a function of concentration. Assay sensitivity is dramatically reduced with increasing degree of PEGylation (approx. 1000-fold higher concentration of NicA2-PEG2 and -PEG3 required to obtain an A450 of 1.0 relative to unPEGylated molecule), indicating that epitopes recognized by the detection antibody reagents are less accessible in the PEGylated molecules. These results are shown in FIG. 7.

Figure 8:
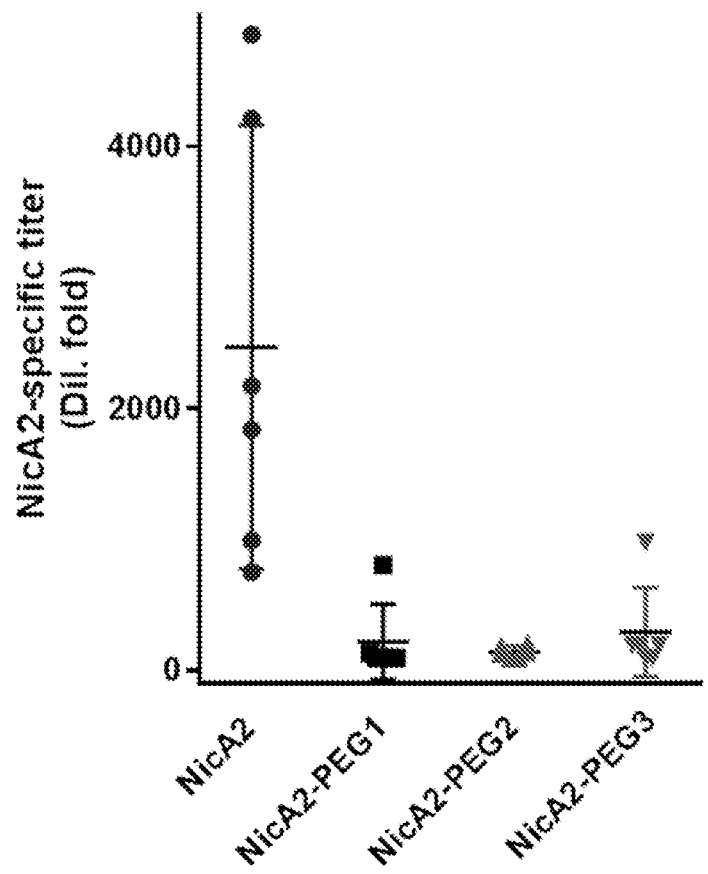
FIG. 8 shows PEGylation can decrease titers of NicA2-specific antibodies in a transgenic HLA-DR4 mouse model of immunogenicity. PEGylation of NicA2 led to a significant (≥10-fold) decrease in average NicA2-specific antibody titers in transgenic DR4 mice (4, 2, and 2, animals from groups NicA2-PEG1, -PEG2, and -PEG3, respectively, had titers below the limit of detection (LOD)), suggesting a lower immunogenic potential in a clinical setting.

PEGylation was shown to decrease titers of NicA2-specific antibodies in a transgenic HLA-DR4 mouse model of immunogenicity. In particular, the reduction of NicA2-specific antibody titers 10 days after subcutaneous (s.c.) injection in Freunds Incomplete Adjuvant in human DR4 transgenic mice (N=6; 3M+3F; Taconic Biosciences) was studied. This mouse model carries a hybrid MEW class II molecule with the antigen binding domains of human HLA-DRA and HLA-DRB*0401 (representative of the DR4 supertype) and does not express endogenous mouse MEW class II molecules. Titer was defined as serum dilution to achieve OD450=0.5 in ELISA using NicA2 coated plates, and detection by goat α-mouse IgG-γ-HRP. The lowest serum dilution tested was 50-fold (Limit Of Detection (LOD); indicated by a dashed line in FIG. 8). PEGylation of NicA2 led to a significant ≥10-fold decrease in average NicA2-specific antibody titers in transgenic DR4 mice (FIG. 8; 4, 2, and 2, animals from groups NicA2-PEG1, -PEG2, and -PEG3, respectively, had titers below LOD), indicating that PEGylated variants may exhibit lower immuogenicity in a clinical setting.

Figure 9:
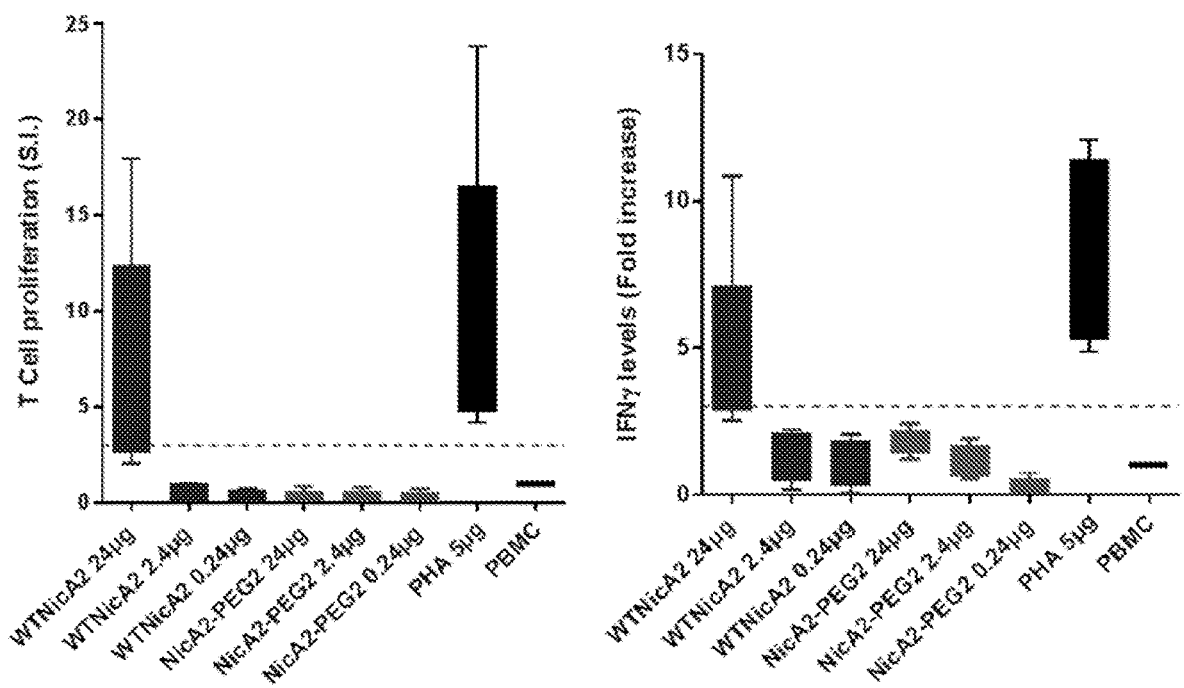
FIG. 9 shows PEGylation attenuates the human T-cell proliferation response and cytokine TNFγ release mediated by exposure to NicA2. PEGylation of NicA2 led to a significant decrease in average T Cell proliferation Stimulation Index (left panel) as well as a decrease in IFNγ secretion levels (right panel). An increase of 3≥(dashed line) is considered a significant increase and a positive response.

It was also observed that PEGylation attenuates the human T-cell proliferation response and cytokine TNFγ release mediated by exposure to NicA2, as shown in FIG. 9. PEGylation of NicA2 led to a significant decrease in average T Cell proliferation Stimulation Index (FIG. 9, left panel) as well as decrease in IFNγ secretion levels (FIG. 9, right panel) (Independent experiments from five healthy volunteers). Positive control: phytohaemagglutinin (PHA). Test results for five independent experiments are shown for T cell proliferation response stimulation indexes (SI; measured by 3H-Thymidine uptake) (left) and fold increase in IFNγ secretion levels (measured by flow cytometry and a Cytometric Bead Array kit (BD Biosciences)) (right) for NicA2 and NicA2-PEG2 at three test concentrations in comparison to baseline responses (PBMC). An increase of 3≥(dashed line) is considered a significant increase and a positive response.

Figure 10:
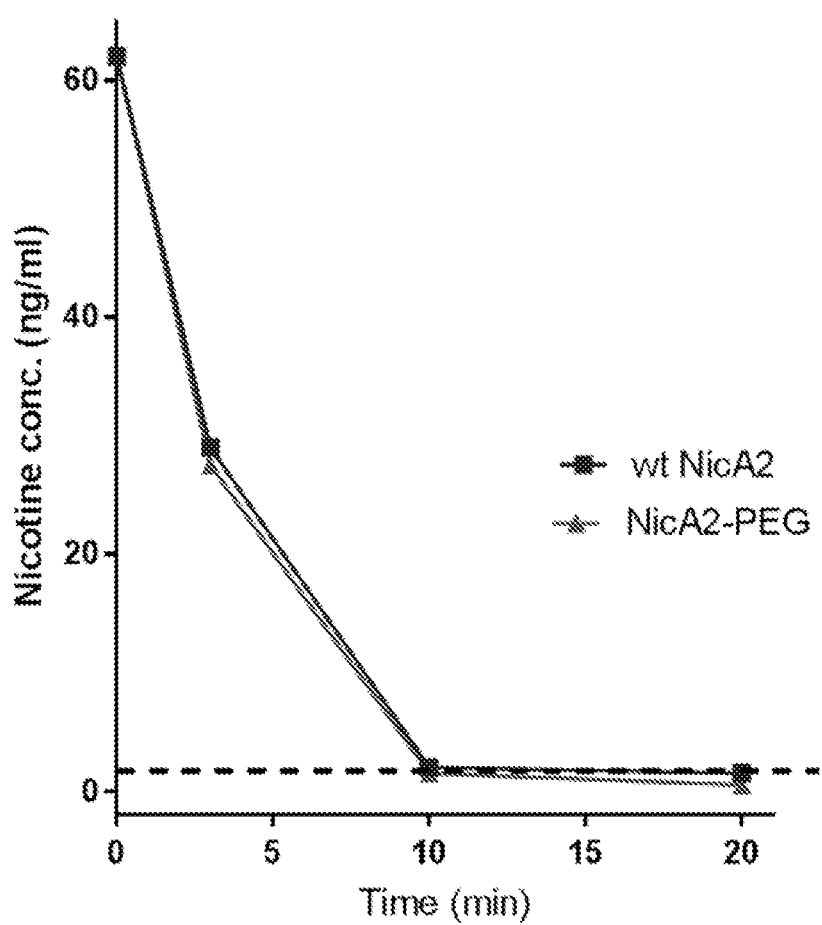
FIG. 10 shows PEGylated NicA2 enzymes retain full nicotine degrading activity in serum. PEGylation did not appear to impede NicA2's ability to degrade nicotine in rat serum.

It also was shown that PEGylated enzymes retained full nicotine degrading activity in serum, as shown in FIG. 10. Wt NicA2 or NicA2-PEG2 was added to a final concentration of 0.075 mg/ml into rat serum containing 40 ng/mL S-nicotine (250 nM, which is equivalent to plasma levels observed in a typical smoker) pre-incubated at 37° C. Samples were withdrawn at various time points, and enzymatic activity immediately quenched by addition of methanol and rapid mixing. Residual nicotine concentrations were determined by gas chromatography (GC). LOD of the GC assay was 2 ng/mL indicated by the dashed line. PEGylation did not appear to impede NicA2's ability to degrade nicotine.

Example 4—Nicotine Degrading Activity in Serum

To confirm that activity was improved not only in assay buffer and at the high (10 µM) nicotine concentration of the Amplex Red assay (discussed in Example 1; see, e.g., Tables 4 and 5), but also in serum concentrations more relevant to those encountered in a typical smoker, an exemplary representative variant from the Amplex Red assay (NicA2A107R) was assessed in an assay utilizing serum rather than a buffer solution (the same assay used to produce the data shown in FIG. 10).

Figure 11:
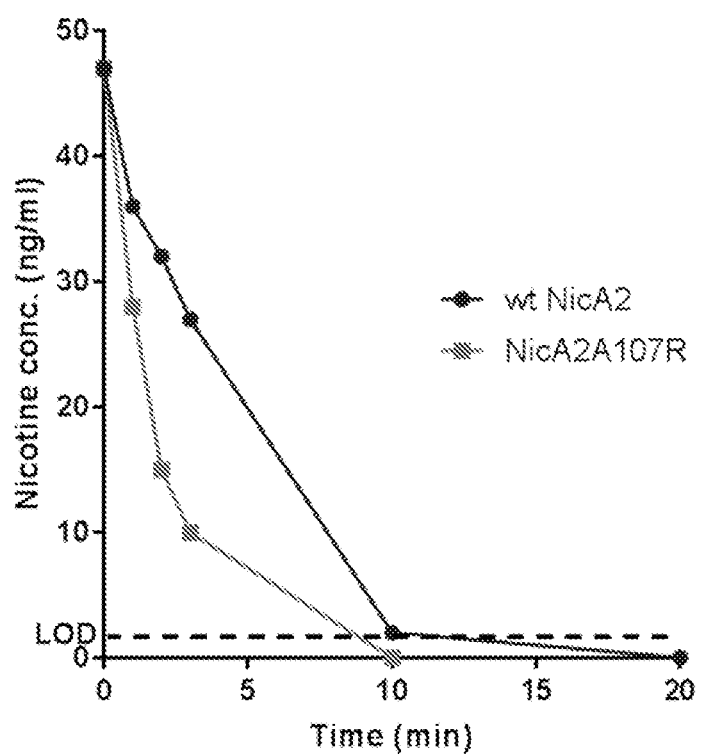
FIG. 11 shows that a NicA2 variant with a A107R substitution has increased activity in serum at low nicotine concentrations compared to wild-type NicA2.

Briefly, NicA2A107R was added to a final concentration of 0.075 mg/ml into rat serum containing 40/ng/ml of S-(−)-nicotine (250 nM). As seen in FIG. 11, variant NicA2A107R has increased nicotine degrading activity under these conditions compared to wt NicA2, at serum concentrations that would be found in smokers.

Example 5—Treating Nicotine Poisoning

The maximum sub-lethal dose of nicotine in balb/c mice was determined to be 2 mg/kg intraperitoneally. The effects of nicotine were dose dependent, and included sedation, straub tail, tremors, tachypnea, back arching, rapid movements of the legs, wild running, loss of righting response, and clonic/tonic seizures. In this experiment, wild-type NicA2 was used as a proof of concept to show that the disclosed enzyme variants are capable of treating nicotine poisoning or toxicity.

Seven to eight week old balb/c mice (N=5 for each group) were pretreated with 775 mg/kg of wtNicA2 or a negative control (both i.v.) 15 minutes prior to administration of nicotine at the sub-lethal dose of 2 mg/kg. Over the course of 5 minutes, the mice were monitored for seizures and phenotypic indications of nicotine poisoning or toxicity and scored according to the rubric in Table 8, in which a score of less than 3 indicates that there was no seizure. Sensitivity to seizure was computed by determining the percentage of animals that had a score of 4 or 5.

TABLE 8

Nicotine Poisoning Phenotypic Scoring

| Score | Signs & Symptoms |
|---|---|
| 0 | no visible effects |
| 1 | locomotor effects including increased exploring activity and/or sedation |
| 2 | tachypnea, tremors, back arching |
| 3 | any combination of the symptoms in 1 and 2 plus rapid movements of the legs, wild running, or partial loss of righting reflex |
| 4 | any combination of the previous symptoms plus complete loss of righting reflex, clonic seizures, and tonic seizures |
| 5 | any combination of the preceding symptoms plus death, with or without hyperextension of the limbs along the axis of the body (soldier position) |

As shown in Table 9 below, all untreated mice had severe seizures, while none of the mice pretreated with NicA2 had seizures. Accordingly, these results indicate that the disclosed nicotine-degrading enzyme variants can be used to treat nicotine poisoning.

TABLE 9

| Score | Dose | Sensitivity to Seizure | <4 | >=4 | 0 | 1 | 2 | 3 | 4 | 5 |
|---|---|---|---|---|---|---|---|---|---|---|
| Control | 0 | 100% | | N = 5 | | | | | | 5 |
| wt NicA2 | 775 mg/kg | 0% | N = 5 | | | | 2 | 2 | 1* | |

*Administration was i.p. rather than i.v.

Similar experiments in a rat seizure model (using a challenge dose of nicotine of 4 mg/kg i.p. since rats are more tolerant of nicotine than mice) using lower doses of wtNicA2 (70 mg/kg and 140 mg/kg) were not effective. Thus, the dose of enzyme may be important to providing effective treatment.

The 775 mg/kg dose used successfully in the mouse experiment is not a practical dose for humans. However, as shown above, nicotine-degrading enzyme variants described herein have greater nicotine-degrading activity than the wild-type enzyme. Thus, it is believed that the enzyme variants disclosed herein will be effective against nicotine poisoning at doses suitable for use in humans.

Example 6—Treating Nicotine Addiction and/or Facilitating Smoking Cessation

This example illustrates methods of using a variant as described herein to treat nicotine addiction and/or facilitate smoking cessation in a human adult.

An adult human subject who regularly smokes cigarettes but wishes to quit is administered a therapeutically effective amount of a pharmaceutical compositions comprising a nicotine-degrading enzyme variant (e.g., NicA2Δ50W427Q; SEQ ID NO: 5, or a long-acting version thereof) orally or by intravenous or subcutaneous injection. The subject is evaluated for levels of nicotine circulating in plasma, as well as for the presence and/or severity of signs and symptoms associated with nicotine withdrawal, such as headache, irritability, anxiety, and sleeplessness, as well as the number of cigarettes smoked in a given day. The subject is treated with repeated administrations until levels of nicotine circulating in plasma reach a target (reduced) level, and/or until one or more signs/symptoms of nicotine withdrawal are reduced, ameliorated, or eliminated, and/or until the subject has reduced the level of consumption of nicotine products (e.g., is smoking fewer cigarettes per day), and/or until the subject has ceased consumption of nicotine products (e.g., has quit smoking).

Example 7—Treatment of a Pediatric Patient with a Nicotine-Degrading Enzyme Variant This example illustrates methods using nicotine-degrading enzyme variants in the treatment of nicotine poisoning in a pediatric patient.

A child known to have or suspected of having ingested nicotine is administered a therapeutically effective amount of a pharmaceutical composition comprising a nicotine-degrading enzyme variant, by intravenous, intramuscular, or subcutaneous injection. The child is evaluated for the presence and/or severity of signs and symptoms associated with nicotine poisoning, including, but not limited to, seizures, coma, shortness of breath, and increased heart rate, and the child is treated until one or more signs/symptoms is reduced, ameliorated, or eliminated. Optionally, another dose of the pharmaceutical composition is administered if signs/symptoms persist and/or if nicotine plasma/brain levels remain elevated.

What is claimed is:

1. A nicotine-degrading enzyme variant comprising an amino acid sequence that is a variant of the amino acid sequence of the wild-type NicA2 enzyme set forth in SEQ ID NO: 1, wherein the variant sequence has at least 90% sequence identity to a sequence selected from (i) SEQ ID NO: 1 and (ii) SEQ ID NO: 1 having an N-terminal deletion of up to 52 amino acids, and wherein the variant comprises at least one substitution at an amino acid position selected from positions 91, 104, 106, 107, 217, 250, 340, 366, 381, 427, 462, and 463 of SEQ ID NO:1, and has nicotine-degrading activity.

2. The variant of claim 1, wherein the variant sequence comprises at least one substitution selected from:
   a. R91A, R91Q, R91F, R91G, R91T, R91L, R91S, and R91N;
   b. F104L;
   c. G106S;
   d. A107H, A107P, A107R, A107K, and A107T;
   e. L217Q, L217G, L217E, L217I, L217C, and L217S;
   f. T250P, T250G, T250L, T250R, and T250V;
   g. K340P, K340I, K340V, K340D and K340E;
   h. Q366K, Q366E, Q366V, Q366L, Q366I, and Q366Y;
   i. T381P, T381I, T381V, T381Q, T381N, T381L, and T381M;
   j. W427R, W427H, W427L, W427Q, W427E, W427S, or W427M
   k. N462M, N462L, N462Y, N462S, N462F, N462G, N462E, and N462A; and
   l. I463F, I463Y, I463A, I463V, and I463L.

3. The variant of claim 1, wherein the variant sequence comprises at least one substitution selected from A107R and A107T.

4. The variant of claim 3, wherein the variant sequence further comprises at least one substitution, addition, or deletion in an immunogenic T-cell epitope at an amino acid position selected from positions 74, 77, 78, 80, 262-266, 303, 304, 306, 310, 374, 377, 378, 382, 383, 450-452, and 457 of SEQ ID NO:1.

5. The variant of claim 3, wherein the variant sequence further comprises at least one substitution, addition, or deletion in an immunogenic T-cell epitope at an amino acid position selected from positions 16-24, 73-81, 258-266, 302-310, 373-381, and 447-455 of SEQ ID NO: 1.

6. The variant of claim 3 wherein the variant sequence further comprises at least one substitution, addition, or deletion at a position selected from:
   (a) amino acid positions 74, 77, 78, or 80 of SEQ ID NO: 1;
   (b) amino acid positions 262, 263, 264, or 266 of SEQ ID NO: 1;
   (c) amino acid positions 303, 304, 306, or 310 of SEQ ID NO: 1;
   (d) amino acid positions 374, 377, 378, 382, or 383 of SEQ ID NO: 1; and/or
   (e) amino acid positions 450, 451, 452, or 457 of SEQ ID NO: 1.

7. The variant of claim 3, wherein the variant sequence further comprises at least one substitution or substitution combination selected from:
   (a) L74N and Y77R;
   (b) L74N and Y77K;
   (c) L74Q and Y77R;
   (d) L74Q and Y77N;
   (e) L74N and Y77Q;
   (f) L74N and Y77H;
   (g) L74N and L80H;
   (h) L80F;
   (i) Y77R;
   (j) R78Q;

(k) I262A and A264Q;
(l) I262K and L266D;
(m) I262T;
(n) I262S;
(o) I262D and L266K;
(p) I262A
(q) I262T and A264L;
(r) I262T and N263R;
(s) M265H;
(t) I262A and A264N;
(u) V303T, V304N, and M306I;
(v) V304A and M306Q;
(w) V304A, M306N;
(x) V304A;
(y) V304A and M306H;
(z) V304N and M306H;
(aa) V304Q and M306H;
(bb) V304N, M306I;
(cc) V304T and M306I;
(dd) L374Q and I377S;
(ee) L374A and I377A;
(ff) L374Q and I377A;
(gg) L374N and I377A;
(hh) L374N and I382Q;
(ii) I377A and I382T;
(jj) I377A and L378N;
(kk) I377T and I382T;
(ll) I377T; and
(mm) L374N and A383Q;
(nn) I448Q and F450S;
(oo) I448E and F450N;
(pp) I448A and F450N;
(qq) I448Q and F450Q;
(rr) I448T and F450Q;
(ss) I448E and F450L;
(tt) T455K;
(uu) L449H and F450A;
(vv) F450A;
(ww) I448A and F450Y;
(xx) I262T;
(yy) I262S;
(zz) I262A;
(aaa) I262T and A264L;
(bbb) I262T and N263R; and
(ccc) M306I and L310R.

8. The variant of claim 1, comprising a deletion of at least amino acids 1-38 of SEQ ID NO:1 or a deletion of amino acids 1-50 of SEQ ID NO:1.

9. The variant of claim 1, wherein the variant is a long-acting variant fused to a compound selected from the group consisting of an albumin-binding peptide, an albumin-binding protein domain, human serum albumin, an inert polypeptide, recombinant PEG (XTEN), a homo-amino acid polymer (HAP), a proline-alanine serine polymer (PAS), and an elastin-like peptide (ELP), and polyethylene glycol (PEG).

10. The variant of claim 9, wherein the long-acting variant is PEGylated.

11. A pharmaceutical composition comprising a nicotine-degrading enzyme variant of claim 1 and a pharmaceutically acceptable carrier.

12. A nicotine-degrading enzyme variant having nicotine-degrading activity and comprising an amino acid sequence having at least about 95% sequence identity to a sequence selected from (i) SEQ ID NO: 1 and (ii) SEQ ID NO: 1 having an N-terminal deletion of up to 52 amino acids, wherein said variant comprises at least one substitution at an amino acid position selected from the group consisting of positions 91, 104, 106, 107, 217, 250, 340, 366, 381, 427, 462, and 463 of SEQ ID NO:1.

13. The nicotine-degrading enzyme variant of claim 12, wherein said variant sequence comprises at least one substitution selected from:
   a. R91A, R91Q, R91F, R91G, R91T, R91L, R91S, and R91N;
   b. F104L;
   c. G106S;
   d. A107H, A107P, A107R, A107K, and A107T;
   e. L217Q, L217G, L217E, L217I, L217C, and L217S;
   f. T250P, T250G, T250L, T250R, and T250V;
   g. K340P, K340I, K340V, K340D and K340E;
   h. Q366K, Q366E, Q366V, Q366L, Q366I, and Q366Y;
   i. T381P, T381I, T381V, T381Q, T381N, T381L, and T381M;
   j. W427R, W427H, W427L, W427Q, W427E, W427S, or W427M
   k. N462M, N462L, N462Y, N462S, N462F, N462G, N462E, and N462A; and
   l. I463F, I463Y, I463A, I463V, and I463L.

14. A nicotine-degrading enzyme variant having nicotine-degrading activity and comprising an amino acid sequence of:
   (i) SEQ ID NO: 1 with at least one substitution at one or more amino acid positions selected from the group consisting of positions 91, 104, 106, 107, 217, 250, 340, 366, 381, 427, 462, and 463 of SEQ ID NO:1, or
   (ii) SEQ ID NO: 1 having an N-terminal deletion of up to 52 amino acids and at least one substitution at one or more amino acid positions selected from the group consisting of positions 91, 104, 106, 107, 217, 250, 340, 366, 381, 427, 462, and 463 of SEQ ID NO:1.

15. The nicotine-degrading enzyme variant of claim 14, wherein at least one of said substitutions is selected from the group consisting of:
   a. R91A, R91Q, R91F, R91G, R91T, R91L, R91S, and R91N;
   b. F104L;
   c. G106S;
   d. A107H, A107P, A107R, A107K, and A107T;
   e. L217Q, L217G, L217E, L217I, L217C, and L217S;
   f. T250P, T250G, T250L, T250R, and T250V;
   g. K340P, K340I, K340V, K340D and K340E;
   h. Q366K, Q366E, Q366V, Q366L, Q366I, and Q366Y;
   i. T381P, T381I, T381V, T381Q, T381N, T381L, and T381M;
   j. W427R, W427H, W427L, W427Q, W427E, W427S, or W427M
   k. N462M, N462L, N462Y, N462S, N462F, N462G, N462E, and N462A; and
   l. I463F, I463Y, I463A, I463V, and I463L.

16. The nicotine-degrading enzyme variant of claim 15, wherein at least one of said substitutions is selected from A107R and A107T.

17. The variant of claim 16, comprising a deletion of at least amino acids 1-38 of SEQ ID NO:1 or a deletion of amino acids 1-50 of SEQ ID NO:1.

18. The variant of claim 16, wherein the variant is a long-acting variant fused to a compound selected from the group consisting of an albumin-binding peptide, an albumin-binding protein domain, human serum albumin, an inert polypeptide, recombinant PEG (XTEN), a homo-amino acid polymer (HAP), a proline-alanine serine polymer (PAS), and an elastin-like peptide (ELP), and polyethylene glycol (PEG).

19. The variant of claim 18, wherein the long-acting variant is PEGylated.

20. A pharmaceutical composition comprising the nicotine-degrading enzyme variant of claim 14 and a pharmaceutically acceptable carrier.

21. A pharmaceutical composition comprising the nicotine-degrading enzyme variant of claim 16 and a pharmaceutically acceptable carrier.

22. The variant of claim 12, wherein the variant sequence further comprises at least one substitution or substitution combination selected from:
  (a) L74N and Y77R;
  (b) L74N and Y77K;
  (c) L74Q and Y77R;
  (d) L74Q and Y77N;
  (e) L74N and Y77Q;
  (f) L74N and Y77H;
  (g) L74N and L80H;
  (h) L80F;
  (i) Y77R;
  (j) R78Q;
  (k) I262A and A264Q;
  (l) I262K and L266D;
  (m) I262T;
  (n) I262S;
  (o) I262D and L266K;
  (p) I262A
  (q) I262T and A264L;
  (r) I262T and N263R;
  (s) M265H;
  (t) I262A and A264N;
  (u) V303T, V304N, and M306I;
  (v) V304A and M306Q;
  (w) V304A, M306N;
  (x) V304A;
  (y) V304A and M306H;
  (z) V304N and M306H;
  (aa) V304Q and M306H;
  (bb) V304N, M306I;
  (cc) V304T and M306I;
  (dd) L374Q and I377S;
  (ee) L374A and I377A;
  (ff) L374Q and I377A;
  (gg) L374N and I377A;
  (hh) L374N and I382Q;
  (ii) I377A and I382T;
  (jj) I377A and L378N;
  (kk) I377T and I382T;
  (ll) I377T; and
  (mm) L374N and A383Q;
  (nn) I448Q and F450S;
  (oo) I448E and F450N;
  (pp) I448A and F450N;
  (qq) I448Q and F450Q;
  (rr) I448T and F450Q;
  (ss) I448E and F450L;
  (tt) T455K;
  (uu) L449H and F450A;
  (vv) F450A;
  (ww) I448A and F450Y;
  (xx) I262T;
  (yy) I262S;
  (zz) I262A;
  (aaa) I262T and A264L;
  (bbb) I262T and N263R; and
  (ccc) M306I and L310R.

23. A pharmaceutical composition comprising the nicotine-degrading enzyme variant of claim 12 and a pharmaceutically acceptable carrier.

24. A pharmaceutical composition comprising the nicotine-degrading enzyme variant of claim 17 and a pharmaceutically acceptable carrier.

* * * * *

UNITED STATES PATENT AND TRADEMARK OFFICE
CERTIFICATE OF CORRECTION

PATENT NO. : 11,597,916 B2
APPLICATION NO. : 16/483380
DATED : March 7, 2023
INVENTOR(S) : Kalnik et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 402 days.

Signed and Sealed this
Thirty-first Day of December, 2024

Derrick Brent
*Acting Director of the United States Patent and Trademark Office*